United States Patent
Springer et al.

(10) Patent No.: US 11,401,255 B2
(45) Date of Patent: Aug. 2, 2022

(54) SMALL MOLECULE ACTIVATORS OF PARKIN ENZYME FUNCTION

(71) Applicant: Mayo Foundation for Medical Education and Research, Rochester, MN (US)

(72) Inventors: Wolfdieter Springer, Neptune Beach, FL (US); Fabienne C. Fiesel, Neptune Beach, FL (US); Thomas R. Caulfield, Jacksonville, FL (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 244 days.

(21) Appl. No.: 16/321,208
(22) PCT Filed: Jul. 28, 2017
(86) PCT No.: PCT/US2017/044432
§ 371 (c)(1),
(2) Date: Jan. 28, 2019
(87) PCT Pub. No.: WO2018/023029
PCT Pub. Date: Feb. 1, 2018

(65) Prior Publication Data
US 2019/0169158 A1    Jun. 6, 2019

Related U.S. Application Data
(60) Provisional application No. 62/367,870, filed on Jul. 28, 2016.

(51) Int. Cl.
| C07D 401/04 | (2006.01) |
| C07D 401/12 | (2006.01) |
| C07D 213/56 | (2006.01) |
| C07D 233/64 | (2006.01) |
| C07D 235/16 | (2006.01) |
| C07D 257/04 | (2006.01) |
| C07D 403/12 | (2006.01) |
| C07D 403/14 | (2006.01) |
| C07D 409/14 | (2006.01) |
| C07D 413/12 | (2006.01) |

(Continued)

(52) U.S. Cl.
CPC ............ *C07D 401/04* (2013.01); *A61P 25/00* (2018.01); *A61P 25/16* (2018.01); *A61P 35/00* (2018.01); *C07D 213/56* (2013.01); *C07D 233/64* (2013.01); *C07D 235/16* (2013.01); *C07D 257/04* (2013.01); *C07D 401/12* (2013.01); *C07D 403/12* (2013.01); *C07D 403/14* (2013.01); *C07D 409/14* (2013.01); *C07D 413/12* (2013.01); *C07D 413/14* (2013.01); *C07D 417/14* (2013.01); *C07D 471/04* (2013.01); *C07D 471/10* (2013.01); *C07D 487/04* (2013.01); *C07D 498/04* (2013.01); *C12N 9/93* (2013.01); *C12Y 603/02019* (2013.01)

(58) Field of Classification Search
CPC .. C07D 213/56; C07D 401/04; C07D 233/64; C07D 401/12; C07D 235/16; C07D 257/04; C07D 403/12; C07D 403/14; C07D 409/14; C07D 413/12; C07D 413/14; C07D 417/14; C07D 471/04; C07D 471/10; C07D 487/04; C07D 498/04; C12N 9/93; C12Y 603/02019
See application file for complete search history.

(56) References Cited

U.S. PATENT DOCUMENTS

| 4,154,945 | A | * | 5/1979 | Brookes | ............... | C07D 249/08 |
| | | | | | | 548/334.1 |
| 2013/0231327 | A1 | | 9/2013 | Schunk et al. | | |
| 2015/0183801 | A1 | | 7/2015 | Furet et al. | | |
| 2016/0160205 | A1 | | 6/2016 | Johnston | | |

FOREIGN PATENT DOCUMENTS

| RU | 2322440 C1 * | 4/2008 |
| WO | WO 2009/075874 | 6/2009 |

OTHER PUBLICATIONS

Razdan, B., et al. "Synthesis of Some New Derivatives of 2-Methyl Imidazole." Indian Journal of Heterocyclic Chemistry. (Jan.-Mar. 2005), vol. 14, pp. 253-254. (Year: 2005).*

(Continued)

*Primary Examiner* — Timothy R Rozof
(74) *Attorney, Agent, or Firm* — Fish & Richardson P.C.

(57) ABSTRACT

The present disclosure relates to compounds for activating the enzymatic activity of an E3 ubiquitin ligase and methods for treating a disease or disorder in a subject with diminished E3 ubiquitin ligase enzymatic activity. In some embodiments, the present disclosure provides a compound of Formula (I) or a compound of Formula (II) or pharmaceutically acceptable salts thereof.

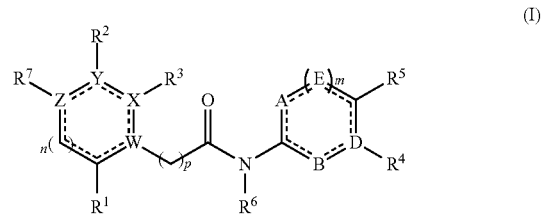

(I)

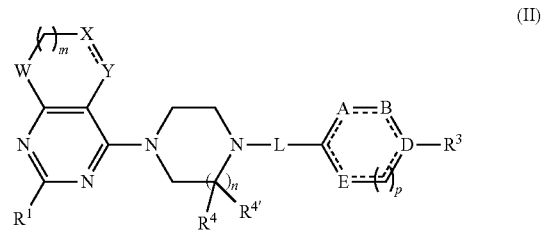

(II)

22 Claims, 43 Drawing Sheets

(51) Int. Cl.

| | | |
|---|---|---|
| C07D 413/14 | (2006.01) | |
| C07D 417/14 | (2006.01) | |
| C07D 471/04 | (2006.01) | |
| C07D 471/10 | (2006.01) | |
| C07D 487/04 | (2006.01) | |
| C07D 498/04 | (2006.01) | |
| C12N 9/00 | (2006.01) | |
| A61P 25/00 | (2006.01) | |
| A61P 25/16 | (2006.01) | |
| A61P 35/00 | (2006.01) | |

(56) References Cited

OTHER PUBLICATIONS

Mantu et al Journal of Enzyme Inhibition and Medicinal Chemistry 2016, 31, 96-103. (Year: 2016).*
Mishra et al Letters in Drug Design & Discovery, 2012, 9, 402-408. (Year: 2012).*
Caulfield et al., "Activation of the E3 ubiquitin ligase Parkin," Biochem. Soc. Trans., 43(2):269-274, Apr. 2015.
Caulfield et al., "Phosphorylation by PINK1 releases the UBL domain and initializes the conformational opening of the E3 ubiquitin ligase Parkin," PLoS Comput. Biol., 10(11):e 1003935, Nov. 2014.
Chavignon et al., "Pyrrolization processes of vinyl substituted imidazo [1, 2-a] pyridine, pyrimidine and 1,8-naphthyridine," J. Heterocycl. Chem., 29(4):691-7, Jul. 1992.
Dawson and Dawson, "Parkin plays a role in sporadic Parkinson's disease," Neurodegener. Dis., 13(2-3):69-71, Sep. 2013.
Fiesel et al., "A specific subset of E2 ubiquitin-conjugating enzymes regulate Parkin activation and mitophagy differently," J. Cell Sci., 127(Pt 16):3488-3504, Aug. 2014.
Fujikawa et al., "Relationships between structure and high-throughput screening permeability of diverse drugs with artificial membranes: application to prediction of Caco-2 cell permeability," Bioorg. Med. Chem., 13(15):4721-4732, Aug. 2005.
Geisler et al., "PINK1/Parkin-mediated mitophagy is dependent on VDAC1 and p62/SQSTMl,"Nat. Cell Biol., 12(2):119-131, Feb. 2010.
Iguchi et al., "Parkin-catalyzed ubiquitin-ester transfer is triggered by PINK1-dependent phosphorylation," J. Biol. Chem., 288(30):22019-22032, Jul. 2013.
International Search Report & Written Opinion in International Application No. PCT/US2017/044432 dated Nov. 29, 2017.
Kane et al., "PINK1 phosphorylates ubiquitin to activate Parkin E3 ubiquitin ligase activity," J. Cell Biol,, 205(2): 143-153, Apr. 2014.
Kazlauskaite et al., "Parkin is activated by PINK1-dependent phosphorylation of ubiquitin at Ser65," Biochem. J., 460(1):127-141, May 2014.
Kazlauskaite et al., "Phosphorylation of Parkin at Serine65 is essential for activation: elaboration of a Miro1 substrate-based assay of Parkin E3 ligase activity," Open Biol., 4:130213, Mar. 2014.
Kitada et al., "Mutations in the parkin gene cause autosomal recessive juvenile parkinsonism," Nature, 392(6676):605-608, Apr. 1998.
Koyano et al., "Ubiquitin is phosphorylated by PINK1 to activate parkin," Nature 510(7503):162-166, Jun. 2014.
Lau et al., "Evaluation of a novel in vitro Caco-2 hepatocyte hybrid system for predicting in vivo oral bioavailability," Drug Metab. Dispos., 32(9):937-942, Sep. 2004.
LaVoie et al., "Dopamine covalently modifies and functionally inactivates parkin," Nat. Med., 11(11):1214-1221, Nov. 2005.
LaVoie et al., "The effects of oxidative stress on parkin and other E3 ligases," J. Neurochem., 103(6):2354-2368, Dec. 2007.
Li et al., "Comparison of inhibitory effects of the proton pump-inhibiting drugs omeprazole, esomeprazole, lansoprazole, pantoprazole, and rabeprazole on human cytochrome P450 activities," Drug Metab. Dispos., 32(8):821-827, Aug. 2004.

McMillian et al., "An improved resazurin-based cytotoxicity assay for hepatic cells," Cell Biol. Toxicol., 18(3):157-173, 2002.
Montalbetti et al., "Amide bond formation and peptide coupling," Tetrahedron, 61(46):10827, Nov. 2005.
Mulvihill et al., "Discovery of OSI-906: a selective and orally efficacious dual inhibitor of the IGF-1 receptor and insulin receptor," Future Med. Chem., 1(6):1153-1171, Sep. 2009.
Narendra et al., "Parkin is recruited selectively to impaired mitochondria and promotes their autophagy," J. Cell Biol., 183(5):795-803, Dec. 2008.
Niwa et al., "Effect of antifungal drugs on cytochrome P450 (CYP) 2C9, CYP2C19, and CYP3A4 activities in human liver microsomes," Biol. Pharm. Bull., 28(9):1805-1808, 2005.
Okatsu et al., "Phosphorylated ubiquitin chain is the genuine Parkin receptor," J. Cell Biol., 209:111-128, Apr. 2015.
Ordureau et al., "Defining roles of PARKIN and ubiquitin phosphorylation by PINK1 in mitochondrial quality control using a ubiquitin replacement strategy," Proc. Natl. Acad. Sci. U.S.A., 112(21):6637-6642, May 2015.
Pubchem CID 1413 843 Create Date: Jul. 11, 2005 (Jul. 11, 2005); p. 3, compound listed.
Pubchem CID 21998776 Create Date: Dec. 5, 2007 (Dec. 5, 2007); p. 4, compound.
Pubchem CID 219990 Create Date: Mar. 26, 2005 (Mar. 26, 2005); p. 3, compound listed.
Pubchem CID 7168 Create Date: Mar. 26, 2005 (Mar. 26, 2005); p. 3, compound listed.
Richter et al., "Phosphorylation of OPTN by TBK1 enhances its binding to Ub chains and promotes selective autophagy of damaged mitochondria," Proc. Natl. Acad. Sci. U.S.A., 113(15):4039-4044, Apr. 2016.
Rubas et al., "Flux measurements across Caco-2 monolayers may predict transport in human large intestinal tissue," J. Pharm. Sci., 85(2):165-169, Feb. 1996.
Shiba-Fukushima et al., "PINK1-mediated phosphorylation of Parkin boosts Parkin activity in *Drosophila*," PLoS Genet., 10(6):el004391, Jun. 2014.
Valente et al., "Hereditary early-onset Parkinson's disease caused by mutations in PINK1," Science, 304(5674): 1158-1160, May 2004.
Vega-Avila and Pugsley, "An overview of colorimetric assay methods used to assess survival or proliferation of mammalian cells," Proc. West Pharmacol. Soc., 54:10-14, 2011.
Wenzel et al., "UBCH7 reactivity profile reveals parkin and HHARI to be RING/HECT hybrids," Nature, 474(7349): 105-108, Jun. 2011.
Wong et al., "Relative sensitivity of parkin and other cysteine-containing enzymes to stress-induced solubility alterations," J. Biol. Chem., 282(16):12310-12318, Apr. 2007.
Yamano and Youle, "PINK1 is degraded through the N-end rule pathway," Autophagy, 9(11):1758-1769, Nov. 2013.
Zheng et al., "Parkin mitochondrial translocation is achieved through a novel catalytic activity coupled mechanism," Cell Res., 23(7):886-897, Jul. 2013.
Extended European Search Report in European Application No. 17835361.1, dated Jan. 17, 2020, 10 pages.
Ganguly and Razdan, "Synthesis of some new derivatives of 2-methyl imidazole," Indian Journal of Heterocyclic Chemistry, 14(3):253-4, Jan. 2015.
Gore, "Microwave assisted synthesis and characterization of pharmaceutical important imidazole acetamides," Der Pharma Chemica, 8(1):185-87, 2016.
Grimmel et al., "Phosphazo compounds and their use in preparing amides," Journal of the American Chemical Society, 68(4):539-42, Apr. 1946.
Mishra et al., "Synthesis and anticonvulsant activity of some novel 2-methyl imidazole derivatives," Letters in Drug Design & Piscovery, 9(4):402-8, May 2012.
Ozkanli et al., "Synthesis of Some N-arylazole Acetamide Perivatives and Their Anticonvulsant and Antimicrobial Activities," Arzneimit-telforschung, 44(8):920-4, Aug. 1994.

(56) References Cited

OTHER PUBLICATIONS

Pubchem CID 1240941-90-6, "N-(4-phenoxyphenyl)-1H-imidazole-1 acetamide," Create Pate: Sep. 14, 2010 (Sep. 14, 2010); p. 1, compound listed.
Schiebel et al., "One question, multiple answers: biochemical and biophysical screening methods retrieve deviating fragment hit lists," ChemMedChem, 10(9):1511-21, Sep. 2015.

* cited by examiner

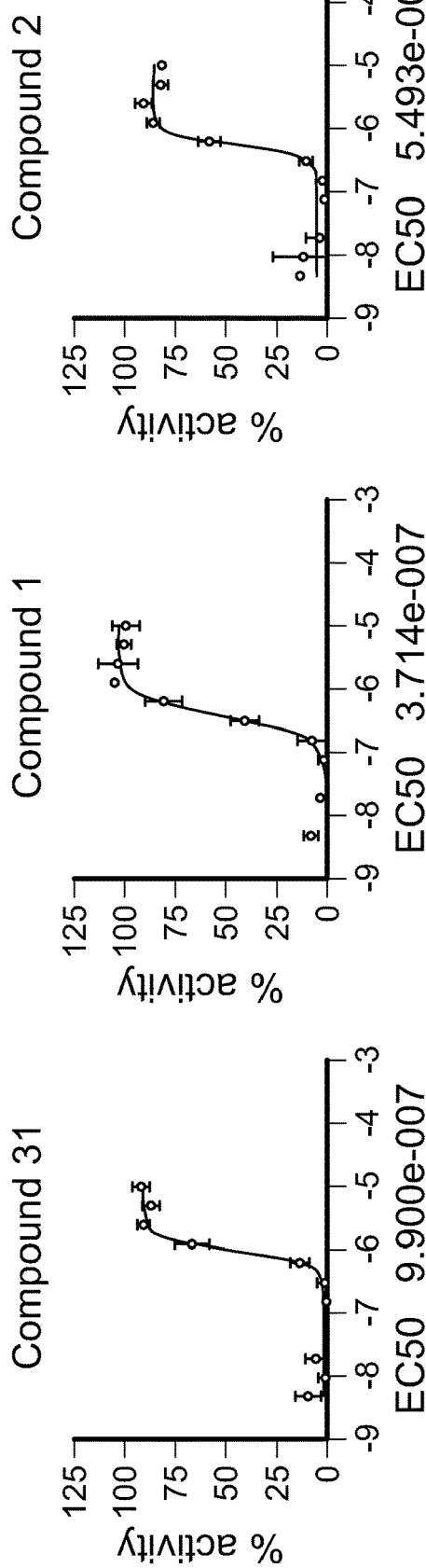
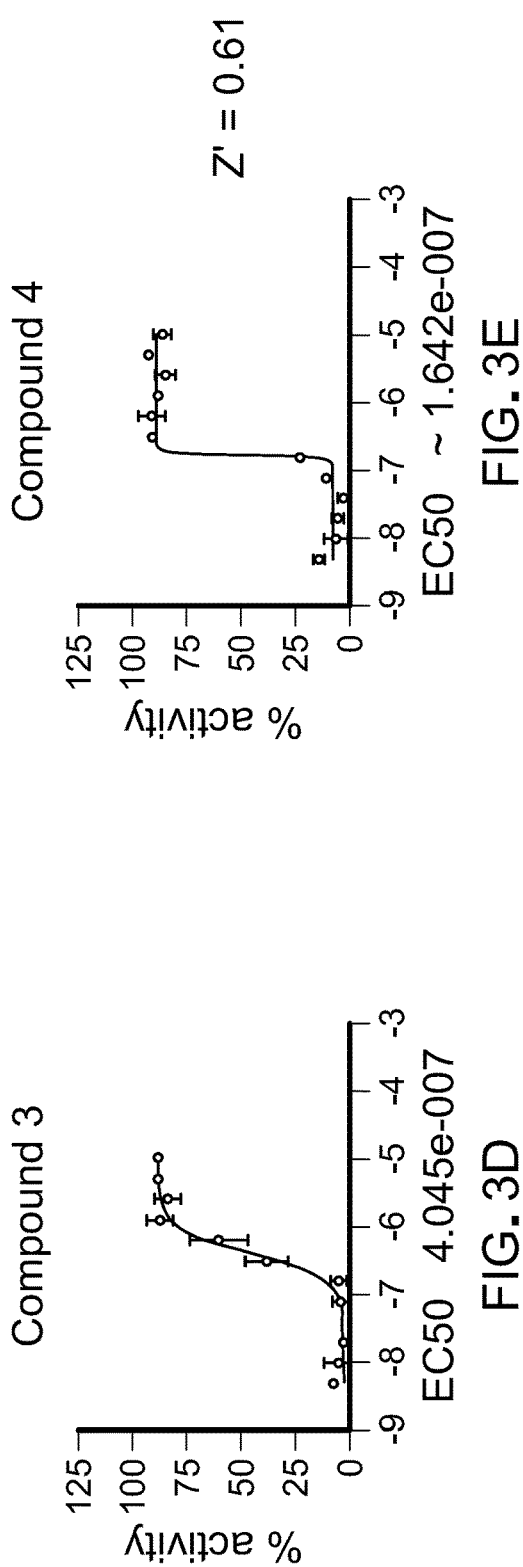

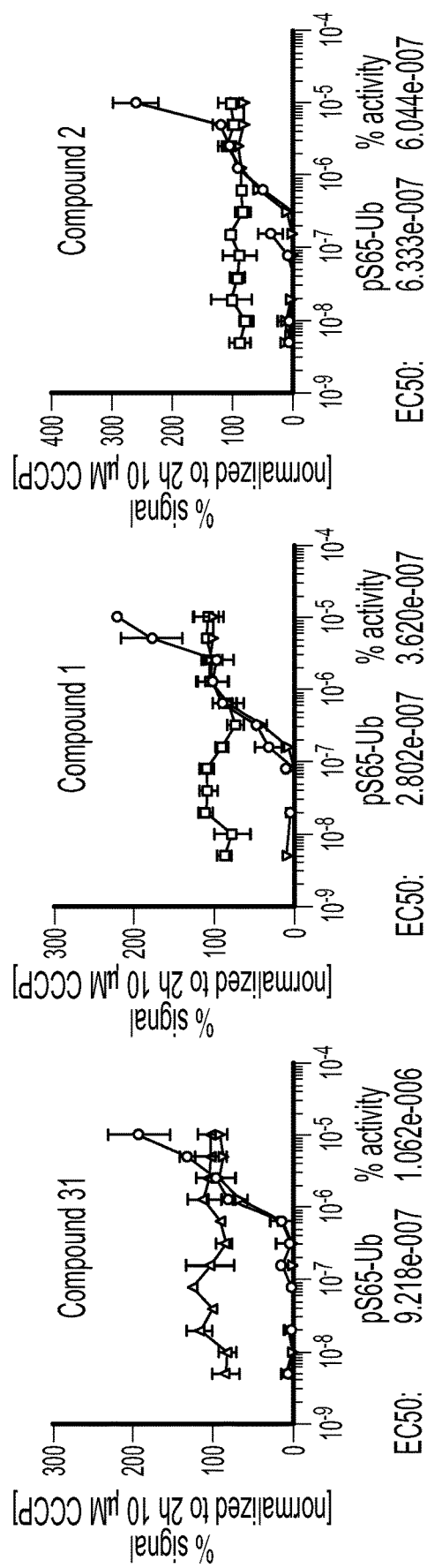
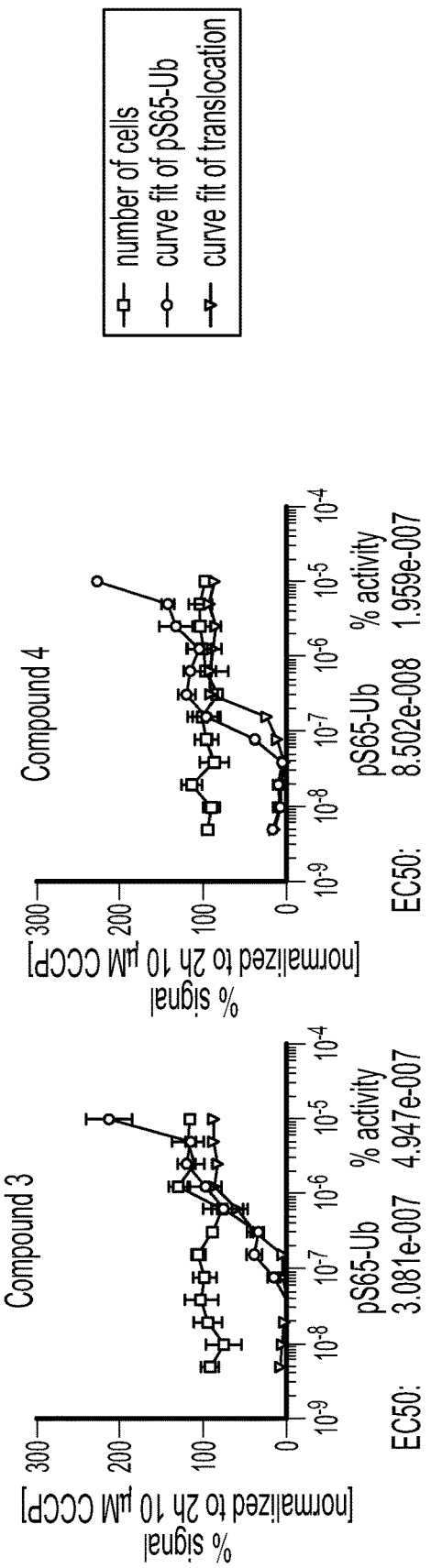
FIG. 4A  FIG. 4B  FIG. 4C
FIG. 4D  FIG. 4E

| Cmpd | ~EC50 (nM) | CNS | mol MW | SASA | logPo/w | logS | log hERG | predCaco | logBB | PSA |
|---|---|---|---|---|---|---|---|---|---|---|
| 1 | 362 | 0 | 331.416 | 646.967 | 4.626 | -5.948 | -6.356 | 2173.005 | -0.384 | 52.023 |
| 2 | 604 | 0 | 319.405 | 638.944 | 4.66 | -5.641 | -6.537 | 2881.505 | -0.31 | 48.893 |
| 3 | 495 | 0 | 289.395 | 580.556 | 3.354 | -4.37 | -5.414 | 1970.241 | -0.379 | 52.562 |
| 4 | 196 | 0 | 354.51 | 659.894 | 4.539 | -5.809 | -4.383 | 1782.156 | -0.484 | 60.704 |
| 5 | ~2000 | 0 | 321.381 | 622.982 | 3.078 | -4.519 | -6.004 | 728.418 | -0.928 | 83.337 |
| 6 | ~2000 | 0 | 311.77 | 593.698 | 3.889 | -5.061 | -6.485 | 1966.384 | -0.279 | 52.566 |
| 8 | ~5000 | 0 | 313.399 | 650.858 | 3.853 | -5.23 | -6.117 | 1968.504 | -0.575 | 59.602 |
| 9 | ~5000 | 1 | 332.404 | 631.94 | 3.358 | -3.688 | -6.938 | 428.621 | -0.129 | 56.762 |
| 10 | ~5000 | 0 | 335.448 | 632.745 | 4.197 | -5.672 | -5.52 | 1946.314 | -0.348 | 52.638 |
| 11 | ~5000 | 0 | 354.41 | 621.781 | 4.078 | -4.952 | -6.472 | 1574.573 | -0.468 | 61.336 |
| 12 | ~5000 | 0 | 345.323 | 610.145 | 4.277 | -5.505 | -6.381 | 1967.464 | -0.188 | 52.566 |
| 13 | ~5000 | 0 | 268.274 | 521.469 | 1.932 | -3.052 | -5.825 | 1409.472 | -0.443 | 74.248 |
| 14 | ~5000 | 0 | 293.324 | 581.625 | 3.414 | -4.265 | -6.579 | 1969.6 | -0.463 | 60.416 |
| 15 | ~5000 | 0 | 299.372 | 627.708 | 3.176 | -4.475 | -5.983 | 1969.067 | -0.561 | 59.967 |
| 16 | ~5000 | 0 | 318.334 | 619.295 | 1.858 | -5.22 | -6.683 | 408.722 | -1.289 | 86.204 |
| 17 | ~5000 | 0 | 257.335 | 565.547 | 3.18 | -4.614 | -5.53 | 1969.546 | -0.457 | 52.564 |
| 18 | ~5000 | 0 | 301.406 | 591.429 | 3.481 | -4.599 | -5.48 | 1884.114 | -0.386 | 52.586 |
| 19 | ~10000 | 0 | 291.352 | 591.226 | 3.989 | -4.95 | -6.377 | 2489.513 | -0.299 | 50.578 |
| 20 | ~10000 | 0 | 288.348 | 593.027 | 4.018 | -4.982 | -6.762 | 2296.836 | -0.343 | 48.616 |
| 31 | 1062 | 2 | 336.479 | 656.513 | 4.403 | -4.757 | -6.134 | 1812.036 | 0.701 | 27.508 |

FIG. 12

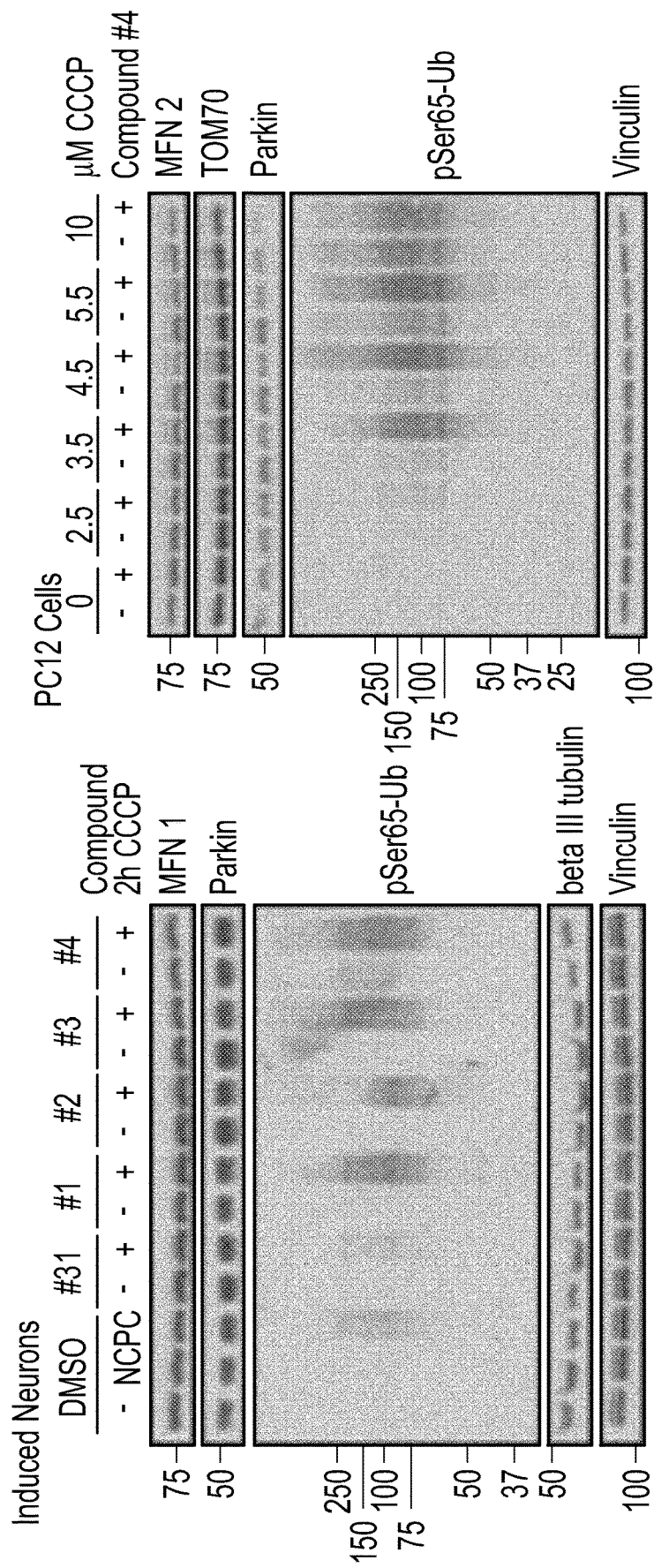

| Parameter | Parameter description | Range or Recommended Value | 1 | 2 | 3 | 4 | 6 |
|---|---|---|---|---|---|---|---|
| Compound # | Number of the compound. | | | | | | |
| Docking Score | Result from the docking onto the Parkin structure [empirical kcal/(mol*Å^2)] | | -10.096 | -10.12 | -10.047 | -10.093 | -8.992 |
| Activity (nM) | Result from the primary screening assay in dose response format. | | 371.4 | 549.3 | 404.5 | 164.2 | 2000 |
| RuleOfFive | Number of violations of Lipinski's rule of five. The rules are: mol_MW < 500, logPo/w <5 mol_MW 5, HBD ≤ 5, HBA ≤ 10. Compounds that satisfy these rules are considered drug-like. | 0-4 | 0 | 0 | 0 | 0 | 0 |
| RuleOfThree | Number of violations of Jorgensen's rule of three. The three rules are:, logS > -5.7, Caco-2 > 22 nm/s, primary metabolites < 7. | 0-3 | 1 | 0 | 0 | 1 | 0 |
| NRB | Number of non-trivial (not CX3), non-hindered (not alkene, amide, small ring) rotatable bonds. | 0 – 15 | 4 | 5 | 5 | 4 | 4 |
| #rtvFG | Number of reactive functional groups. | 0 - 2 | 0 | 0 | 0 | 0 | 0 |
| CNS | Predicted central nervous system activity on a –2 (inactive) to +2 (active) scale. | –2 to +2 | 0 | 0 | 0 | 0 | 0 |
| MW | molecular weight | 130.0 - 725.0 | 331.416 | 319.405 | 289.395 | 354.41 | 311.77 |
| dipole | Computed dipole moment of the molecule. | 1.0 - 12.5 | 6.243 | 7.977 | 6.638 | 3.473 | 7.502 |
| SASA | Total solvent accessible surface area (SASA) in square angstroms using a probe with a 1.4 Å. | 300.0 - 1000.0 | 646.967 | 638.944 | 580.556 | 668.804 | 593.698 |
| FOSA | Hydrophobic component of the SASA (saturated carbon and attached hydrogen). | 0.0 - 750.0 | 211.295 | 171.792 | 230.368 | 31.366 | 44.699 |
| FISA | Hydrophilic component of the SASA (SASA on N, O, H on heteroatoms, and carbonyl C). | 7.0 - 330.0 | 69.476 | 56.552 | 73.962 | 66.954 | 74.052 |
| PISA | π (carbon and attached hydrogen) component of the SASA. | 0.0 - 450.0 | 366.197 | 410.601 | 247.892 | 570.484 | 418.838 |
| WPSA | Weakly polar component of the SASA (halogens, P, and S). | 0.0 - 175.0 | 0 | 0 | 28.334 | 0 | 56.109 |
| volume | Total solvent-accessible volume in cubic angstroms using a probe with a 1.4 Å radius. | 500.0 - 2000.0 | 1127.59 | 1110.62 | 1000.19 | 1174.849 | 1005.08 |
| HBD | Estimated number of hydrogen bonds that would be donated by the solute to water molecules in an aqueous solution. Values are averages taken over a number of configurations. | 0.0 - 6.0 | 1 | 1 | 1 | 1 | 1 |
| HBA | Estimated number of hydrogen bonds that would be accepted by the solute from water molecules in an aqueous solution. Values are averages taken over a number of configurations. | 2.0 - 20.0 | 4 | 4 | 5 | 5 | 4.5 |

FIG. 17A

| Parameter | Parameter description | Range or Recommended Value | 1 | 2 | 3 | 4 | 6 |
|---|---|---|---|---|---|---|---|
| Compound # | Number of the compound. | | | | | | |
| dip^2/V | Square of the dipole moment divided by the molecular volume. This is the key term in the Kirkwood-Onsager equation for the free energy of solvation of a dipole with volume V. | 0.0 – 0.13 | 0.03456 | 0.0573 | 0.04406 | 0.010267 | 0.05599 |
| ACxDN^.5/SA | Index of cohesive interaction in solids. This term represents the relationship (HBA(SQRT(HBD))/(SA) ; see Bioorg. Med. Chem. Lett. 2000, 10, 1155. | 0.0 – 0.05 | 0.00618 | 0.00626 | 0.00861 | 0.007476 | 0.00758 |
| glob | Globularity descriptor, (4Πr2 )/(SASA), where r is the radius of a sphere with a volume equal to the molecular volume. Globularity is 1.0 for a spherical molecule. | 0.75 – 0.95 | 0.80981 | 0.81173 | 0.83312 | 0.805108 | 0.81733 |
| polrz | Predicted polarizability in cubic angstroms. | 13.0 – 70.0 | 39.901 | 39.004 | 33.03 | 43.743 | 35.501 |
| logPC16 | Predicted hexadecane/gas partition coefficient. | 4.0 - 18.0 | 11.978 | 12.035 | 10.156 | 13.861 | 11.575 |
| logPoct | Predicted octanol/gas partition coefficient. | 8.0 - 35.0 | 17.071 | 17.046 | 15.328 | 18.935 | 16.481 |
| logPw | Predicted water/gas partition coefficient. | 4.0 - 45.0 | 8.762 | 8.736 | 8.602 | 11.172 | 9.535 |
| logPo/w | Predicted octanol/water partition coefficient. | -2.0 – 6.5 | 4.626 | 4.66 | 3.354 | 4.761 | 3.889 |
| logS | Predicted aqueous solubility, log S. S in mol dm-3 is the concentration of the solute in a saturated solution that is in equilibrium with the crystalline solid. | -6.5 - 0.5 | -5.948 | -5.641 | -4.37 | -5.968 | -5.061 |
| Cl*logS | Conformation-independent predicted aqueous solubility, log S. S in mol dm-3 is the concentration of the solute in a saturated solution that is in equilibrium with the crystalline solid. | -6.5 - 0.5 | -5.345 | -5.121 | -3.777 | -5.799 | -4.774 |
| logHERG | Predicted IC50 value for blockage of HERG K+ channels. | concern below –5 | -6.356 | -6.537 | -5.414 | -7.406 | -6.485 |
| Caco-2 | Predicted apparent Caco-2 cell permeability in nm/sec. Caco-2 cells are a model for the gut-blood barrier. | >500 great | 2173.01 | 2881.51 | 1970.24 | 2296.009 | 1966.38 |
| logBB | Predicted brain/blood partition coefficient. | -3.0 - 1.2 | -0.384 | -0.31 | -0.379 | -0.366 | -0.279 |
| MDCK | Predicted apparent MDCK cell permeability in nm/sec. MDCK cells are considered to be a good mimic for the blood-brain barrier. | >500 great | 1144.65 | 1552.9 | 1472 | 1214.842 | 2085.14 |
| logKp | Predicted skin permeability, log Kp. | -8.0 - -1.0 | -1.126 | -0.635 | -1.529 | -0.36 | -1.025 |
| IP(eV) | PM3 calculated ionization potential (negative of HOMO energy). | 7.9 - 10.5 | 8.834 | 8.877 | 9.106 | 8.773 | 9.089 |
| EA(eV) | PM3 calculated electron affinity (negative of LUMO energy). | -0.9 - 1.7 | 0.598 | 0.621 | 0.77 | 0.667 | 0.642 |

FIG. 17B

| Parameter | Parameter description | Range or Recommended Value | 1 | 2 | 3 | 4 | 6 |
|---|---|---|---|---|---|---|---|
| Compound # | Number of the compound. | | | | | | |
| logKHSA | Prediction of binding to human serum albumin. | -1.5 - 1.5 | 0.735 | 0.647 | 0.161 | 0.661 | 0.306 |
| SAfluorine | Solvent-accessible surface area of fluorine atoms. | 0.0 - 100.0 | 0 | 0 | 0 | 0 | 0 |
| SAamideO | Solvent-accessible surface area of amide oxygen atoms. | 0.0 - 35.0 | 0 | 0 | 0 | 0 | 0 |
| PSA | Van der Waals surface area of polar nitrogen and oxygen atoms and carbonyl carbon atoms. | 7.0 - 200.0 | 52.023 | 48.893 | 52.562 | 58.219 | 52.566 |
| #NandO | Number of nitrogen and oxygen atoms. | 2 - 15 | 4 | 4 | 4 | 5 | 4 |
| #ringatoms | Number of atoms in rings. | | 21 | 17 | 11 | 23 | 17 |
| #in34 | Number of atoms in 3- or 4-membered rings. | | 0 | 0 | 0 | 0 | 0 |
| #in56 | Number of atoms in 5- or 6-membered rings. | | 21 | 17 | 11 | 23 | 17 |
| #noncon | Number of ring atoms not able to form conjugated aromatic systems (e.g. sp3 C). | | 4 | 0 | 0 | 0 | 0 |
| #nonHatm | Number of heavy atoms (nonhydrogen atoms). | | 25 | 24 | 20 | 27 | 22 |
| Jm | Predicted maximum transdermal transport rate, Kp x MW x S (μg cm-2 hr-1). Kp and S are obtained from the aqueous solubility and skin permeability, logKp and logS. | | 0.028 | 0.169 | 0.365 | 0.167 | 0.256 |
| #stars | Number of property or descriptor values that fall outside the 95% range of similar values for known drugs. Outlying descriptors and predicted properties are denoted with asterisks (*) in the .out file. A large number of stars suggests that a molecule is less drug-like than molecules with few stars. The following properties and descriptors are included in the determination of #stars: MW, dipole, IP, EA, SASA, FOSA, FISA, PISA, WPSA, PSA, volume, #rotor, donorHB, acceptHB, glob, QPpolrz, QPlogPC16, QPlogPoct, QPlogPw, QPlogPo/w, logS, QPlogKhsa, QPlogBB, #metabol | 0 - 5 | 0 | 0 | 0 | 1 | 0 |
| #amine | Number of non-conjugated amine groups. | 0 - 1 | 0 | 0 | 0 | 0 | 0 |
| #amidine | Number of amidine and guanidine groups. | 0 | 0 | 0 | 0 | 0 | 0 |
| #acid | Number of carboxylic acid groups. | 0 - 1 | 0 | 0 | 0 | 0 | 0 |
| #amide | Number of non-conjugated amide groups. | 0 - 1 | 0 | 0 | 0 | 0 | 0 |
| Ligand Efficiency | LE = -ΔG/#nonHatm or 1.4*(-logEC50[M])/#nonHatm ~ -ΔG/#nonHatm | > 0.3 | 0.36009 | 0.36518 | 0.44752 | 0.351795 | 0.36266 |

FIG. 17C

| Parameter | Parameter description | Range or Recommended Value | 8 | 9 | 10 | 11 | 12 |
|---|---|---|---|---|---|---|---|
| Compound # | Number of the compound. | | | | | | |
| Docking Score | Result from the docking onto the Parkin structure [empirical kcal/(mol*Å^2)] | | -8.907 | -8.864 | -8.856 | -8.848 | -8.807 |
| Activity (nM) | Result from the primary screening assay in dose response format. | | 5000 | 5000 | 5000 | 5000 | 5000 |
| RuleOfFive | Number of violations of Lipinski's rule of five. The rules are: mol_MW < 500, logPo/w <5 mol_MW 5, HBD ≤ 5, HBA ≤ 10. Compounds that satisfy these rules are considered drug-like. | 0-4 | 0 | 0 | 0 | 0 | 0 |
| RuleOfThree | Number of violations of Jorgensen's rule of three. The three rules are: logS >-5.7, Caco-2 > 22 nm/s , primary metabolites < 7. | 0-3 | 0 | 0 | 0 | 0 | 0 |
| NRB | Number of non-trivial (not CX3), non-hindered (not alkene, amide, small ring) rotatable bonds. | 0 – 15 | 6 | 5 | 3 | 4 | 4 |
| #rvFG | Number of reactive functional groups. | 0 - 2 | 0 | 0 | 0 | 0 | 0 |
| CNS | Predicted central nervous system activity on a –2 (inactive) to +2 (active) scale. | −2 to +2 | 0 | 1 | 0 | 0 | 0 |
| MW | molecular weight | 130.0 - 725.0 | 313.399 | 332.404 | 335.448 | 354.41 | 345.323 |
| dipole | Computed dipole moment of the molecule. | 1.0 - 12.5 | 5.221 | 5.152 | 4.683 | 5.036 | 3.258 |
| SASA | Total solvent accessible surface area (SASA) in square angstroms using a probe with a 1.4 Å. | 300.0 - 1000.0 | 650.858 | 631.94 | 632.745 | 621.781 | 610.145 |
| FOSA | Hydrophobic component of the SASA (saturated carbon and attached hydrogen). | 0.0 - 750.0 | 303.618 | 171.884 | 317.152 | 34.167 | 44.78 |
| FISA | Hydrophilic component of the SASA (SASA on N, O, H on heteroatoms, and carbonyl C). | 7.0 - 330.0 | 74.002 | 80.22 | 74.521 | 84.228 | 74.026 |
| PISA | Π(carbon and attached hydrogen) component of the SASA. | 0.0 - 450.0 | 273.238 | 379.837 | 241.071 | 503.386 | 398.895 |
| WPSA | Weakly polar component of the SASA (halogens, P, and S). | 0.0 - 175.0 | 0 | 0 | 0 | 0 | 92.444 |
| volume | Total solvent-accessible volume in cubic angstroms using a probe with a 1.4 Å radius. | 500.0 - 2000.0 | 1111.2 | 1114.68 | 1120.61 | 1128.56 | 1048.23 |
| HBD | Estimated number of hydrogen bonds that would be donated by the solute to water molecules in an aqueous solution. Values are averages taken over a number of configurations. | 0.0 - 6.0 | 1 | 1 | 1 | 1 | 1 |
| HBA | Estimated number of hydrogen bonds that would be accepted by the solute from water molecules in an aqueous solution. Values are averages taken over a number of configurations. | 2.0 - 20.0 | 5.25 | 5.5 | 4.5 | 5.5 | 4.5 |

FIG. 17D

| Parameter | Parameter description | Range or Recommended Value | 8 | 9 | 10 | 11 | 12 |
|---|---|---|---|---|---|---|---|
| Compound # | Number of the compound. | | | | | | |
| dip^2/V | Square of the dipole moment divided by the molecular volume. This is the key term in the Kirkwood-Onsager equation for the free energy of solvation of a dipole with volume V. | 0.0 – 0.13 | 0.02454 | 0.02381 | 0.01957 | 0.02247 | 0.01013 |
| ACxDN^.5/SA | Index of cohesive interaction in solids. This term represents the relationship (HBA(SQRT(HBD))/(SA) ; see Bioorg. Med. Chem. Lett. 2000, 10, 1155. | 0.0 – 0.05 | 0.00807 | 0.0087 | 0.00711 | 0.00885 | 0.00738 |
| glob | Globularity descriptor, (4Π r2 )/(SASA), where r is the radius of a sphere with a volume equal to the molecular volume. Globularity is 1.0 for a spherical molecule. | 0.75 – 0.95 | 0.79715 | 0.82273 | 0.82459 | 0.8431 | 0.8179 |
| polrz | Predicted polarizability in cubic angstroms. | 13.0 – 70.0 | 37.073 | 38.872 | 39.069 | 41.25 | 37.037 |
| logPC16 | Predicted hexadecane/gas partition coefficient. | 4.0 - 18.0 | 11.199 | 12.028 | 11.067 | 13.078 | 10.868 |
| logPoct | Predicted octanol/gas partition coefficient. | 8.0 - 35.0 | 16.368 | 17.462 | 16.755 | 18.61 | 16.549 |
| logPw | Predicted water/gas partition coefficient. | 4.0 - 45.0 | 8.96 | 10.148 | 8.624 | 11.212 | 9.451 |
| logPo/w | Predicted octanol/water partition coefficient. | -2.0 – 6.5 | 3.853 | 3.358 | 4.197 | 4.078 | 4.277 |
| logS | Predicted aqueous solubility, log S. S in mol dm-3 is the concentration of the solute in a saturated solution that is in equilibrium with the crystalline solid. | -6.5 - 0.5 | -5.23 | -3.688 | -5.672 | -4.952 | -5.505 |
| CI*logS | Conformation-independent predicted aqueous solubility, log S. S in mol dm-3 is the concentration of the solute in a saturated solution that is in equilibrium with the crystalline solid. | -6.5 - 0.5 | -4.129 | -3.802 | -4.843 | -5.602 | -5.452 |
| logHERG | Predicted IC50 value for blockage of HERG K+ channels. | concern below –5 | -6.117 | -6.938 | -5.52 | -6.472 | -6.381 |
| Caco-2 | Predicted apparent Caco-2 cell permeability in nm/sec. Caco-2 cells are a model for the gut-blood barrier. | >500 great | 1968.5 | 428.621 | 1946.31 | 1574.57 | 1967.46 |
| logBB | Predicted brain/blood partition coefficient. | -3.0 - 1.2 | -0.575 | -0.129 | -0.348 | -0.468 | -0.188 |
| MDCK | Predicted apparent MDCK cell permeability in nm/sec. MDCK cells are considered to be a good mimic for the blood-brain barrier. | >500 great | 1028.67 | 219.051 | 1016.14 | 808.09 | 3299.41 |
| logKp | Predicted skin permeability, log Kp. | -8.0 - -1.0 | -1.345 | -3.242 | -1.756 | -0.915 | -1.095 |
| IP(eV) | PM3 calculated ionization potential (negative of HOMO energy). | 7.9 - 10.5 | 8.817 | 8.203 | 9.053 | 8.851 | 9.458 |
| EA(eV) | PM3 calculated electron affinity (negative of LUMO energy). | -0.9 - 1.7 | 0.249 | 0.398 | 0.292 | 0.628 | 0.793 |

FIG. 17E

| Parameter | Parameter description | Range or Recommended Value | 8 | 9 | 10 | 11 | 12 |
|---|---|---|---|---|---|---|---|
| Compound # | Number of the compound. | | 8 | 9 | 10 | 11 | 12 |
| logKHSA | Prediction of binding to human serum albumin. | -1.5 - 1.5 | 0.35 | 0.363 | 0.664 | 0.452 | 0.423 |
| SAfluorine | Solvent-accessible surface area of fluorine atoms. | 0.0 - 100.0 | 0 | 0 | 0 | 0 | 92.444 |
| SAamideO | Solvent-accessible surface area of amide oxygen atoms. | 0.0 - 35.0 | 0 | 0 | 0 | 0 | 0 |
| PSA | Van der Waals surface area of polar nitrogen and oxygen atoms and carbonyl carbon atoms. | 7.0 - 200.0 | 59.602 | 56.762 | 52.638 | 61.336 | 52.566 |
| #NandO | Number of nitrogen and oxygen atoms. | 2 - 15 | 5 | 5 | 4 | 5 | 4 |
| #ringatoms | Number of atoms in rings. | | 17 | 20 | 21 | 23 | 17 |
| #in34 | Number of atoms in 3- or 4-membered rings. | | 0 | 0 | 0 | 0 | 0 |
| #in56 | Number of atoms in 5- or 6-membered rings. | | 17 | 20 | 21 | 23 | 17 |
| #noncon | Number of ring atoms not able to form conjugated aromatic systems (e.g. sp3 C). | | 6 | 2 | 10 | 0 | 0 |
| #nonHatm | Number of heavy atoms (nonhydrogen atoms). | | 23 | 25 | 25 | 27 | 25 |
| Jm | Predicted maximum transdermal transport rate, Kp x MW x S (μg cm-2 hr-1). Kp and S are obtained from the aqueous solubility and skin permeability, logKp and logS. | | 0.083 | 0.034 | 0.013 | 0.482 | 0.086 |
| #stars | Number of property or descriptor values that fall outside the 95% range of similar values for known drugs. Outlying descriptors and predicted properties are denoted with asterisks (*) in the .out file. A large number of stars suggests that a molecule is less drug-like than molecules with few stars. The following properties and descriptors are included in the determination of #stars: MW, dipole, IP, EA, SASA, FOSA, FISA, PISA, WPSA, PSA, volume, #rotor, donorHB, accptHB, glob, QPpolrz, QPlogPC16, QPlogPoct, QPlogPw, QPlogPo/w, logS, QPLogKhsa, QPlogBB, #metabol | 0 - 5 | 0 | 0 | 0 | 1 | 0 |
| #amine | Number of non-conjugated amine groups. | 0 - 1 | 0 | 1 | 0 | 0 | 0 |
| #amidine | Number of amidine and guanidine groups. | 0 | 0 | 0 | 0 | 0 | 0 |
| #acid | Number of carboxylic acid groups. | 0 - 1 | 0 | 0 | 0 | 0 | 0 |
| #amide | Number of non-conjugated amide groups. | 0 - 1 | 0 | 0 | 0 | 0 | 0 |
| Ligand Efficiency | LE = -ΔG/#nonHatm or 1.4*(-logEC50[M])/#nonHatm ~ -ΔG/#nonHatm | > 0.3 | 0.32267 | 0.29686 | 0.29686 | 0.27487 | 0.29686 |

FIG. 17F

| Parameter | Parameter description | Range or Recommended Value | 14 | 15 | 16 | 17 | 18 |
|---|---|---|---|---|---|---|---|
| Compound # | Number of the compound. | | 14 | 15 | 16 | 17 | 18 |
| Docking Score | Result from the docking onto the Parkin structure [empirical kcal/(mol*Å^2)] | | -8.777 | -8.764 | -8.876 | -7.211 | -7.21 |
| Activity (nM) | Result from the primary screening assay in dose response format. | | 5000 | 5000 | 5000 | 5000 | 5000 |
| RuleOfFive | Number of violations of Lipinski's rule of five. The rules are: mol_MW < 500, logPo/w <5 mol_MW 5, HBD ≤ 5, HBA ≤ 10. Compounds that satisfy these rules are considered drug-like. | 0-4 | 0 | 0 | 0 | 0 | 0 |
| RuleOfThree | Number of violations of Jorgensen's rule of three. The three rules are: logS > -5.7, Caco-2 > 22 nm/s, primary metabolites < 7. | 0-3 | 0 | 0 | 0 | 0 | 0 |
| NRB | Number of non-trivial (not CX3), non-hindered (not alkene, amide, small ring) rotatable bonds. | 0 – 15 | 5 | 6 | 6 | 5 | 5 |
| #rvFG | Number of reactive functional groups. | 0 - 2 | 0 | 0 | 0 | 0 | 0 |
| CNS | Predicted central nervous system activity on a –2 (inactive) to +2 (active) scale. | –2 to +2 | 0 | 0 | -2 | 0 | 0 |
| MW | molecular weight | 130.0 - 725.0 | 293.324 | 299.372 | 318.334 | 257.335 | 301.406 |
| dipole | Computed dipole moment of the molecule. | 1.0 - 12.5 | 5.844 | 7.206 | 6.856 | 6.146 | 2.27 |
| SASA | Total solvent accessible surface area (SASA) in square angstroms using a probe with a 1.4 Å. | 300.0 - 1000.0 | 581.625 | 627.708 | 619.295 | 565.547 | 591.429 |
| FOSA | Hydrophobic component of the SASA (saturated carbon and attached hydrogen). | 0.0 - 750.0 | 44.688 | 284.36 | 44.691 | 235.672 | 234.611 |
| FISA | Hydrophilic component of the SASA (SASA on N, O, H on heteroatoms, and carbonyl C). | 7.0 - 330.0 | 73.977 | 73.989 | 145.995 | 73.978 | 76.009 |
| PISA | Π (carbon and attached hydrogen) component of the SASA. | 0.0 - 450.0 | 462.96 | 269.359 | 428.609 | 255.896 | 243.475 |
| WPSA | Weakly polar component of the SASA (halogens, P, and S). | 0.0 - 175.0 | 0 | 0 | 0 | 0 | 37.334 |
| volume | Total solvent-accessible volume in cubic angstroms using a probe with a 1.4 Å radius. | 500.0 - 2000.0 | 987.461 | 1066.62 | 1052.45 | 953.397 | 1018.48 |
| HBD | Estimated number of hydrogen bonds that would be donated by the solute to water molecules in an aqueous solution. Values are averages taken over a number of configurations. | 0.0 - 6.0 | 1 | 1 | 1 | 1 | 1 |
| HBA | Estimated number of hydrogen bonds that would be accepted by the solute from water molecules in an aqueous solution. Values are averages taken over a number of configurations. | 2.0 - 20.0 | 5 | 6.2 | 6.5 | 4.5 | 5 |

FIG. 17G

| Parameter | Parameter description | Range or Recommended Value | 14 | 15 | 16 | 17 | 18 |
|---|---|---|---|---|---|---|---|
| Compound # | Number of the compound. | | | | | | |
| dip^2/V | Square of the dipole moment divided by the molecular volume. This is the key term in the Kirkwood-Onsager equation for the free energy of solvation of a dipole with volume V. | 0.0 – 0.13 | 0.03458 | 0.04869 | 0.04466 | 0.03962 | 0.00506 |
| ACxDN^.5/SA | Index of cohesive interaction in solids. This term represents the relationship (HBA(SQRT(HBD))/(SA); see Bioorg. Med. Chem. Lett. 2000, 10, 1155. | 0.0 – 0.05 | 0.0086 | 0.00988 | 0.0105 | 0.00796 | 0.00845 |
| glob | Globularity descriptor, $(4\Pi r^2)/(SASA)$, where r is the radius of a sphere with a volume equal to the molecular volume. Globularity is 1.0 for a spherical molecule. | 0.75 – 0.95 | 0.82452 | 0.80429 | 0.80798 | 0.82835 | 0.82775 |
| polrz | Predicted polarizability in cubic angstroms. | 13.0 – 70.0 | 34.575 | 35.252 | 36.206 | 31.234 | 33.72 |
| logPC16 | Predicted hexadecane/gas partition coefficient. | 4.0 - 18.0 | 11.327 | 10.727 | 12.218 | 9.536 | 10.371 |
| logPoct | Predicted octanol/gas partition coefficient. | 8.0 - 35.0 | 15.914 | 16.587 | 17.654 | 14.214 | 15.068 |
| logPw | Predicted water/gas partition coefficient. | 4.0 - 45.0 | 10.058 | 9.813 | 11.661 | 8.118 | 8.615 |
| logPo/w | Predicted octanol/water partition coefficient. | -2.0 – 6.5 | 3.414 | 3.176 | 1.858 | 3.18 | 3.481 |
| logS | Predicted aqueous solubility, log S. S in mol dm-3 is the concentration of the solute in a saturated solution that is in equilibrium with the crystalline solid. | -6.5 - 0.5 | -4.265 | -4.475 | -5.22 | -4.614 | -4.599 |
| Cl*logS | Conformation-independent predicted aqueous solubility, log S. S in mol dm-3 is the concentration of the solute in a saturated solution that is in equilibrium with the crystalline solid. | -6.5 - 0.5 | -4.214 | -3.492 | -5.132 | -3.333 | -3.991 |
| logHERG | Predicted IC50 value for blockage of HERG K+ channels. | concern below –5 | -6.579 | -5.983 | -6.683 | -5.53 | -5.48 |
| Caco-2 | Predicted apparent Caco-2 cell permeability in nm/sec. Caco-2 cells are a model for the gut-blood barrier. | >500 great | 1969.6 | 1969.07 | 408.722 | 1969.55 | 1884.11 |
| logBB | Predicted brain/blood partition coefficient. | -3.0 - 1.2 | -0.463 | -0.561 | -1.289 | -0.457 | -0.386 |
| MDCK | Predicted apparent MDCK cell permeability in nm/sec. MDCK cells are considered to be a good mimic for the blood-brain barrier. | >500 great | 1029.29 | 1028.99 | 188.083 | 1029.26 | 1571.17 |
| logKp | Predicted skin permeability, log Kp. | -8.0 - -1.0 | -0.772 | -1.358 | -2.124 | -1.501 | -1.583 |
| IP(eV) | PM3 calculated ionization potential (negative of HOMO energy). | 7.9 - 10.5 | 9.092 | 9.059 | 9.299 | 9.064 | 9.146 |
| EA(eV) | PM3 calculated electron affinity (negative of LUMO energy). | -0.9 - 1.7 | 0.48 | 0.314 | 0.867 | 0.308 | 0.768 |

FIG. 17H

| Parameter | Parameter description | Range or Recommended Value | 14 | 15 | 16 | 17 | 18 |
|---|---|---|---|---|---|---|---|
| Compound # | Number of the compound. | | 14 | 15 | 16 | 17 | 18 |
| logKHSA | Prediction of binding to human serum albumin. | -1.5 - 1.5 | 0.123 | 0.045 | -0.05 | 0.13 | 0.207 |
| SAfluorine | Solvent-accessible surface area of fluorine atoms. | 0.0 - 100.0 | 0 | 0 | 0 | 0 | 0 |
| SAamideO | Solvent-accessible surface area of amide oxygen atoms. | 0.0 - 35.0 | 0 | 0 | 0 | 0 | 0 |
| PSA | Van der Waals surface area of polar nitrogen and oxygen atoms and carbonyl carbon atoms. | 7.0 - 200.0 | 60.416 | 59.967 | 86.204 | 52.564 | 52.586 |
| #NandO | Number of nitrogen and oxygen atoms. | 2 - 15 | 5 | 5 | 6 | 4 | 4 |
| #ringatoms | Number of atoms in rings. | | 17 | 16 | 17 | 11 | 16 |
| #in34 | Number of atoms in 3- or 4-membered rings. | | 0 | 0 | 0 | 0 | 0 |
| #in56 | Number of atoms in 5- or 6-membered rings. | | 17 | 16 | 17 | 11 | 16 |
| #noncon | Number of ring atoms not able to form conjugated aromatic systems (e.g. sp3 C). | | 0 | 5 | 0 | 0 | 5 |
| #nonHatm | Number of heavy atoms (nonhydrogen atoms). | | 22 | 22 | 24 | 19 | 21 |
| Jm | Predicted maximum transdermal transport rate, Kp x MW x S (μg cm-2 hr-1). Kp and S are obtained from the aqueous solubility and skin permeability, logKp and logS. | | 2.696 | 0.44 | 0.014 | 0.564 | 0.198 |
| #stars | Number of property or descriptor values that fall outside the 95% range of similar values for known drugs. Outlying descriptors and predicted properties are denoted with asterisks (*) in the .out file. A large number of stars suggests that a molecule is less drug-like than molecules with few stars. The following properties and descriptors are included in the determination of #stars: MW, dipole, IP, EA, SASA, FOSA, FISA, PISA, WPSA, PSA, volume, #rotor, donorHB, accptHB, glob, QPpolrz, QPlogPC16, QPlogPoct, QPlogPw, QPlogPo/w, logS, QPLogKhsa, QPlogBB, #metabol | 0 - 5 | 1 | 0 | 0 | 0 | 0 |
| #amine | Number of non-conjugated amine groups. | 0 - 1 | 0 | 0 | 0 | 0 | 0 |
| #amidine | Number of amidine and guanidine groups. | 0 | 0 | 0 | 0 | 0 | 0 |
| #acid | Number of carboxylic acid groups. | 0 - 1 | 0 | 0 | 0 | 0 | 0 |
| #amide | Number of non-conjugated amide groups. | 0 - 1 | 0 | 0 | 0 | 0 | 0 |
| Ligand Efficiency | LE = -ΔG/#nonHatm or 1.4*(-logEC50[M])/#nonHatm ~ -ΔG/#nonHatm | > 0.3 | 0.33734 | 0.33734 | 0.30923 | 0.3906 | 0.3534 |

FIG. 17I

| Parameter | Parameter description | Range or Recommended Value | 19 | 20 | 29 | 30 | 31 |
|---|---|---|---|---|---|---|---|
| Compound # | Number of the compound. | | | | | | |
| Docking Score | Result from the docking onto the Parkin structure [empirical kcal/(mol*Å^2)] | | -7.206 | -8.503 | -8.99 | -8.801 | -9.832 |
| Activity (nM) | Result from the primary screening assay in dose response format. | | 10000 | 10000 | 2000 | 5000 | 990 |
| RuleOfFive | Number of violations of Lipinski's rule of five. The rules are: mol_MW < 500, logPo/w <5 mol_MW 5, HBD ≤ 5, HBA ≤ 10. Compounds that satisfy these rules are considered drug-like. | 0-4 | 0 | 0 | 1 | 0 | 0 |
| RuleOfThree | Number of violations of Jorgensen's rule of three. The three rules are: logS >-5.7, Caco-2 > 22 nm/s, primary metabolites < 7. | 0-3 | 0 | 0 | 1 | 0 | 0 |
| NRB | Number of non-trivial (not CX3), non-hindered (not alkene, amide, small ring) rotatable bonds. | 0 – 15 | 4 | 4 | 4 | 4 | 2 |
| #rvFG | Number of reactive functional groups. | 0 - 2 | 0 | 0 | 0 | 0 | 0 |
| CNS | Predicted central nervous system activity on a –2 (inactive) to +2 (active) scale. | –2 to +2 | 0 | 0 | 0 | 0 | 2 |
| MW | molecular weight | 130.0 - 725.0 | 291.352 | 288.348 | 353.423 | 291.352 | 336.479 |
| dipole | Computed dipole moment of the molecule. | 1.0 - 12.5 | 4.895 | 4.118 | 9.108 | 5.596 | 2.404 |
| SASA | Total solvent accessible surface area (SASA) in square angstroms using a probe with a 1.4 Å. | 300.0 - 1000.0 | 591.226 | 593.027 | 666.31 | 586.509 | 656.513 |
| FOSA | Hydrophobic component of the SASA (saturated carbon and attached hydrogen). | 0.0 - 750.0 | 110.651 | 42.813 | 10.246 | 114.766 | 435.329 |
| FISA | Hydrophilic component of the SASA (SASA on N, O, H on heteroatoms, and carbonyl C). | 7.0 - 330.0 | 63.249 | 66.938 | 69.07 | 83.292 | 14.197 |
| PISA | Π(carbon and attached hydrogen) component of the SASA. | 0.0 - 450.0 | 417.327 | 483.276 | 586.994 | 388.452 | 206.986 |
| WPSA | Weakly polar component of the SASA (halogens, P, and S). | 0.0 - 175.0 | 0 | 0 | 0 | 0 | 0 |
| volume | Total solvent-accessible volume in cubic angstroms using a probe with a 1.4 Å radius. | 500.0 - 2000.0 | 1010.27 | 1006.84 | 1174.95 | 1005.673 | 1177.576 |
| HBD | Estimated number of hydrogen bonds that would be donated by the solute to water molecules in an aqueous solution. Values are averages taken over a number of configurations. | 0.0 - 6.0 | 1 | 1 | 1 | 1 | 0 |
| HBA | Estimated number of hydrogen bonds that would be accepted by the solute from water molecules in an aqueous solution. Values are averages taken over a number of configurations. | 2.0 - 20.0 | 4 | 4 | 4 | 4.5 | 4.5 |

FIG. 17J

| Parameter | Parameter description | Range or Recommended Value | 19 | 20 | 29 | 30 | 31 |
|---|---|---|---|---|---|---|---|
| Compound # | Number of the compound. | | | | | | |
| dip^2/V | Square of the dipole moment divided by the molecular volume. This is the key term in the Kirkwood-Onsager equation for the free energy of solvation of a dipole with volume V. | 0.0 – 0.13 | 0.02372 | 0.01684 | 0.070601 | 0.031142 | 0.0049078 |
| ACxDN^.5/SA | Index of cohesive interaction in solids. This term represents the relationship (HBA(SQRT(HBD))/(SA), see Bioorg. Med. Chem. Lett. 2000, 10, 1155. | 0.0 – 0.05 | 0.00677 | 0.00675 | 0.006003 | 0.007673 | 0 |
| glob | Globularity descriptor, $(4\Pi r^2)/(SASA)$, where r is the radius of a sphere with a volume equal to the molecular volume. Globularity is 1.0 for a spherical molecule. | 0.75 – 0.95 | 0.82357 | 0.81921 | 0.808168 | 0.827678 | 0.8214495 |
| polrz | Predicted polarizability in cubic angstroms. | 13.0 – 70.0 | 35.694 | 36.186 | 43.905 | 35.234 | 41.665 |
| logPC16 | Predicted hexadecane/gas partition coefficient. | 4.0 - 18.0 | 11.155 | 11.604 | 13.99 | 11.055 | 10.715 |
| logPoct | Predicted octanol/gas partition coefficient. | 8.0 - 35.0 | 15.525 | 15.712 | 19.329 | 15.802 | 15.693 |
| logPw | Predicted water/gas partition coefficient. | 4.0 - 45.0 | 8.933 | 9.411 | 10.308 | 9.354 | 6.795 |
| logPo/w | Predicted octanol/water partition coefficient. | -2.0 – 6.5 | 3.989 | 4.018 | 5.188 | 3.537 | 4.403 |
| logS | Predicted aqueous solubility, log S. S in mol dm-3 is the concentration of the solute in a saturated solution that is in equilibrium with the crystalline solid. | -6.5 - 0.5 | -4.95 | -4.982 | -6.297 | -4.689 | -4.757 |
| Cl*logS | Conformation-independent predicted aqueous solubility, log S. S in mol dm-3 is the concentration of the solute in a saturated solution that is in equilibrium with the crystalline solid. | -6.5 - 0.5 | -4.555 | -4.554 | -6.173 | -4.365 | -3.459 |
| logHERG | Predicted IC50 value for blockage of HERG K+ channels. | concern below -5 | -6.377 | -6.762 | -7.435 | -6.173 | -6.134 |
| Caco-2 | Predicted apparent Caco-2 cell permeability in nm/sec. Caco-2 cells are a model for the gut-blood barrier. | >500 great | 2489.51 | 2296.84 | 2192.359 | 1607.106 | 1812.036 |
| logBB | Predicted brain/blood partition coefficient. | -3.0 - 1.2 | -0.299 | -0.343 | -0.383 | -0.488 | 0.701 |
| MDCK | Predicted apparent MDCK cell permeability in nm/sec. MDCK cells are considered to be a good mimic for the blood-brain barrier. | >500 great | 1325.88 | 1215.32 | 1155.673 | 826.151 | 1040.585 |
| logKp | Predicted skin permeability, log Kp. | -8.0 - -1.0 | -0.831 | -0.667 | -0.341 | -1.302 | -2.923 |
| IP(eV) | PM3 calculated ionization potential (negative of HOMO energy). | 7.9 - 10.5 | 8.856 | 8.701 | 9.025 | 9.207 | 8.892 |
| EA(eV) | PM3 calculated electron affinity (negative of LUMO energy). | -0.9 - 1.7 | 0.614 | 0.488 | 0.679 | 0.477 | 0.239 |

FIG. 17K

| Parameter | Parameter description | Range or Recommended Value | 19 | 20 | 29 | 30 | 31 |
|---|---|---|---|---|---|---|---|
| Compound # | Number of the compound. | | 19 | 20 | 29 | 30 | 31 |
| logKHSA | Prediction of binding to human serum albumin. | -1.5 - 1.5 | 0.42 | 0.409 | 0.865 | 0.312 | 0.748 |
| SAfluorine | Solvent-accessible surface area of fluorine atoms. | 0.0 - 100.0 | 0 | 0 | 0 | 0 | 0 |
| SAamideO | Solvent-accessible surface area of amide oxygen atoms. | 0.0 - 35.0 | 0 | 0 | 0 | 0 | 0 |
| PSA | Van der Waals surface area of polar nitrogen and oxygen atoms and carbonyl carbon atoms. | 7.0 - 200.0 | 50.578 | 48.616 | 51.763 | 52.604 | 27.508 |
| #NandO | Number of nitrogen and oxygen atoms. | 2 - 15 | 4 | 3 | 4 | 4 | 4 |
| #ringatoms | Number of atoms in rings. | | 17 | 18 | 23 | 17 | 23 |
| #in34 | Number of atoms in 3- or 4-membered rings. | | 0 | 0 | 0 | 0 | 0 |
| #in56 | Number of atoms in 5- or 6-membered rings. | | 17 | 18 | 23 | 17 | 23 |
| #noncon | Number of ring atoms not able to form conjugated aromatic systems (e.g. sp3 C). | | 0 | 0 | 0 | 0 | 9 |
| #nonHatm | Number of heavy atoms (nonhydrogen atoms). | | 22 | 22 | 27 | 22 | 25 |
| Jm | Predicted maximum transdermal transport rate, Kp x MW x S (μg cm−2 hr−1). Kp and S are obtained from the aqueous solubility and skin permeability, logKp and logS. | | 0.482 | 0.647 | 0.081 | 0.297 | 0.007 |
| #stars | Number of property or descriptor values that fall outside the 95% range of similar values for known drugs. Outlying descriptors and predicted properties are denoted with asterisks (*) in the .out file. A large number of stars suggests that a molecule is less drug-like than molecules with few stars. The following properties and descriptors are included in the determination of #stars: MW, dipole, IP, EA, SASA, FOSA, FISA, PISA, WPSA, PSA, volume, #rotor, donorHB, accptHB, glob, QPpolrz, QPlogPC16, QPlogPoct, QPlogPw, QPlogPo/w, logS, QPLogKhsa, QPlogBB, #metabol | 0 - 5 | 0 | 1 | 1 | 0 | 0 |
| #amine | Number of non-conjugated amine groups. | 0 - 1 | 0 | 0 | 0 | 0 | 1 |
| #amidine | Number of amidine and guanidine groups. | 0 | 0 | 0 | 0 | 0 | 0 |
| #acid | Number of carboxylic acid groups. | 0 - 1 | 0 | 0 | 0 | 0 | 0 |
| #amide | Number of non-conjugated amide groups. | 0 - 1 | 0 | 0 | 0 | 0 | 0 |
| Ligand Efficiency | LE = -ΔG/#nonHatm or 1.4*(-logEC50[M])/#nonHatm ~ -ΔG/#nonHatm | > 0.3 | 0.31818 | 0.31818 | 0.295502 | 0.337338 | 0.3362444 |

FIG. 17L

| Compound ID | Time, min | Analyte Peak Area Inc. 1 | Analyte Peak Area Inc. 2 | Analyte Peak Area, Mean | % Remaining, Mean | R | $K_{el}$, $min^{-1}$ | $t_{1/2}$, min | $Cl_{int}$, µl/min/mg | % Remaining without cofactor, Mean |
|---|---|---|---|---|---|---|---|---|---|---|
| Compound 31 | 0 | 1,14E+03 | 1,24E+03 | 1,19E+03 | 100 | 0,994 | 0,147 | 4,7 | 354,8 | 100 |
| | 7 | 4,99E+02 | 5,35E+02 | 5,17E+02 | 43 | | | | | |
| | 14 | 1,40E+02 | 1,63E+02 | 1,52E+02 | 13 | | | | | |
| | 22 | 6,46E+01 | 2,81E+01 | 4,64E+01 | 4 | | | | | 99 |
| | 40 | 5,61E+01 | 1,85E+01 | 3,73E+01 | 3 | | | | | |
| Compound 1 | 0 | 1,45E+05 | 1,43E+05 | 1,44E+05 | 100 | 0,991 | 0,012 | 59,0 | 28,3 | 100 |
| | 7 | 1,42E+05 | 1,36E+05 | 1,39E+05 | 97 | | | | | |
| | 14 | 1,30E+05 | 1,26E+05 | 1,28E+05 | 89 | | | | | |
| | 22 | 1,20E+05 | 1,20E+05 | 1,11E+05 | 77 | | | | | |
| | 40 | 8,73E+04 | 9,73E+04 | 9,23E+04 | 64 | | | | | 96 |

FIG. 19B

| Compound ID | Time, min | Analyte Peak Area Inc. 1 | Analyte Peak Area Inc. 2 | Analyte Peak Area, Mean | % Remaining, Mean | R | $K_{el}$, $min^{-1}$ | $t_{1/2}$, min | $Cl_{int}$, µl/min/mg | % Remaining without cofactor, Mean |
|---|---|---|---|---|---|---|---|---|---|---|
| Compound 4 | 0 | 2,22E+05 | 2,19E+05 | 2,21E+05 | 100 | 0,995 | 0,051 | 13,5 | 123,4 | 100 |
| | 7 | 1,75E+05 | 1,78E+05 | 1,77E+05 | 80 | | | | | |
| | 14 | 1,23E+05 | 1,34E+05 | 1,29E+05 | 58 | | | | | |
| | 22 | 7,93E+04 | 6,60E+04 | 7,27E+04 | 33 | | | | | |
| | 40 | 3,05E+04 | 3,06E+04 | 3,06E+04 | 14 | | | | | 95 |

SMALL MOLECULE ACTIVATORS OF PARKIN ENZYME FUNCTION

CROSS-REFERENCE TO RELATED APPLICATIONS

This application is a National Stage application under 35 U.S.C. § 371 of International Application No. PCT/US2017/044432, having an International Filing Date of Jul. 28, 2017, which claims priority to U.S. Provisional Application Ser. No. 62/367,870, filed on Jul. 28, 2016, each of which are incorporated by reference in their entireties.

TECHNICAL FIELD

The present disclosure relates to compounds for activating the enzymatic activity of an E3 ubiquitin ligase and methods for treating a disease or disorder in a subject with diminished E3 ubiquitin ligase enzymatic activity.

BACKGROUND

The enzymatic activity of the broadly protective E3 ubiquitin ligases and mitochondrial quality control is often lost or decreased in patients suffering from certain diseases or disorders, such as Parkinson's disease, and is diminished during aging and in many other age-related human disorders. As a result, dysfunctional mitochondria accumulate and eventually result in cell death.

The mitochondrial kinase PINK1 and the cytosolic E3 ubiquitin ligase Parkin together mediate the selective degradation of damaged mitochondria by autophagy (mitophagy) (Narendra et al. (2008) J. Cell Biol. 183:795-803; Geisler et al. (2010) Nat. Cell Biol. 12: 119-131). This crucial mitochondrial quality control pathway protects cells from the accumulation of harmful damaged mitochondria. While all cells are affected by mitochondrial damage, energy-demanding cells like neurons and muscle cells are especially vulnerable to failure of mitochondrial quality control. Loss-of function mutations of PINK1 and Parkin abrogate mitochondrial quality control and are associated with early-onset recessive Parkinson's disease (PD) (Kitada et al. (1998) Nature 392:605-608; Valente et al. (2004) Science 304:1158-1160). In addition, inactivation of Parkin has also been reported in sporadic, late-onset PD (Dawson et al. (2014) Neurodegener. Dis. 13:69-71; LaVoie et al. (2005) Nat. Med. 11:1214-1221; LaVoie et al. (2007) J. Neurochem. 103:2354-2368; Wong et al. (2007) J. Biol. Chem. 282:12310-12318). However, PINK1 and Parkin are conserved amongst all multicellular eukaryotes and are widely expressed across all tissues/cells. Given the presence of mitochondria in all cells and the need for such a stress-induced quality control pathway, selective clearance through mitophagy appears to be a fundamental, cytoprotective mechanism with far-reaching implications beyond PD. Thus activation of Parkin has been recognized as a potentially beneficial and broadly applicable new therapy for a wide-range of human diseases and aging.

SUMMARY

The foregoing and other aspects and embodiments of the disclosure can be more fully understood by reference to the following detailed description and claims.

The present application provides compounds of Formula I:

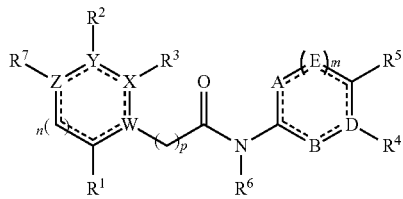

or a pharmaceutically acceptable salt thereof, wherein:
A is CH or O;
B is CH or N;
D is C or N;
E is CH or N;
W is C or N;
X is C or N;
Y is C or N;
Z is C or N;
$R^1$ is H, $C_{1-4}$ alkyl, phenyl, or $hetAr^1$;
$R^2$ is H;
$R^3$ is H;
or $R^2$ and $R^3$, together with Y and X, form a 6-membered cycloalkyl ring;
$R^7$ is H;
or, optionally, when n is 0, $R^1$ and $R^7$, together with the atoms to which they are attached form a 6-membered cycloalkyl ring;
$R^4$ is H, $C_{1-4}$ alkyl, halogen, $CF_3$, or phenyl;
$R^5$ is H, $C_{1-4}$ alkyl, $C_{4-10}$ cycloalkyl, phenyl optionally substituted with halogen, $(C_{1-3}$ alkyl)$O(C_{4-6}$ cycloalkyl), $O(C_{1-4}$ alkyl)$(C_{4-6}$ cycloalkyl), $S(C_{1-4}$ alkyl), $S(C_{4-6}$ cycloalkyl), $(C_{1-3}$ alkyl)$(C_{4-9}$ $hetCyc^1$), $hetAr^1$, or O(phenyl) optionally substituted with CN;
$R^6$ is H or $C_{1-4}$ alkyl;
$hetAr^1$ is a 6-membered heteroaryl ring having 1-3 ring nitrogen atoms optionally substituted with $C_{1-4}$ alkyl;
$hetCyc^1$ is a 6-10-membered bicyclic ring having at least one ring heteroatom which is nitrogen and at least one of the rings is aromatic;
m is 0 or 1;
n is 0 or 1;
p is 0 or 1; and
the dashed lines can be single or double bonds.
In some embodiments, A is CH.
In some embodiments, B is CH. In some embodiments, B is N.
In some embodiments, A is O and B is N.
In some embodiments, D is C. In some embodiments, D is N.
In some embodiments, E is CH. In some embodiments, E is N.
In some embodiments, W is N. In some embodiments, W is C.
In some embodiments, X is C.
In some embodiments, Y is C. In some embodiments, Y is N.
In some embodiments, Z is N. In some embodiments, Z is C.
In some embodiments, $R^1$ is H. In some embodiments, $R^1$ is $C_{1-4}$ alkyl or $hetAr^1$. In some embodiments, $R^1$ is methyl, isopropyl, or pyridine.
In some embodiments, $R^4$ is H. In some embodiments, $R^4$ is $C_1$, $CF_3$, methyl or phenyl.

In some embodiments, $R^5$ is H or phenyl optionally substituted with halogen.

In some embodiments, $R^5$ is ($C_{1-3}$ alkyl)O($C_{4-6}$ cycloalkyl), O($C_{1-4}$ alkyl)($C_{4-6}$ cycloalkyl), or O(phenyl) which is optionally substituted with CN. In some embodiments, $C_{4-6}$ cycloalkyl is cyclopentyl or cyclohexyl. In some embodiments, $R^5$ is ($C_{1-3}$ alkyl)O(cyclopentyl) or O($C_{1-4}$ alkyl) ($C_{4-6}$ cyclohexyl). In some embodiments, $R^5$ is $C_{1-4}$ alkyl, $C_{4-10}$ cycloalkyl, or ($C_{1-3}$ alkyl)($C_{4-9}$ hetCyc$^1$). In some embodiments, hetCyc$^1$ is a 9-membered bicyclic ring having one or more nitrogen atoms. In some embodiments, hetCyc$^1$ is isoindoline. In some embodiments, $R^5$ is S($C_{1-4}$ alkyl) or S($C_{4-6}$ cycloalkyl). In some embodiments, $C_{4-6}$ cycloalkyl cyclopentyl or cyclohexyl. In some embodiments, $R^5$ is phenyl substituted with F. In some embodiments, $R^5$ is hetAr$^1$. In some embodiments, hetAr$^1$ is pyridine or pyrimidine optionally substituted with $C_{1-4}$ alkyl.

In some embodiments, $R^6$ is H.

In some embodiments, m is 1.

In some embodiments, n is 0.

In some embodiment, p is 0. In some embodiments, p is 1.

In some embodiments, the compound of Formula I is selected from the group consisting of:

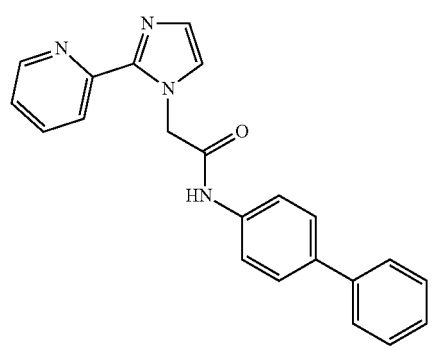

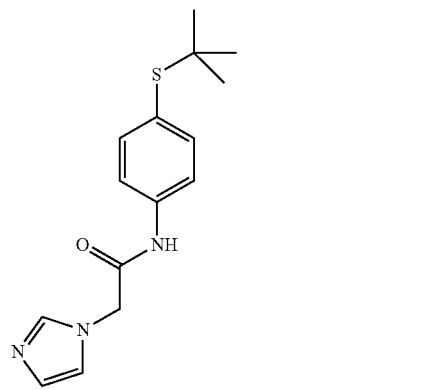

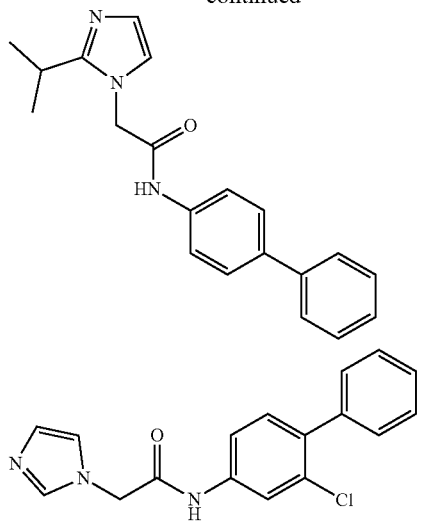

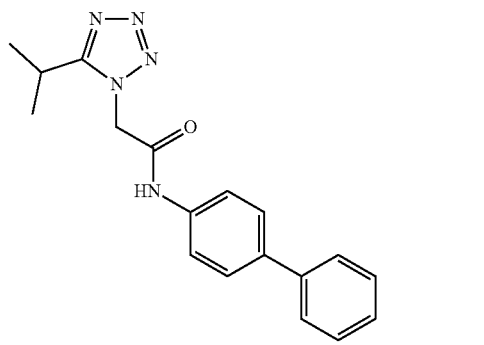

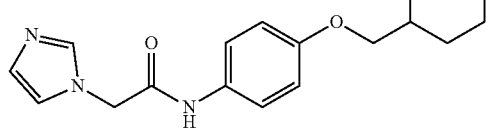

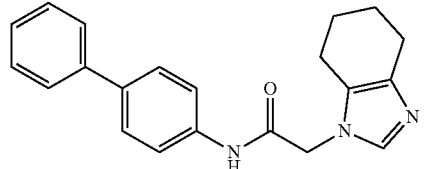

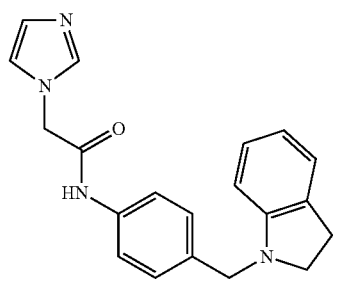

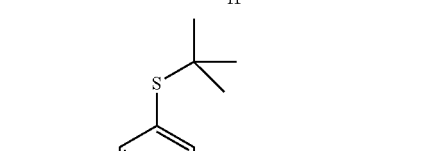

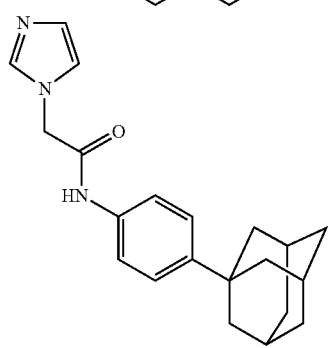

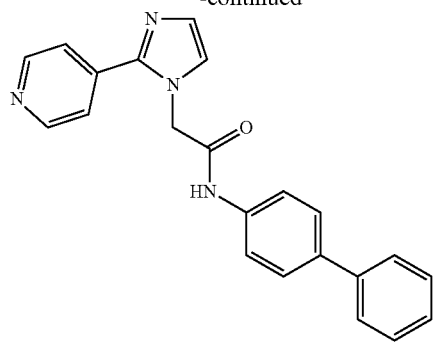
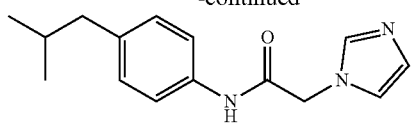
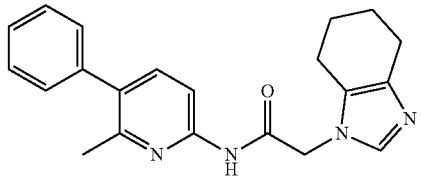
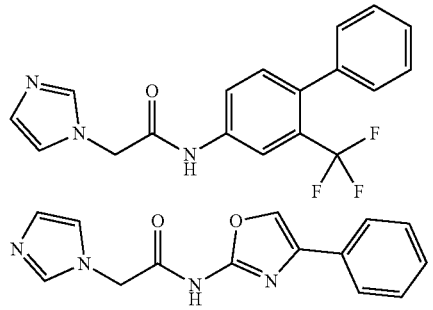
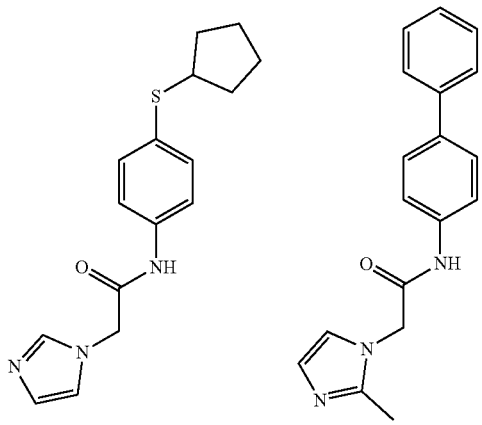
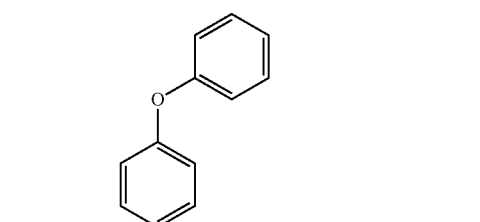
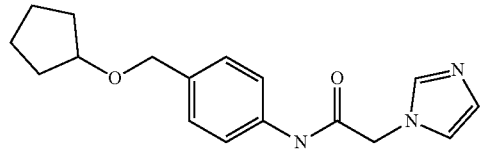
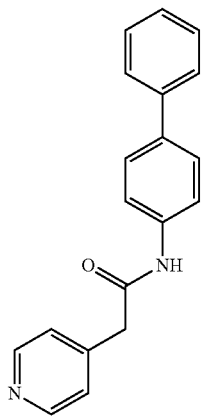
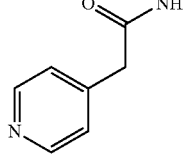
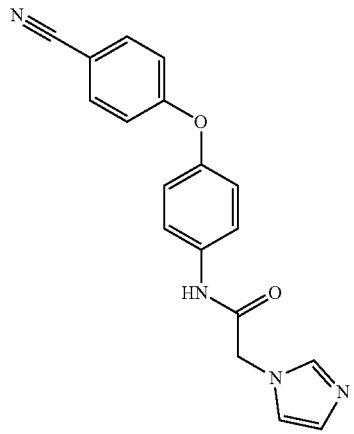
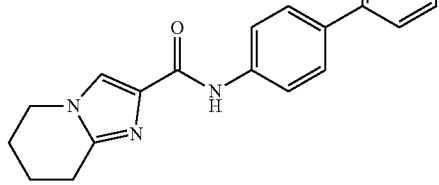

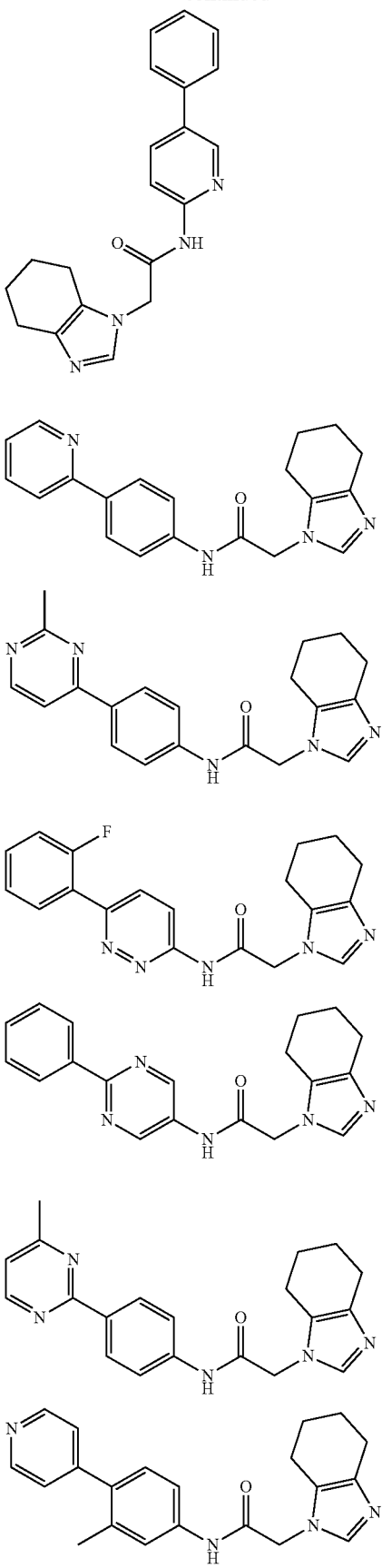

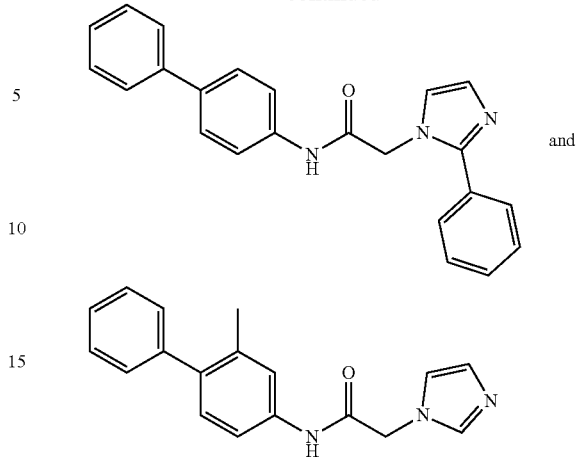

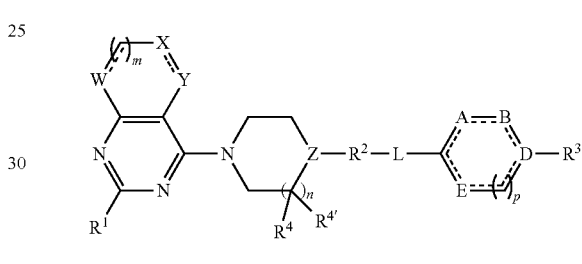

or a pharmaceutically acceptable salt thereof.

The present application also provides compounds of Formula II:

$$\underset{R^1}{\overset{(\phantom{X})_m\phantom{X}}{\underset{N}{\overset{W}{\underset{\phantom{N}}{\bigvee}}}\overset{X}{\underset{Y}{\bigvee}}}} N\underset{R^4\phantom{x}R^{4'}}{\overset{Z-R^2-L}{\underset{()_n}{\bigvee}}} \overset{A=B}{\underset{E}{\bigvee}}\!\!\!D\!-\!R^3$$

or a pharmaceutically acceptable salt thereof, wherein:
A is CH, N, or S;
B is CH, N, O, or S;
D is C or N;
E is CH or N;
L is $C_{1-3}$ alkylene or C(=O);
W is CH, $CH_2$, N, or $NR^a$;
X is CH, $CH_2$, N, or $NR^b$;
Y is CH, $CH_2$ or O;
Z is N or $CR^{2'}$;
$R^1$ is H or $C_{1-3}$ alkyl;
$R^2$ is absent or $C_{1-6}$ alkylene;
$R^{2'}$ is H or $C_{1-6}$ alkyl;
or, when Z is $CR^{2'}$, $R^2$ and $R^{2'}$, together with C, can be taken together to form a $C_{1-6}$ heterocyclic ring;
$R^3$ is H, halogen, $C_{1-3}$ alkyl, $C_{3-6}$ cycloalkyl, or $C_{1-3}$ alkoxy;
$R^4$ is H or $C_{1-3}$ alkyl;
$R^{4'}$ is H or $C_{1-3}$ alkyl;
$R^a$ is H or $C_{1-3}$ alkyl;
$R^b$ is $C_{1-3}$ alkyl;
n is 1 or 2;
m is 0, 1 or 2;
p is 0 or 1; and
the dashed lines can be single or double bonds;
with the proviso that when n is 2, $R^1$ is methyl, D is C, $R^3$ is H, and A, B, and E are all CH, then at least one of W, X, and Y is not $CH_2$.

In some embodiments, A is CH. In some embodiments, A is N. In some embodiments, A is S.

In some embodiments, B is CH. In some embodiments, B is N, O, or S.

In some embodiments, D is C.

In some embodiments, E is CH. In some embodiments, E is N.

In some embodiments, L is $C_{1-3}$ alkylene. In some embodiments, L is methylene.

In some embodiments, W is $CH_2$. In some embodiments, W is N.

In some embodiments, X is $CH_2$. In some embodiments, X is CH. In some embodiments, X is $NR^b$. In some embodiments, $R^b$ is methyl.

In some embodiments, Y is $CH_2$. In some embodiments, Y is CH.

In some embodiments, Z is N.

In some embodiments, $R^2$ is absent.

In some embodiments, Z is $CR^{2'}$. In some embodiments, $R^2$ and $R^{2'}$, together with C, form a 5-membered heterocyclic ring having 1 nitrogen atom.

In some embodiments, $R^1$ is H. In some embodiments, $R^1$ is methyl.

In some embodiments, $R^a$ is H or methyl.

In some embodiments, $R^b$ is methyl.

In some embodiments, $R^3$ is H, halogen, or $C_{3-6}$ cycloalkyl. In some embodiments, $R^3$ is chlorine. In some embodiments, $R^3$ is cyclopropyl.

In some embodiments, $R^4$ and $R^{4'}$ are each H. In some embodiments, $R^4$ and $R^{4'}$ are each methyl.

In some embodiments, n is 2. In some embodiments, n is 1.

In some embodiments, m is 1 or 2.

In some embodiments, p is 0. In some embodiments, p is 1.

In some embodiments, the compound of Formula II is selected from the group consisting of:

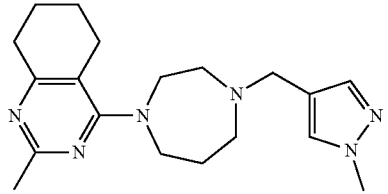

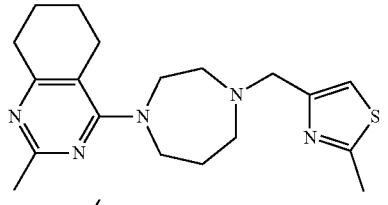

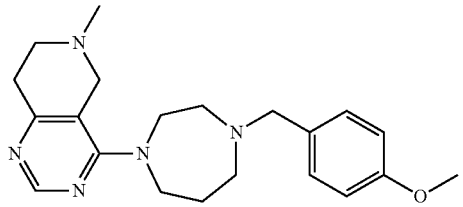

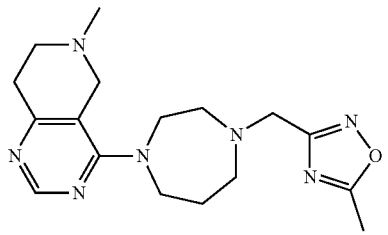

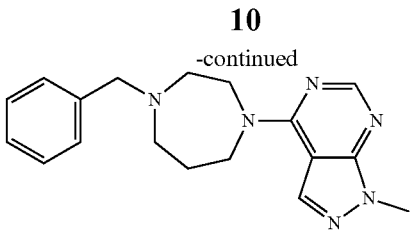

-continued

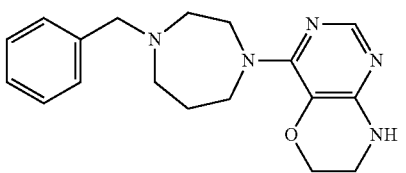

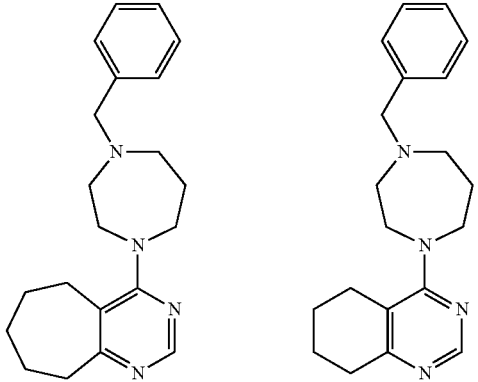

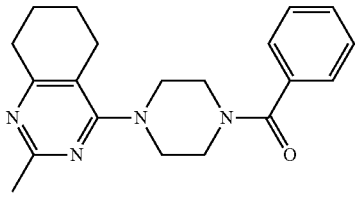

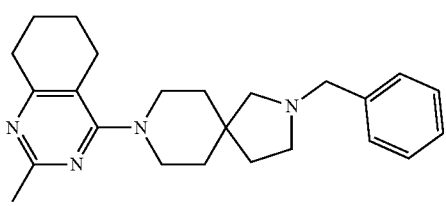

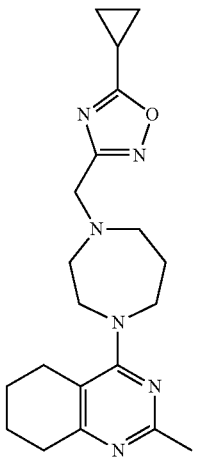

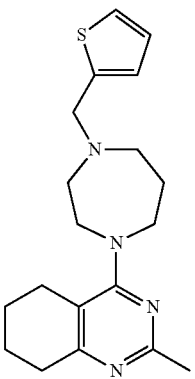

11
-continued

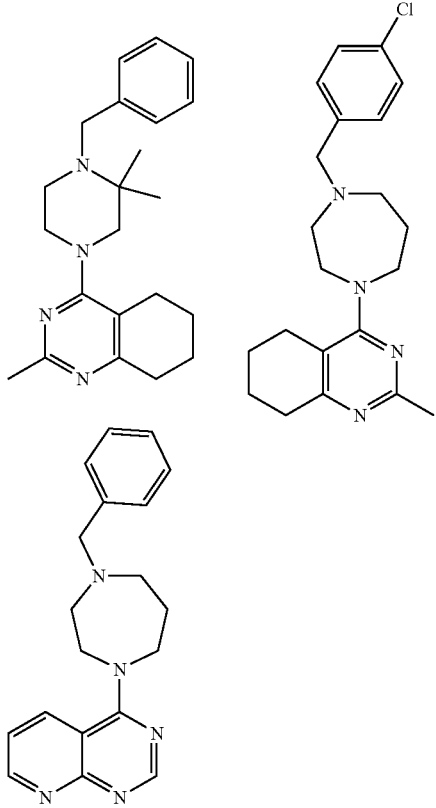

or a pharmaceutically acceptable salt thereof.

In some embodiments, the compound of Formula II is a compound of Formula IIa:

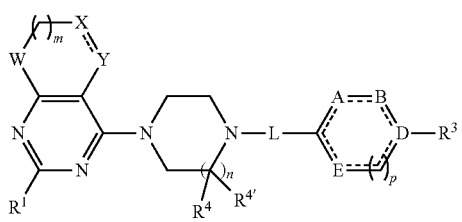

or a pharmaceutically acceptable salt thereof, wherein:
A is CH or N;
B is N, O, or S;
D is C or N;
E is CH or N;
W is $CH_2$, $NR^a$;
X is CH, $CH_2$, N, or $NR^b$;
Y is CH, $CH_2$ or O;
L is $C_{1-3}$ alkylene or C(=O);
$R^1$ is H or $C_{1-3}$ alkyl;
$R^3$ is $C_{1-3}$ alkyl or $C_{1-3}$ alkoxy;
$R^4$ is H or $C_{1-3}$ alkyl;
$R^{4'}$ is H or $C_{1-3}$ alkyl;
$R^a$ is H or $C_{1-3}$ alkyl;
$R^b$ is $C_{1-3}$ alkyl;
n is 1 or 2;
m is 0, 1 or 2;
p is 0 or 1; and
the dashed lines can be single or double bonds.

12

In some embodiments, the compound of Formula II is a compound of Formula IIb:

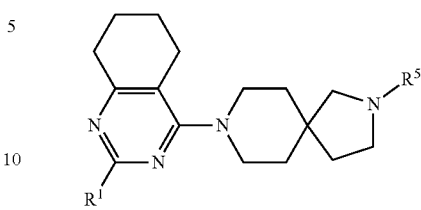

and or a pharmaceutically acceptable salt thereof, wherein:
$R^1$ is $C_{1-3}$ alkyl; and
$R^5$ is ($C_{1-3}$ alkyl)phenyl.

The present application further provides pharmaceutical compositions comprising a compound provided herein, or a pharmaceutically acceptable salt thereof, and at least one pharmaceutically acceptable carrier.

The present application further provides methods of activating the enzymatic activity of an E3 ubiquitin ligase in a subject, the method comprising administering to the subject a therapeutically effective amount of a compound provided herein, or a pharmaceutically acceptable salt thereof.

In some embodiments, the E3 ubiquitin ligase is selected from the group consisting of Parkin, ARIH1 (HHARI), ARIH2 (TRIAD1), RNF31 (HOIP), RBCK1 (HOIL-1L), MUL1 (MAPL, MULAN), MARCH5 (MITOL), E3A, mdm2, anaphase-promoting complex (APC), UBR5 (EDD1), SOCS, LNXp80, CBX4, CBLL1, HACE1, HECTD1, HECTD2, HECTD3, HECW1, HECW2, HERC1, HERC2, HERC3, HERC4, HUWE1, ITCH, NEDD4, NEDD4L, PPIL2, PRPF19, PIAS1, PIAS2, PIAS3, PIAS4, RANBP2, RNF4, RBX1, SMURF1, SMURF2, STUB1, TOPORS, TRIP12, UBE3A, UBE3B, UBE3C, UBE4A, UBE4B, UBOX5, UBR5, WWP1, and WWP2.

In some embodiments, the enzymatic activity is activated or enhanced during mitochondrial stress.

In some embodiments, the compound stimulates mitochondrial quality control.

In some embodiments, the compound interferes with the auto-inhibition of the ligase.

In some embodiments, the subject has diminished E3 ubiquitin ligase enzymatic activity. In some embodiments, the enzymatic activity is diminished due to a disease, aging, or an age-related disorder.

In some embodiments, the disease or disorder is selected from the group consisting of Parkinson's disease, parkinsonism, Alzheimer's disease, dementia, Amyotrophic lateral sclerosis, Frontotemporal dementia, autism, depression, progeroid disorder, leprosy, an inclusion body myositis, diabetes mellitus, diabetic kidney disease, a liver disease, a lysosomal storage disorder, a neurological disease, a muscular disease, a mitochondrial disease, and cancer.

In some embodiments, the disease or disorder is Parkinson's disease.

In some embodiments, the disease or disorder is cancer. In some embodiments, the cancer is selected from the group consisting of liver cancer, brain cancer, skin cancer, kidney cancer, lung cancer, colon cancer, pancreatic cancer, hepatocellular carcinoma, glioma, skin cutaneous melanoma, clear cell renal cell carcinoma, non-small cell lung cancer, lung adenocarcinoma, lung squamous cell cancer, colorectal cancer, pancreatic adenocarcinoma, adenoid cystic carcinoma, acute lymphoblastic leukemia, chronic myeloid leukemia, bladder urothelial cancer, head and neck squamous cell carcinoma, esophageal adenocarcinoma, gastric cancer, cervical cancer, thyroid cancer, and endometrioid cancer.

The present application further provides a method of treating a disease or disorder associated with diminished E3 ubiquitin ligase enzymatic activity in a subject, the method comprising administering to the subject a therapeutically effective amount of a compound provided herein, or a pharmaceutically acceptable salt thereof.

In some embodiments, the E3 ubiquitin ligase is selected from the group consisting of Parkin, ARIH1 (HHARI), ARIH2 (TRIAD1), RNF31 (HOIP), RBCK1 (HOIL-1L), MUL1 (MAPL, MULAN), MARCH5 (MITOL), E3A, mdm2, anaphase-promoting complex (APC), UBR5 (EDD1), SOCS, LNXp80, CBX4, CBLL1, HACE1, HECTD1, HECTD2, HECTD3, HECW1, HECW2, HERC1, HERC2, HERC3, HERC4, HUWE1, ITCH, NEDD4, NEDD4L, PPIL2, PRPF19, PIAS1, PIAS2, PIAS3, PIAS4, RANBP2, RNF4, RBX1, SMURF, SMURF2, STUB1, TOPORS, TRIP12, UBE3A, UBE3B, UBE3C, UBE4A, UBE4B, UBOX5, UBR5, WWP1, and WWP2.

In some embodiments, the disease or disorder is selected from the group consisting of Parkinson's disease, parkinsonism, Alzheimer's disease, dementia, Amyotrophic lateral sclerosis, Frontotemporal dementia, autism, depression, leprosy, an inclusion body myositis, progeroid disorder, diabetes mellitus, diabetic kidney disease, a liver disease, a lysosomal storage disorder, a neurological disease, a muscular disease, a mitochondrial disease, and cancer.

In some embodiments, the disease or disorder is Parkinson's disease.

In some embodiments, the disease or disorder is cancer. In some embodiments, the cancer is selected from the group consisting of liver cancer, brain cancer, skin cancer, kidney cancer, lung cancer, colon cancer, pancreatic cancer, hepatocellular carcinoma, glioma, skin cutaneous melanoma, clear cell renal cell carcinoma, non-small cell lung cancer, lung adenocarcinoma, lung squamous cell cancer, colorectal cancer, pancreatic adenocarcinoma, adenoid cystic carcinoma, acute lymphoblastic leukemia, chronic myeloid leukemia, bladder urothelial cancer, head and neck squamous cell carcinoma, esophageal adenocarcinoma, gastric cancer, cervical cancer, thyroid cancer, and endometrioid cancer.

The present application further provides a method of treating a disease or disorder in a subject, the method comprising:
  (a) detecting a disease or disorder associated with diminished E3 ubiquitin ligase enzymatic activity; and
  (b) administering to the subject a therapeutically effective amount of a compound provided herein, or a pharmaceutically acceptable salt thereof.

In some embodiments, the E3 ubiquitin ligase is selected from the group consisting of Parkin, ARIH1 (HHARI), ARIH2 (TRIAD1), RNF31 (HOIP), RBCK1 (HOIL-1L), MUL1 (MAPL, MULAN), MARCH5 (MITOL), E3A, mdm2, anaphase-promoting complex (APC), UBR5 (EDD1), SOCS, LNXp80, CBX4, CBLL1, HACE1, HECTD1, HECTD2, HECTD3, HECW1, HECW2, HERC1, HERC2, HERC3, HERC4, HUWE1, ITCH, NEDD4, NEDD4L, PPIL2, PRPF19, PIAS1, PIAS2, PIAS3, PIAS4, RANBP2, RNF4, RBX1, SMURF1, SMURF2, STUB1, TOPORS, TRIP12, UBE3A, UBE3B, UBE3C, UBE4A, UBE4B, UBOX5, UBR5, WWP1, and WWP2.

In some embodiments, the disease or disorder is selected from the group consisting of Parkinson's disease, parkinsonism, Alzheimer's disease, dementia, Amyotrophic lateral sclerosis, Frontotemporal dementia, autism, depression, leprosy, an inclusion body myositis, diabetes mellitus, diabetic kidney disease, a liver disease, a lysosomal storage disorder, a neurological disease, a muscular disease, a mitochondrial disease, and cancer.

In some embodiments, the disease or disorder is Parkinson's disease.

In some embodiments, the disease or disorder is cancer. In some embodiments, the cancer is selected from the group consisting of liver cancer, brain cancer, skin cancer, kidney cancer, lung cancer, colon cancer, pancreatic cancer, hepatocellular carcinoma, glioma, skin cutaneous melanoma, clear cell renal cell carcinoma, non-small cell lung cancer, lung adenocarcinoma, lung squamous cell cancer, colorectal cancer, pancreatic adenocarcinoma, adenoid cystic carcinoma, acute lymphoblastic leukemia, chronic myeloid leukemia, bladder urothelial cancer, head and neck squamous cell carcinoma, esophageal adenocarcinoma, gastric cancer, cervical cancer, thyroid cancer, and endometrioid cancer.

The present application further provides a method of treating Parkinson's disease in a subject, the method comprising:
  (a) detecting Parkinson's disease in a subject; and
  (b) administering to the subject a therapeutically effective amount of a compound provided herein, or a pharmaceutically acceptable salt thereof.

The present application further provides a method of treating an age-related disorder in a subject, the method comprising:
  (a) detecting an age-related disorder in a subject; and
  (b) administering to the subject a therapeutically effective amount of a compound provided herein, or a pharmaceutically acceptable salt thereof.

The present application further provides a method of treating cancer in a subject, the method comprising:
  (a) detecting cancer in a subject; and
  (b) administering to the subject a therapeutically effective amount of a compound provided herein, or a pharmaceutically acceptable salt thereof.

In some embodiments, the cancer is selected from the group consisting of liver cancer, brain cancer, skin cancer, kidney cancer, lung cancer, colon cancer, pancreatic cancer, hepatocellular carcinoma, glioma, skin cutaneous melanoma, clear cell renal cell carcinoma, non-small cell lung cancer, lung adenocarcinoma, lung squamous cell cancer, colorectal cancer, pancreatic adenocarcinoma, adenoid cystic carcinoma, acute lymphoblastic leukemia, chronic myeloid leukemia, bladder urothelial cancer, head and neck squamous cell carcinoma, esophageal adenocarcinoma, gastric cancer, cervical cancer, thyroid cancer, and endometrioid cancer.

The present application further provides a method of activating the enzymatic activity of an E3 ubiquitin ligase in a cell, the method comprising contacting the cell with a compound provided herein, or a pharmaceutically acceptable salt thereof.

In some embodiments, the E3 ubiquitin ligase is selected from the group consisting of Parkin, ARIH1 (HHARI), ARIH2 (TRIAD1), RNF31 (HOIP), RBCK1 (HOIL-1L), MUL1 (MAPL, MULAN), MARCH5 (MITOL), E3A, mdm2, anaphase-promoting complex (APC), UBR5 (EDD1), SOCS, LNXp80, CBX4, CBLL1, HACE1, HECTD1, HECTD2, HECTD3, HECW1, HECW2, HERC1, HERC2, HERC3, HERC4, HUWE1, ITCH, NEDD4, NEDD4L, PPIL2, PRPF19, PIAS1, PIAS2, PIAS3, PIAS4, RANBP2, RNF4, RBX1, SMURF1, SMURF2, STUB1, TOPORS, TRIP12, UBE3A, UBE3B, UBE3C, UBE4A, UBE4B, UBOX5, UBR5, WWP1, and WWP2.

In some embodiments, the enzymatic activity is activated during mitochondrial stress.

In some embodiments, the compound stimulates mitochondrial quality control.

In some embodiments, the compound interferes with the auto-inhibition of the ligase.

In some embodiments, the cell has diminished E3 ubiquitin ligase enzymatic activity.

In some embodiments, the contacting is in vitro.

DESCRIPTION OF THE DRAWINGS

FIG. 1A shows the results of the HCI assay using HeLa cells stably expressing GFP-Parkin. GFP-Parkin is localized throughout the cell in unstressed cells but translocates to mitochondria when the mitochondrial membrane potential is compromised and Parkin is activated. After automated image acquisition of fixed cells, regions of interest of each cell were defined with the analysis software. The assay used a "RING—two output" algorithm that resulted in a nuclear mask and a cytoplasmic mask that were being created with help of the nuclear dye Hoechst. To quantify the relocalization of GFP-Parkin to mitochondria, the ratio of the GFP intensity in the cytoplasm and the nucleus was calculated. Under non-stressed condition, this ratio is about 1. FIG. 1B is a bar graph showing the results of the assay with a Z factor (Z') of 0.5-0.8, which indicates its robustness and usefulness as a screening assay. Validation of the assay has been performed by using PINK1 siRNA.

FIG. 2A is a graphic description of the primary HCI assay of EGFP-Parkin translocation. HeLa cells stably expressing GFP-Parkin were seeded with 1350 cells per well in 384-well plates (25 µL per well). Cells were allowed to attach overnight before drug was added 2× concentrated in a volume of 25 µL in triplicates. After 2 h, 50 µL of a 2× low-dose CCCP (yielding a final concentration of 3.5 µM CCCP) was added to all wells that contained test compounds and for the negative control. For positive control wells, CCCP was added in a final concentration of 10 µM. After 2 h incubation with CCCP, cells were fixed and labeled with Hoechst for at least 1 h before cells were imaged. FIG. 2B shows an example of a CCCP titration. FIG. 2C shows the result of a typical drug screen plate. Values were being normalized to negative and positive control values and plotted as % activity. Z' was calculated for quality control. Positive controls were indicated in green, negative control wells in red. Drugs that lead to more than 50% activity are considered positive (blue).

FIGS. 3A-3E show the dose-response curves (DRCs) of Compounds 1 (FIG. 3B), 2 (FIG. 3C), 3 (FIG. 3D), 4 (FIG. 3E), and 31 (FIG. 3A), which showed activity at 1 µM. The graphs show DRCs of EGFP-Parkin translocation to damaged mitochondria. Cells were treated in 384-well plates in triplicates with 12 different concentrations of the drugs. % activity is plotted versus the concentration [M] in log scale. Curve fit and $EC_{50}$ value calculations were done with Graph Pad Prism software. All $EC_{50}$s are in the upper nanomolar range.

FIGS. 4A-4E show normalized DRCs of Compounds 1 (FIG. 4B), 2 (FIG. 4C), 3 (FIG. 4D), 4 (FIG. 4E), and 31 (FIG. 4A) with pS65-Ub antibodies (EGFP-Parkin translocation vs. pS65-UB levels vs. cell death). The number of cells are indicated by squares. The curve fit of pS65-Ub is indicated by circles. The curve fit of translocation is indicated by triangles. Cell death was controlled for by calculating the number of cells per well. In addition, the same plates were stained with pS65-Ub antibodies. Overlay of normalized DRCs of Parkin translocation and pS65-Ub signal gave similar values for all tested compounds.

FIG. 12 is a summary of parameters of Compounds 1-6, 8, 20, and 31. This table summarizes chemoinformatic properties and in vitro toxicity parameters of 20 PACs together with their molecular weight and their $EC_{50}$ values as assessed in the primary assay screen (Parkin translocation to mitochondria). Compounds show zero violations of Lipinski's Rule of Five, are neutral on CNS metric or even predicted for good CNS penetrance with low in silico toxicity concerns, as well as excellent MW, PSA, log P, and Caco-2 for improved CNS function.

FIGS. 15A-15H show Parkin activation in primary fibroblasts, neuronal cells and in vitro. Positive control (PC) cells were treated with DMSO and 10 μM of CCCP. Negative control (NC) cells were treated with 3.5 μM CCCP, some cells were left untreated (−). FIG. 15A: Western blot of human fibroblasts treated with 5 μM of compound 4 for 2 h before different concentrations of CCCP were added shows increased ubiquitylation/degradation of mitofusins and amplification of the pSer65-Ub signal. Vinculin was used as loading control. FIG. 15B: Western blot of fibroblasts pre-treated with 5 μM of compounds 1, 2, 3, 4, and 31 before low dose CCCP (3.5 μM) show enhanced degradation of the substrates MFN1/2 and increase of pSer65-Ub levels. FIG. 15C: Human fibroblasts were directly converted to neurons and treated as in FIG. 15B. Western blot shows the induction of modified MFN1 and of pSer65-Ub upon compound treatment, similar to PC, but not NC cells. Beta III tubulin confirmed successful conversion of fibroblasts to iNeurons. FIG. 15D: Rat PC12 cells were treated as in FIG. 15A. Western blots show enhanced ubiquitylation of MFN2 and TOM70, and robust pSer65-Ub induction similar to PC, but not NC cells. FIG. 15E: In vitro E2 discharge assay. Recombinant Parkin was pre-incubated with compound 4 or DMSO as control and was mixed to Ub-loaded UbcH7. FLAG-Ubiquitin and UbcH7 western blots both show slightly more E2 discharge in presence of compound 4. Control reactions were performed without PINK1 or Parkin. FIG. 15F: In vitro assay with isolated mitochondria from untreated or CCCP-treated HeLa cells lacking Parkin. Mitochondrial preparations were mixed with recombinant Parkin, E1, UbcH7, ATP and either compound 4 or DMSO as a control and incubated for the indicated times. MFN1 western blot show increased ubiquitylation when compound 4 is present. Control samples were incubated in reaction mix without Parkin. FIG. 15G: Protein melting was performed with 50 ng purified Parkin mixed with SYPRO orange and DMSO as control or 500 nM compound 4. Analysis of triplicate reactions revealed a 3° C. temperature shift. FIG. 15H: Statistical analysis of three independent experiments as performed in FIG. 15G. Shown in the average value+/−SD (unpaired, two-sided t-test; *** p<0.0005).

FIG. 16A: Quantification of pSer65-Ub signal using sandwich ELISA from six independent experiments performed in human fibroblast treated as described in FIG. 15A. Shown in the average−/+SD. One-way ANOVA with Tukey's posthoc test (*** p<0.0005). FIG. 16B: Human primary fibroblasts were treated with different concentrations of all five compounds (1, 2, 3, 4, and 31) for 2 h. Compound treatment alone (i.e., in the absence of CCCP) did not induce MFN1 ubiquitylation or pSer65-Ub signals. Different CCCP concentrations were used as positive control. FIG. 16C: Rat PC12 cells were pretreated with 5 μM of the compounds for 2 h and then treated with low dose of CCCP (3.5 μM). Control cells were treated with DMSO and either 10 μM CCCP (PC) or 3.5 μM (NC). Some cells received no CCCP (−). Western blot shows ubiquitinylation (gray arrowheads) and or decrease of unmodified (black arrowhead) MFN1/2 and TOM70. The PINK1/Parkin product pSer65-Ub was induced by all five compounds upon low dose treatment and in positive controls. FIG. 16D: PC12 cells were differentiated by treatment with NGF (NGF+). Some cells were left undifferentiated (NGF−). Cells were treated with 5 μM of compounds or DMSO as indicated. 2 h later, low dose CCCP (3.5 μM) was added to cells treated with test compounds. DMSO controls were either treated with 3.5 μM CCCP (NC) or 10 μM CCCP (PC). Some cells were not treated with CCCP (−). Western blots probed with antibodies against MFN1 show degradation in cells treated with compounds and in the positive control. Some degradation can also be observed in the negative control. The PINK1/Parkin product pSer65 shows increased induction in cells that have been treated with compound compared to the negative control. Beta III tubulin was used to confirm successful differentiation. Vinculin was used as loading control.

FIGS. 17A-17L are detailed chemoinformatic properties of the Parkin activating compounds 1-6, 8-12, 14-20, and 29-31. The table lists the compounds in columns with each column containing the docking score, experimental activity (nM) from dose response, chemoinformatics properties, and ligand efficiency. FIGS. 17A-17C show properties for compounds 1-4 and 6. FIGS. 17D-17F show properties for compounds 8-12. FIGS. 17G-17I show properties for compounds 14-18. FIGS. 17J-17L show properties for compounds 19, 20, and 29-31.

FIGS. 19A-19D show microsomal stability data for compounds 1-4 and 31 and reference compounds (imipramine and propranolol) in mouse liver microsomes.

FIG. 20A is the CYP inhibition profile for compound 31. FIG. 20B is the CYP inhibition profile for compound 1. FIG. 20C is the CYP inhibition profile for compound 2. FIG. 20D is the CYP inhibition profile for compound 3. FIG. 20E is the CYP inhibition profile for compound 4.

DETAILED DESCRIPTION

Figures 1A, 1B:
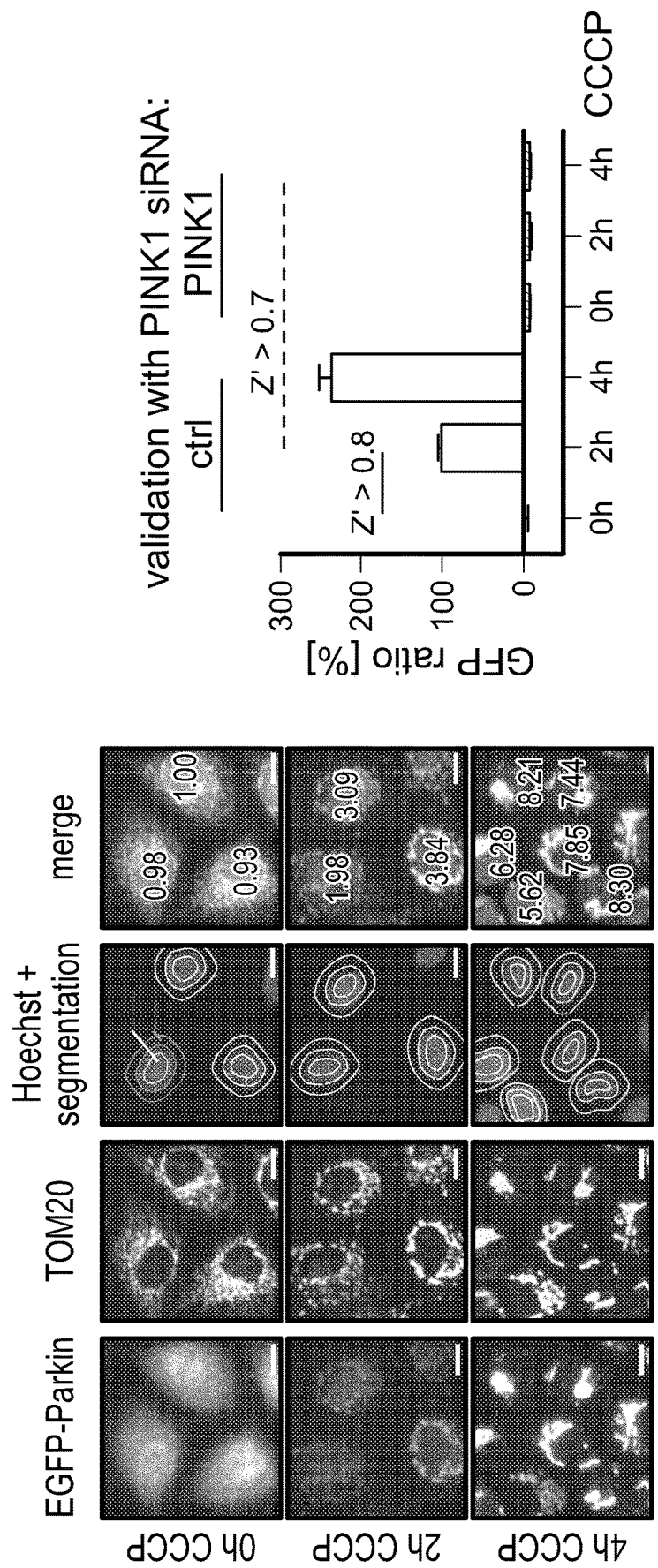
FIGS. 1A-1B show the results of a primary screening assay with high content imaging (HCI) of enhanced green fluorescent protein (EGFP)-Parkin translocation.
Figure 2A:
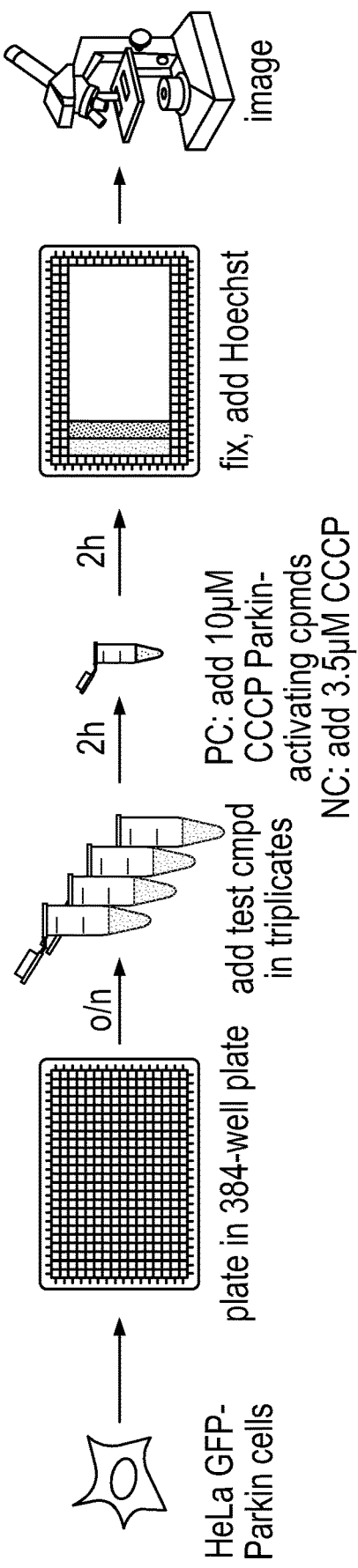
FIGS. 2A-2C show a primary HCI assay with CCCP titration.
Figure 2B:
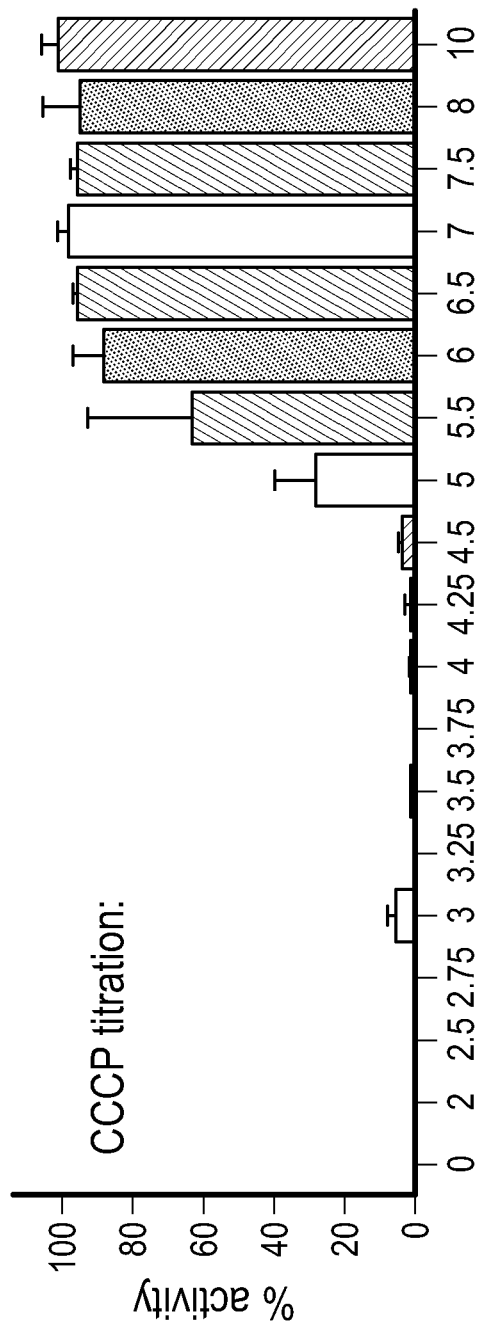
Figure 2C:
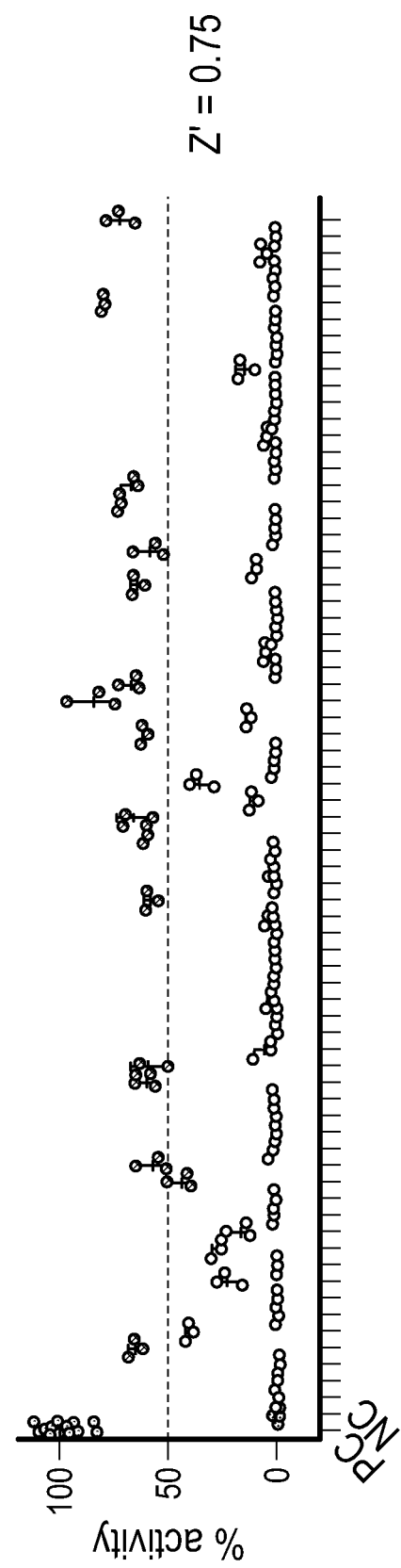
Figure 5:
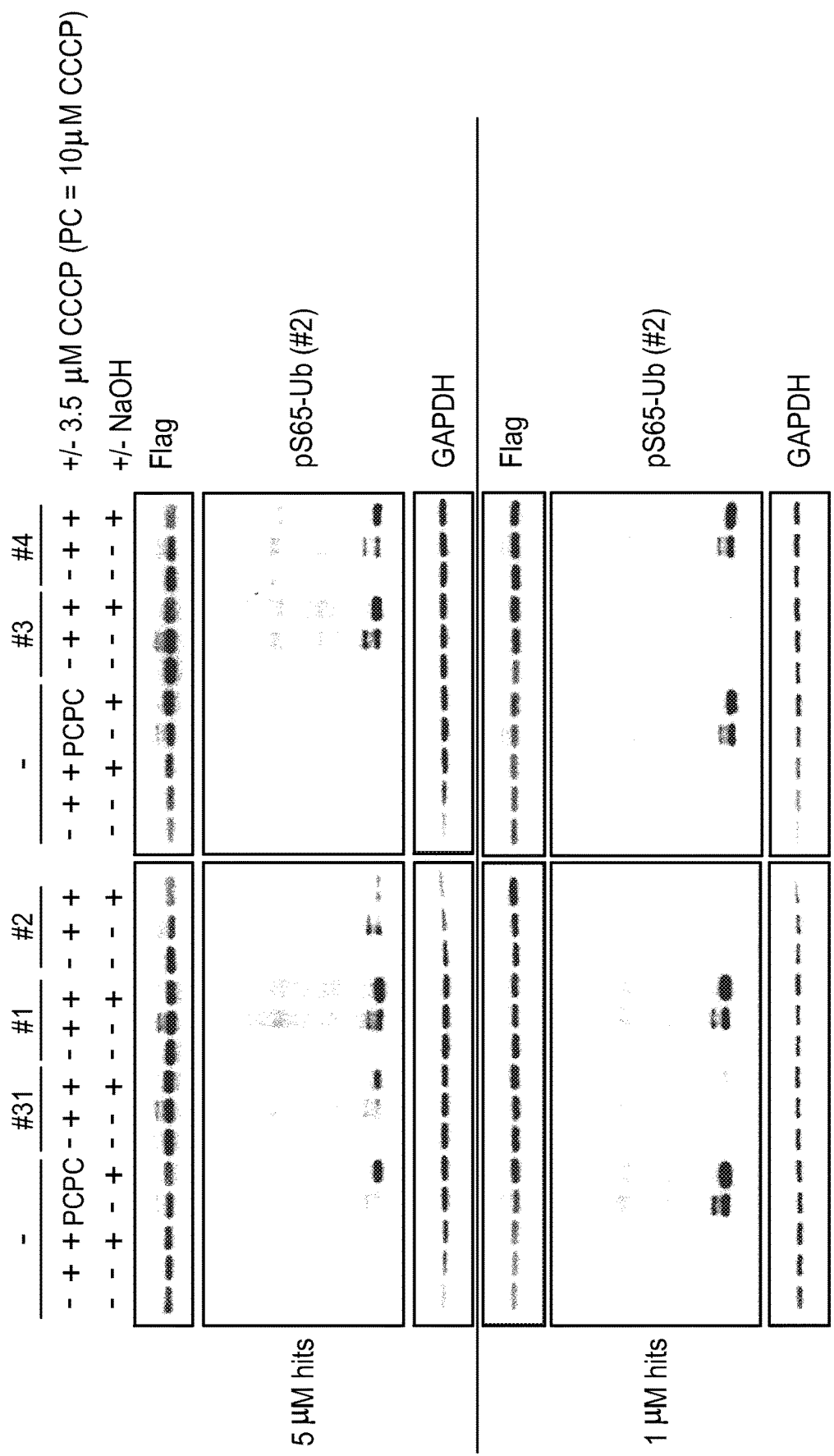
FIG. 5 shows enhanced Ub-charging of FLAG-Parkin C431S (WB) by pre-treatment with Compounds 1, 2, 3, 4, and 31. Another measure of Parkin activation is Ub charging of Parkin. Parkin receives Ub from an E2 enzyme to transfer it to a substrate protein. The Ub is bound by Parkin C431 in an unstable thioester bond. A serine substitution of this amino acid (C431S) leads to a stable oxyester bond. The bound Ub can then be visualized as a band shift in Western blot experiments. HeLa 3×FLAG-Parkin C431S cells were seeded in 12-well plates and allowed to attach overnight. Cells were treated with 5 µM (top panels) or 1 µM (bottom panels) of Compounds 1, 2, 3, 4, and 31 2 h before adding CCCP for another 2 h. 10 µM CCCP was added to positive control (PC) wells whereas all other samples received a low dose concentration of 3.5 µM. Cells were harvested in boiling hot SDS lysis buffer and protein concentration was determined by BCA. Samples were split and left either untreated or were treated with NaOH as indicated. Samples were run on an 8-16% Tris-Glycine gel, blotted onto membranes and probed with antibodies against Flag and pS65-Ub. GAPDH served as a loading control. Band shift indicates Parkin binding to Ubiquitin, which is cleavable with NaOH.
Figure 6:
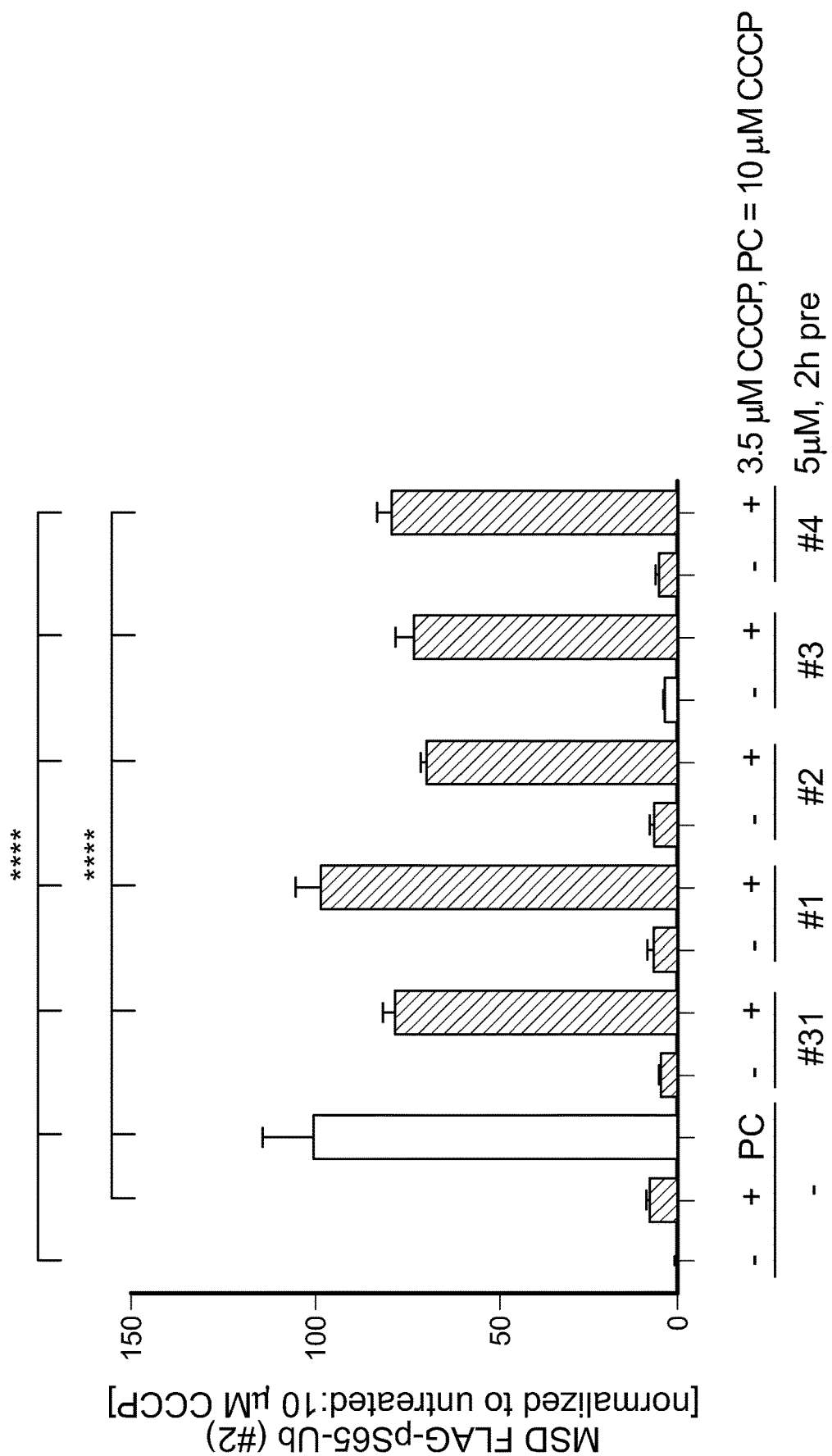
FIG. 6 shows enhanced Ub-charging of FLAG-Parkin C431S (MSD assay) by pre-treatment with Compounds 1, 2, 3, 4, and 31. Ubiquitin charging of Parkin was monitored by ELISA-like MesoScale Discovery assay that uses electrochemiluminescence. Plates were coated with Flag antibody and incubated with lysates from 3×FLAG-Parkin C431S cells that had been pretreated for 2 h with 5 µM of Compounds 1, 2, 3, 4, and 31 or DMSO (left, −) before incubating them for another 2 h with (+) or without (−) low-dose (3.5 µM) CCCP. Positive control (PC) cells were treated with 10 µM CCCP. After washing, pS65-Ub antibody was added together with a sulfo-tagged anti-rabbit antibody. Values were normalized to the PC (10 µM CCCP) and negative control (−). Statistical analysis was performed by one-way ANOVA with Tukey's post-hoc test. ****, $p<0.0001$.
Figure 7:
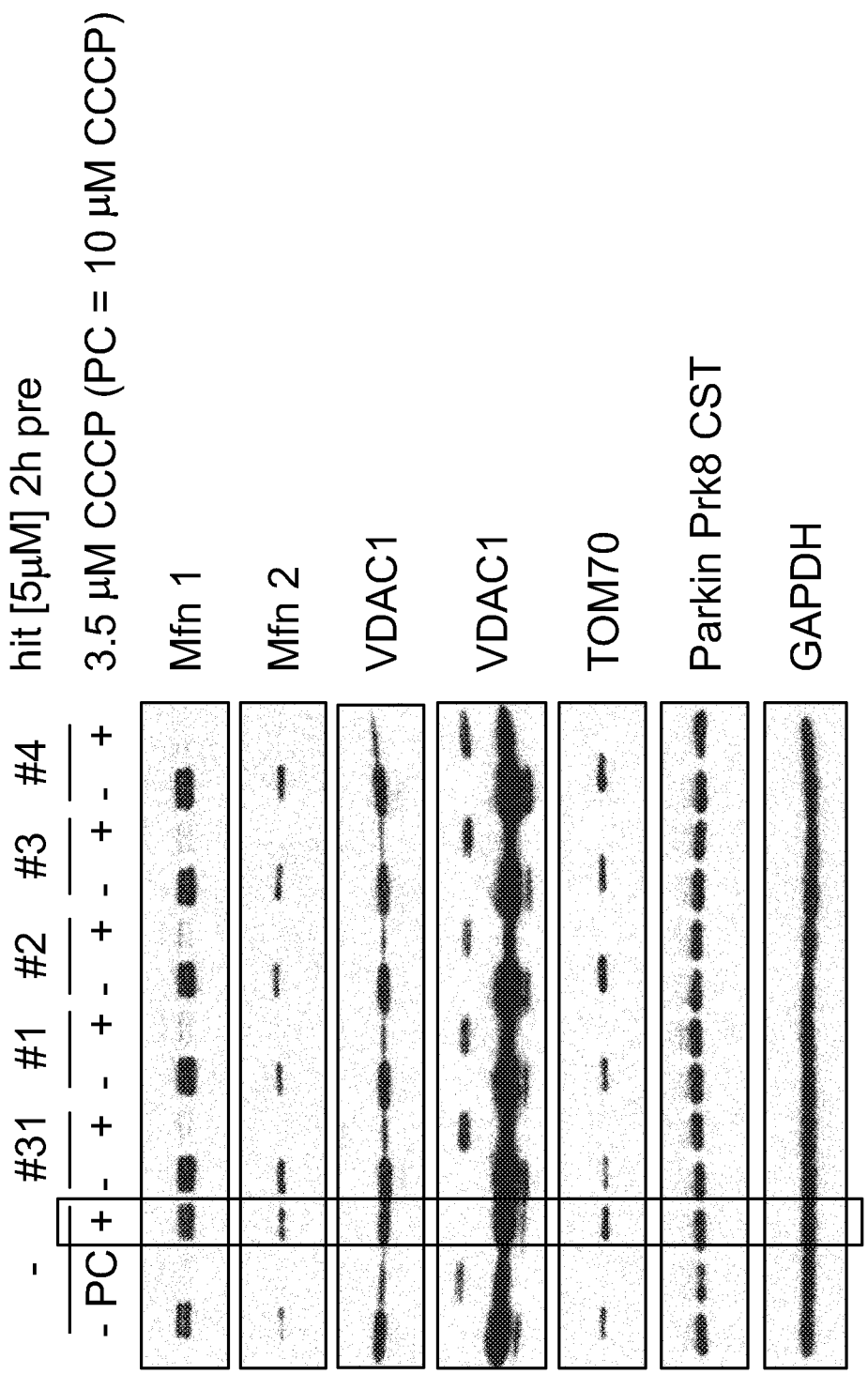
FIG. 7 shows enhanced ubiquitination and degradation of Parkin substrates by pre-treatment with Compounds 1, 2, 3, 4, and 31. HeLa cells stably expressing untagged Parkin were left untreated or pre-treated with 5 µM of Compounds 1, 2, 3, 4, and 31 for 2 h and treated without (−) or with (+) low dose CCCP (3.5 µM CCCP). As a positive control (PC), some cells were treated with 10 µM CCCP. Lysates were loaded onto 8-16% Tris-Glycine gels, blotted onto membranes and probed with antibodies against Parkin substrates. While low-dose CCCP treatment alone does not lead to substrate degradation, cells that were pre-treated with Compounds 1, 2, 3, 4, and 31 showed reduced substrate levels, similar to positive control cells.

Parkin is a cytosolic E3 ubiquitin (Ub) ligase and acts downstream of the mitochondrial kinase PINK1. Upon mitochondrial stress, PINK1 is stabilized on the outer mitochondrial membrane and recruits Parkin by phosphorylation of Ub at the conserved residue Serine 65 (Kane et al. (2014) J. Cell Biol. 205:143-153; Kazlauskaite et al. (2014) Biochem. J. 460:127-139; Koyano et al. (2014) Nature 510:162-166). Phosphorylated Ub (pS65-Ub) can activate Parkin and also acts as the receptor for Parkin on the mitochondrial surface (Okatsu et al. (2015) J. Cell Biol. 109:111-128). Re-localization of Parkin is associated with its enzymatic activation and the ligation of Ub molecules onto mitochondrial substrate proteins (Kazlauskaite et al. (2014) Open Biol. 4:130213) that in turn serve as additional substrates for PINK1 and Parkin (Fiesel et al. (2015) J. Cell Sci. 127:3488-3504). The formed pS65-Ub signal acts as the mitophagy tag and is recognized by autophagy adapters for eventual degradation of the whole organelle in the lysosome (Ordureau et al. (2015) Proc. Natl. Acad. Sci. U.S.A. 112: 6637-6642; Richter et al. (2016) Proc. Natl. Acad. Sci. U.S.A. 113:4039-4044).

Upon stress, the PINK1/Parkin pathway promotes turnover of mitochondria and prevents the accumulation of dysfunctional mitochondria that can lead to cellular degeneration. Under basal conditions, both PINK1 and Parkin are repressed through different mechanisms. PINK1 is constitutively cleaved by the mitochondrial protease PARL and subsequently degraded by the proteasome (Yamano et al. (2013) Autophagy 9:1758-1769). Parkin is present under basal conditions but is structurally very compact with several self-interactions that prohibit activity (Caulfield et al. (2015) Biochem. Soc. Trans. 43:269-274; Caulfield et al. (2014) PLoS Comput. Biol. 10:e1003935). These self-interactions have to be released and Parkin needs to 'open up' in order to become active. Parkin is a RING-in-between-RING (RBR) ligase, a recently described new family of E3 ubiquitin ligases (Wenzel et al. (2011) Nature 474:105-108). Like members of classical RING-type ligases, it contains several RING domains that bind the E2 ubiquitin-conjugating co-factors. Mechanistically however, Parkin acts like a HECT E3 ligase as it physically receives the Ub moiety with its active cysteine (C431) from the E2 before it is transferred onto a substrate. Ub charging of Parkin (i.e., activation) is intimately linked to its mitochondrial recruitment (Iguchi et al. (2013) J. Biol. Chem. 288:22019-22032; Zheng et al. (2013) Cell Res. 23:886-897). Parkin contains an N-terminal ubiquitin-like (UBL) domain with a conserved Ser65 residue. Together with phosphorylation of the modifier protein Ub at S65, PINK1-dependent phosphorylation of Parkin S65 within the UBL (Kazlauskaite et al. (2014) Biochem. J. 460:127-139; Iguchi et al. (2013) J. Biol. Chem. 288:22019-22032; Shiba-Fukushima et al. (2014) PLoS Genet. 10:e1004391) is a key event leading to Parkin activation (Kazlauskaite et al. (2014) Open Biol. 4:130213; Caulfield et al. (2014) PLoS Comput. Biol. 10:e1003935).

Accordingly, the present application provides compounds useful for activating Parkin. These Parkin activating compounds (PACs) are active in the low micromolar/high nanomolar range and have been extensively tested in human cell culture. The purpose of these compounds is to improve PINK1/Parkin mitochondrial quality control. This pathway is impaired in different forms of familial and sporadic PD. In addition, activation of mitochondrial quality control may prove beneficial for a variety of neurological, muscular and other age-related diseases.

In contrast to inhibitors of an enzyme/pathway that often require more than 90% activity (i.e., inhibition), activators/enhancers of a given enzyme/pathway may only require 10% activity (i.e., activation), since even small amounts of active target can be further amplified along the pathway. This decreases side effects due to lower drug concentrations needed for effectiveness. In some embodiments, the herein described PACs can enhance Parkin activation upon an initial mitochondrial stress-induced phosphorylation mediated by PINK1 that results in conformational changes of Parkin and allows access to the drug-binding site. Without being bound by any theory, it is believed that this can limit activation of Parkin's enzymatic functions only when and where needed.

1. Definitions

The term "substituted," as used herein, means that any one or more hydrogens on the designated atom, usually a carbon, oxygen, or nitrogen atom, is replaced with a selection from the indicated group, provided that the designated atom's normal valency is not exceeded, and that the substitution results in a stable compound. When a substituent is keto or oxo (i.e., =O), then 2 hydrogens on the atom are replaced. Ring double bonds, as used herein, are double bonds that are formed between two adjacent ring atoms (e.g., C=C, C=N, N=N, etc.).

As used herein, "alkyl" is intended to include both branched and straight-chain saturated aliphatic hydrocarbon groups having the specified number of carbon atoms. For example, $C_{1-4}$ alkyl is intended to include $C_1$, $C_2$, $C_3$, and $C_4$. $C_{1-6}$ alkyl is intended to include $C_1$, $C_2$, $C_3$, $C_4$, $C_5$, and $C_6$ alkyl groups and $C_{1-8}$ alkyl is intended to include $C_1$, $C_2$, $C_3$, $C_4$, $C_5$, $C_6$, $C_7$, and $C_8$. Some examples of alkyl include, but are not limited to, methyl, ethyl, n-propyl, iso-propyl, n-butyl, s-butyl, t-butyl, n-pentyl, s-pentyl, n-hexyl, n-heptyl, and n-octyl.

As used herein, "alkenyl" is intended to include hydrocarbon chains of either straight or branched configuration and one or more unsaturated carbon-carbon bond that can occur in any stable point along the chain, such as ethenyl and propenyl. For example, $C_{2-6}$ alkenyl is intended to include $C_2$, $C_3$, $C_4$, $C_5$, and $C_6$ alkenyl groups and $C_{2-8}$ alkenyl is intended to include $C_2$, $C_3$, $C_4$, $C_5$, $C_6$, $C_7$, and $C_8$ alkenyl groups.

As used herein, "alkylene" is intended to include moieties which are diradicals, i.e., having two points of attachment. A non-limiting example of such an alkylene moiety that is a diradical is —$CH_2CH_2$—, i.e., a $C_2$ alkyl group that is covalently bonded via each terminal carbon atom to the remainder of the molecule. The alkylene diradicals are also known as "alkylenyl" radicals. Alkylene groups can be saturated or unsaturated (e.g., containing —CH=CH— or —C≡C— subunits), at one or several positions. In some embodiments, alkylene groups include 1 to 9 carbon atoms (for example, 1 to 6 carbon atoms, 1 to 4 carbon atoms, or 1 to 2 carbon atoms). Some examples of alkylene groups include, but are not limited to, methylene, ethylene, n-propylene, iso-propylene, n-butylene, iso-butylene, sec-butylene, tert-butylene, n-pentylene, iso-pentylene, sec-pentylene and neo-pentylene.

As used herein, "cycloalkyl" is intended to include saturated or unsaturated nonaromatic ring groups, such as cyclopropyl, cyclobutyl, cyclopentyl, or cyclohexyl. For example, the term "$C_{3-8}$ cycloalkyl" is intended to include $C_3$, $C_4$, $C_5$, $C_6$, $C_7$, and $C_8$ cycloalkyl groups. Cycloalkyls may include multiple spiro- or fused or bridged rings. For example, cycloalkyl can include, but is not limited to, spiro butyl, pentyl, hexyl, heptyl, octyl, nonyl, or decyl groups, bicyclo butyl, pentyl, hexyl, heptyl, octyl, nonyl, or decyl groups, adamantyl groups, and norbornyl groups.

As used herein, the term "heterocycloalkyl" refers to a saturated or unsaturated nonaromatic 3-8 membered monocyclic, 7-12 membered bicyclic (fused, bridged, or spiro rings), or 11-14 membered tricyclic ring system (fused, bridged, or spiro rings) having one or more heteroatoms (such as O, N, S, or Se), unless specified otherwise. A heterocycloalkyl group containing a fused aromatic ring can be attached through any ring-forming atom including a ring-forming atom of the fused aromatic ring. In some embodiments, the heterocycloalkyl is a monocyclic 4-6 membered heterocycloalkyl having 1 or 2 heteroatoms independently selected from nitrogen, oxygen, or sulfur and having one or more oxidized ring members. In some embodiments, the heterocycloalkyl is a monocyclic or bicyclic 4-10 membered heterocycloalkyl having 1, 2, 3, or 4 heteroatoms independently selected from nitrogen, oxygen, or sulfur and having one or more oxidized ring members. Examples of heterocycloalkyl groups include, but are not limited to, piperidinyl, piperazinyl, pyrrolidinyl, dioxanyl, tetrahydrofuranyl, isoindolinyl, indolinyl, imidazolidinyl, pyrazolidinyl, oxazolidinyl, isoxazolidinyl, triazolidinyl, tetrahyrofuranyl, oxiranyl, azetidinyl, oxetanyl, thietanyl, 1,2,3,6-tetrahydropyridinyl, tetrahydropyranyl, dihydropyranyl, pyranyl, morpholinyl, 1,4-diazepanyl, 1,4-oxazepanyl, 2-oxa-5-azabicyclo[2.2.1]heptanyl, 2,5-diazabicyclo[2.2.1]heptanyl, 2-oxa-6-azaspiro[3.3]heptanyl, 2,6-diazaspiro[3.3]heptanyl, 1,4-dioxa-8-azaspiro[4.5]decanyl and the like.

As used herein, "amine" or "amino" refers to unsubstituted —$NH_2$ unless otherwise specified.

As used herein, "halo" or "halogen" refers to fluoro, chloro, bromo, and iodo substituents.

As used herein, "haloalkyl" is intended to include both branched and straight-chain saturated aliphatic hydrocarbon groups having the specified number of carbon atoms, substituted with one or more halogen (for example —$C_vF_w$ $H_{2v-w+1}$ wherein v=1 to 3 and w=1 to (2v+1)). Examples of haloalkyl include, but are not limited to, trifluoromethyl, trichloromethyl, pentafluoroethyl, and pentachloroethyl.

The term "haloalkoxy" as used herein refers to an alkoxy group, as defined herein, which is substituted one or more halogen. Examples of haloalkoxy groups include, but are not limited to, trifluoromethoxy, difluoromethoxy, pentafluoroethoxy, trichloromethoxy, etc.

As used herein, "alkoxyl" or "alkoxy" refers to an alkyl group as defined above with the indicated number of carbon atoms attached through an oxygen bridge. $C_{1-6}$ alkoxy, is intended to include $C_1$, $C_2$, $C_3$, $C_4$, $C_5$, and $C_6$ alkoxy groups. $C_{1-8}$ alkoxy, is intended to include $C_1$, $C_2$, $C_3$, $C_4$, $C_5$, $C_6$, $C_7$, and $C_8$ alkoxy groups. Examples of alkoxy include, but are not limited to, methoxy, ethoxy, n-propoxy, i-propoxy, n-butoxy, s-butoxy, t-butoxy, n-pentoxy, s-pentoxy, n-heptoxy, and n-octoxy.

As used herein, "aryl" includes groups with aromaticity, including "conjugated," or multicyclic systems with at least one aromatic ring and do not contain any heteroatom in the ring structure. Aryl may be monocyclic or polycyclic (e.g., having 2, 3 or 4 fused rings). The term "$C_{n-m}$ aryl" refers to an aryl group having from n to m ring carbon atoms. In some embodiments, aryl groups have from 6 to 10 carbon atoms. In some embodiments, the aryl group is phenyl or naphthyl.

As used herein, the terms "aromatic heterocycle," "aromatic heterocyclic" or "heteroaryl" ring are intended to mean a stable 5, 6, 7, 8, 9, 10, 11, or 12-membered monocyclic or bicyclic aromatic ring which consists of carbon atoms and one or more heteroatoms, e.g., 1 or 1-2 or 1-3 or 1-4 or 1-5 or 1-6 heteroatoms, independently selected from nitrogen, oxygen, and sulfur. In the case of bicyclic aromatic heterocyclic or heterocycle or heteroaryl rings, only one of the two rings needs to be aromatic (e.g., 2,3-dihydroindole), though both can be (e.g., quinoline). The second ring can also be fused or bridged as defined above for heterocycles. The nitrogen atom can be substituted or unsubstituted (i.e., N or NR wherein R is H or another substituent, as defined). The nitrogen and sulfur heteroatoms can optionally be oxidized (i.e., N→O and S(O)$_p$, wherein p=1 or 2). In certain compounds, the total number of S and O atoms in the aromatic heterocycle is not more than 1.

Examples of aromatic heterocycles, aromatic heterocyclics or heteroaryls include, but are not limited to, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, benzooxadiazoly, carbazolyl, 4aH-carbazolyl, carbolinyl, cinnolinyl, furazanyl, imidazolyl, imidazolonyl, 1H-indazolyl, indolizinyl, indolyl, 3H-indolyl, isobenzofuranyl, isochromanyl, isoindazolyl, isoindolyl, isoquinolinyl, isothiazolyl, isoxazolyl, methylbenztriazolyl, methylfuranyl, methylimidazolyl, methylthiazolyl, naphthyridinyl, oxadiazolyl, 1,2,3-oxadiazolyl, 1,2,4-oxadiazolyl, 1,2,5-oxadiazolyl, 1,3,4-oxadiazolyl, oxazolyl, phenanthridinyl, phenanthrolinyl, phenazinyl, phenothiazinyl, phenoxathinyl, phenoxazinyl, phthalazinyl, pteridinyl, purinyl, pyrazinyl, pyrazolyl, pyridazinyl, pyridooxazolyl, pyridoimidazolyl, pyridothiazolyl, pyridinyl, pyridinonyl, pyridyl, pyrimidinyl, 2H-pyrrolyl, pyrrolyl, quinazolinyl, quinolinyl, 4H-quinolizinyl, quinoxalinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, triazolopyrimidinyl, 1,2,3-triazolyl, 1,2,4-triazolyl, 1,2,5-triazolyl, and 1,3,4-triazolyl.

The term "hydroxyalkyl" means an alkyl group as defined above, where the alkyl group is substituted with one or more OH groups. Examples of hydroxyalkyl groups include HO—CH$_2$—, HO—CH$_2$—CH$_2$— and CH$_3$—CH(OH)—.

The term "cyano" as used herein means a substituent having a carbon atom joined to a nitrogen atom by a triple bond, i.e., C≡N.

As used herein, "oxo" is means a "=O" group.

As used herein, the phrase "pharmaceutically acceptable" refers to those compounds or tautomers thereof, or salts thereof, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds or tautomers thereof, wherein the parent compound or a tautomer thereof, is modified by making of the acid or base salts thereof of the parent compound or a tautomer thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound, or a tautomer thereof, formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, ethane sulfonic, fumaric, glucoheptonic, gluconic, glutamic, glycolic, glycollyarsanilic, hexylresorcinic, hydrabamic, hydrobromic, hydrochloric, hydroiodide, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicylic, stearic, subacetic, succinic, sulfamic, sulfanilic, sulfuric, tannic, tartaric, and toluene sulfonic.

The pharmaceutically acceptable salts of the present disclosure can be synthesized from the parent compound or a tautomer thereof that contains a basic or acidic moiety by conventional chemical methods. Generally, such pharmaceutically acceptable salts can be prepared by reacting the free acid or base forms of these compounds or tautomers thereof with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in Remington's Pharmaceutical Sciences, 18th ed., Mack Publishing Company, Easton, Pa., USA, p. 1445 (1990).

As used herein, "stable compound" and "stable structure" are meant to indicate a compound that is sufficiently robust to survive isolation to a useful degree of purity from a reaction mixture, and formulation into an efficacious therapeutic agent.

As used herein, the term "treating" refers to administering a compound or pharmaceutical composition as provided herein for therapeutic purposes. The term "therapeutic treatment" refers to administering treatment to a patient already suffering from a disease thus causing a therapeutically beneficial effect, such as ameliorating existing symptoms, ameliorating the underlying metabolic causes of symptoms, postponing or preventing the further development of a disorder, and/or reducing the severity of symptoms that will or are expected to develop.

As used herein, "unsaturated" refers to compounds having at least one degree of unsaturation (e.g., at least one multiple bond) and includes partially and fully unsaturated compounds.

As used herein, the term "effective amount" refers to an amount of a compound or a pharmaceutically acceptable salt of the compound or tautomer (including combinations of compounds and/or tautomers thereof, and/or pharmaceutically acceptable salts of said compound or tautomer) of the present disclosure that is effective when administered alone or in combination as an antimicrobial agent. For example, an effective amount refers to an amount of the compound or tautomer thereof, or a pharmaceutically acceptable salt said compound or tautomer that is present in a composition, a formulation given to a recipient patient or subject sufficient to elicit biological activity.

In the specification, the singular forms also include the plural, unless the context clearly dictates otherwise. Unless defined otherwise, all technical and scientific terms used herein have the same meaning as commonly understood by one of ordinary skill in the art to which this disclosure belongs. In the case of conflict, the present specification will control. As used herein, "mammal" refers to human and non-human patients.

As used herein, the term "formulae of the disclosure" or "formulae disclosed herein" includes one or more of the Formulae: (I), (Ia), (Ia-1), (Ia-2), (Ib-a), (Ib), (Ia-3), (Ic), (Ic-1), (Id), (Ie), (If), (Ig). (Ie-1), (Ih), (Ii), (Ij), and (Ik).

As used herein, the term "compound of the disclosure" or "compound disclosed herein" includes one or more compounds of the formulae of the disclosure or a compound explicitly disclosed herein.

All percentages and ratios used herein, unless otherwise indicated, are by weight.

Throughout the description, where compositions are described as having, including, or comprising specific components, or where processes are described as having, including, or comprising specific process steps, it is contemplated that compositions of the present disclosure also consist essentially of, or consist of, the recited components, and that the processes of the present disclosure also consist essentially of, or consist of, the recited processing steps. Further, it should be understood that the order of steps or order for performing certain actions are immaterial so long as the invention remains operable. Moreover, two or more steps or actions can be conducted simultaneously.

2. Compounds of the Disclosure

The present application provides compounds of Formula I

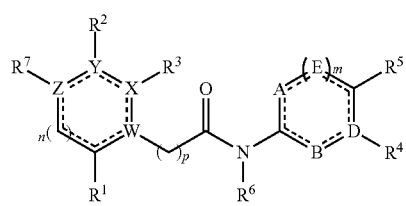

or pharmaceutically acceptable salts thereof, wherein:
A is CH or O;
B is CH or N;

D is C or N;
E is CH or N;
W is C or N;
X is C or N;
Y is C or N;
Z is C or N;
$R^1$ is H, $C_{1-4}$ alkyl, phenyl, or $hetAr^1$;
$R^2$ is H;
$R^3$ is H;
or $R^2$ and $R^3$, together with Y and X, form a 6-membered cycloalkyl ring;
$R^7$ is H;
or, optionally, when n is 0, $R^1$ and $R^7$, together with the atoms to which they are attached, form a 6-membered cycloalkyl ring;
$R^4$ is H, $C_{1-4}$ alkyl, halogen, $CF_3$, or phenyl;
$R^5$ is H, $C_{1-4}$ alkyl, $C_{4-10}$ cycloalkyl, phenyl optionally substituted with halogen, $(C_{1-3}$ alkyl)O($C_{4-6}$ cycloalkyl), O($C_{1-4}$ alkyl)($C_{4-6}$ cycloalkyl), S($C_{1-4}$ alkyl), S($C_{4-6}$ cycloalkyl), $(C_{1-3}$ alkyl)($C_{4-9}$ $hetCyc^1$), $hetAr^1$, or O(phenyl) optionally substituted with CN;
$R^6$ is H or $C_{1-4}$ alkyl;
$hetAr^1$ is a 6-membered heteroaryl ring having 1-3 ring nitrogen atoms optionally substituted with $C_{1-4}$ alkyl;
$hetCyc^1$ is a 6-10-membered bicyclic ring having at least one ring heteroatom which is nitrogen and at least one of the rings is aromatic;
n is 0 or 1;
m is 0 or 1;
p is 0 or 1; and
the dashed lines can be single or double bonds.

In some embodiments, A is CH. In some embodiments, A is O.

In some embodiments, B is CH. In some embodiments, B is N.

In some embodiments, A is O and B is N.

In some embodiments, D is C. In some embodiments, D is N.

In some embodiments, E is CH. In some embodiments, E is N.

In some embodiments, W is N. In some embodiments, W is C.

In some embodiments, X is C.

In some embodiments, Y is C. In some embodiments, Y is N.

In some embodiments, Z is N. In some embodiments, Z is C.

In some embodiments, $R^1$ is H. In some embodiments, $R^1$ is $C_{1-4}$ alkyl or $hetAr^1$. In some embodiments, $R^1$ is methyl, isopropyl, phenyl, or pyridine.

In some embodiments, $R^4$ is H. In some embodiments, $R^4$ is $C_1$, $CF_3$, methyl or phenyl.

In some embodiments, $R^5$ is H or phenyl optionally substituted with halogen.

In some embodiments, $R^5$ is phenyl substituted with F. In some embodiments, $R^5$ is $(C_{1-3}$ alkyl)O($C_{4-6}$ cycloalkyl), O($C_{1-4}$ alkyl)($C_{4-6}$ cycloalkyl), or O(phenyl) optionally substituted with CN. In some embodiments, $C_{4-6}$ cycloalkyl is cyclopentyl or cyclohexyl. In some embodiments, $R^5$ is $(C_{1-3}$ alkyl)O(cyclopentyl) or O($C_{1-4}$ alkyl)($C_{4-6}$ cyclohexyl). In some embodiments, $R^5$ is $C_{1-4}$ alkyl, $C_{4-10}$ cycloalkyl, or $(C_{1-3}$ alkyl)($C_{4-9}$ $hetCyc^1$). In some embodiments, $hetCyc^1$ is a 9-membered bicyclic ring having one or more nitrogen atoms. In some embodiments, $hetCyc^1$ is isoindoline. In some embodiments, $R^5$ is S($C_{1-4}$ alkyl) or S($C_{4-6}$ cycloalkyl). In some embodiments, $C_{4-6}$ cycloalkyl is cyclopentyl or cyclohexyl. In some embodiments, $R^5$ is $hetAr^1$. In some embodiments, $hetAr^1$ is pyridine or pyrimidine optionally substituted with $C_{1-4}$ alkyl.

In some embodiments, $R^6$ is H.
In some embodiments, n is 0.
In some embodiments, m is 1.
In some embodiments, p is 0. In some embodiments, p is 1.

In some embodiments, provided is a compound of Formula I, or a pharmaceutically acceptable salt thereof, wherein:
A is CH;
B is CH;
D is C;
E is CH;
W is N;
X is C;
Y is C;
Z is N;
$R^1$ is H, methyl, isopropyl, phenyl, or a 6-membered heteroaryl ring having 1 ring nitrogen atom;
$R^4$ is H, halogen, methyl, or $CF_3$;
$R^5$ is H or phenyl;
$R^6$ is H;
$R^7$ is H;
m is 1;
n is 0; and
p is 1.

In some embodiments, provided is a compound of Formula I, or a pharmaceutically acceptable salt thereof, wherein:
A is CH;
B is CH;
D is C;
E is CH;
W is N;
X is C;
Y is C;
Z is N;
$R^1$ is H;
$R^4$ is H;
$R^5$ is $(C_{1-3}$ alkyl)O(cyclopentyl), O($C_{1-4}$ alkyl)(cyclohexyl), $C_{1-4}$ alkyl, $C_{4-10}$ cycloalkyl, $(C_{1-3}$ alkyl)($C_{4-9}$ $hetCyc^1$), S($C_{1-4}$ alkyl) S($C_{4-6}$ cyclopentyl) or O(phenyl) optionally substituted with CN;
$R^6$ is H;
$R^7$ is H;
m is 1;
n is 0; and
p is 1.

In some embodiments, provided is a compound of Formula I, or a pharmaceutically acceptable salt thereof, wherein:
A is CH;
B is CH;
D is C;
E is CH;
W is C;
X is C;
Y is C;
Z is N;
$R^1$ is H;
$R^4$ is H;
$R^5$ is phenyl;
$R^6$ is H;
$R^7$ is H;
m is 1;
n is 1; and
p is 1.

In some embodiments, provided is a compound of Formula I, or a pharmaceutically acceptable salt thereof, wherein:
A is O;
B is N;
D is C;
E is CH;
W is N;
X is C;
Y is C;
Z is N;
$R^1$ is H;
$R^4$ is phenyl;
$R^5$ is H;
$R^6$ is H;
$R^7$ is H;
m is 0;
n is 0; and
p is 1.

In some embodiments, provided is a compound of Formula I, or a pharmaceutically acceptable salt thereof, wherein:
A is CH;
B is CH;
D is C;
E is CH;
W is N;
X is N;
Y is N;
Z is N;
$R^1$ is $C_{1-4}$ alkyl;
$R^4$ is H;
$R^5$ is phenyl;
$R^6$ is H;
$R^7$ is H;
m is 1;
n is 0; and
p is 1.

In some embodiments, provided is a compound of Formula I, or a pharmaceutically acceptable salt thereof, wherein:
A is CH;
B is CH;
D is C;
E is CH;
W is N;
X is C;
Y is C;
Z is N;
$R^1$ is $C_{1-4}$ alkyl;
$R^2$ and $R^3$, together with Y and X, form a 6-membered cycloalkyl ring;
$R^4$ is H;
$R^5$ is phenyl;
$R^6$ is H;
$R^7$ is H;
m is 1;
n is 0; and
p is 1.

In some embodiments, provided is a compound of Formula I, or a pharmaceutically acceptable salt thereof, wherein:
A is CH;
B is CH;
D is C;
E is CH;
W is N;
X is C;
Y is C;
Z is N;
$R^1$ is H;
$R^2$ and $R^3$, together with Y and X, form a 6-membered cycloalkyl ring;
$R^4$ is H or methyl;
$R^5$ is pyridine or pyrimidine substituted with $C_{1-4}$ alkyl (e.g., methyl);
$R^6$ is H;
$R^7$ is H;
m is 1;
n is 0; and
p is 1.

In some embodiments, provided is a compound of Formula I, or a pharmaceutically acceptable salt thereof, wherein:
A is CH;
B is CH;
D is C;
E is CH;
W is C;
X is C;
Y is N;
Z is C;
$R^3$ is H;
$R^1$ and $R^7$, together with the atoms to which they are attached, form a 6-membered cycloalkyl ring;
$R^4$ is H;
$R^5$ is phenyl;
$R^6$ is H;
m is 1;
n is 0; and
p is 0.

In some embodiments, provided is a compound of Formula I, or a pharmaceutically acceptable salt thereof, wherein:
A is CH;
B is N;
D is C;
E is CH;
W is N;
X is C;
Y is C;
Z is N;
$R^1$ is H;
$R^2$ and $R^3$, together with Y and X, form a 6-membered cycloalkyl ring;
$R^4$ is H;
$R^5$ is phenyl;
$R^6$ is H;
$R^7$ is H;
m is 1;
n is 0; and
p is 1.

In some embodiments, provided is a compound of Formula I, or a pharmaceutically acceptable salt thereof, wherein:
A is CH;
B is CH or N;
D is N;
E is CH or N;
W is N;
X is C;
Y is C;
Z is N;
$R^1$ is H;

$R^2$ and $R^3$, together with Y and X, form a 6-membered cycloalkyl ring;
$R^5$ is phenyl optionally substituted with halogen (e.g., fluoro);
$R^6$ is H;
$R^7$ is H;
m is 1;
n is 0; and
p is 1.
In some embodiments, the compound of Formula I is selected from the group consisting of:
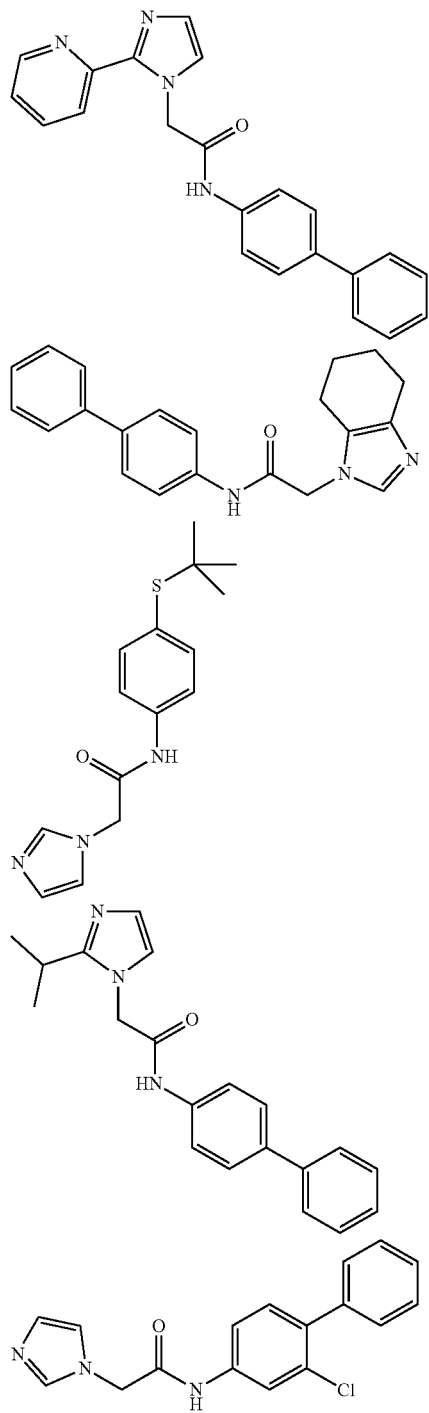
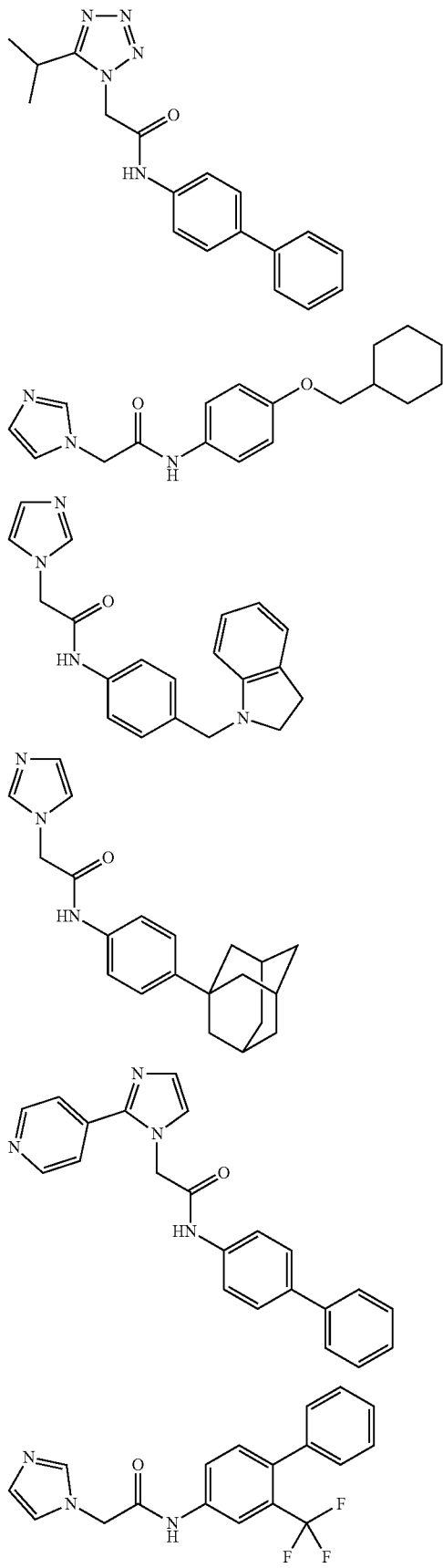
-continued

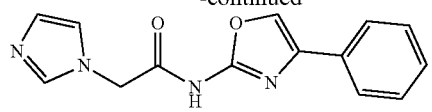
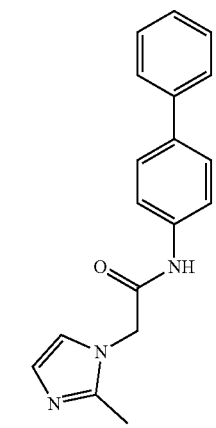
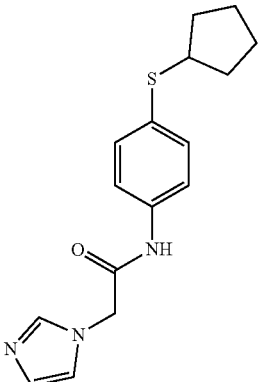
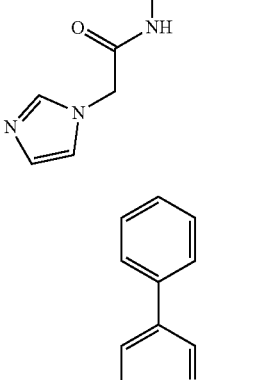
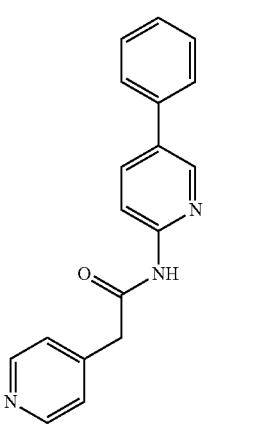
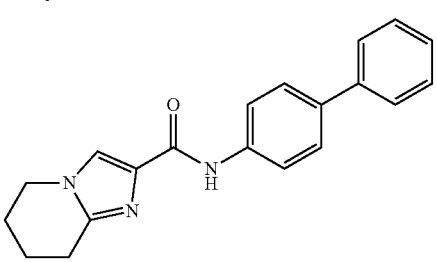
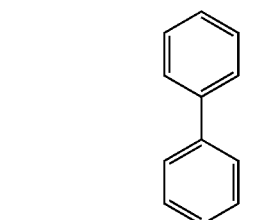
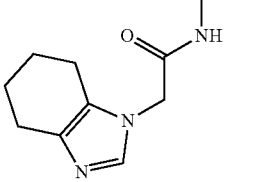
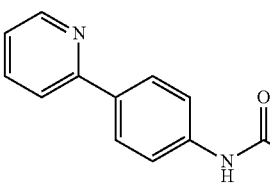
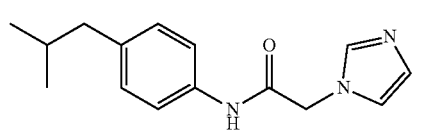
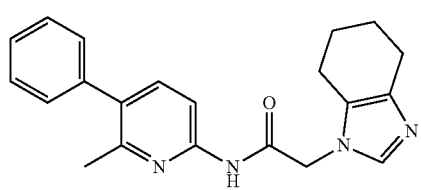

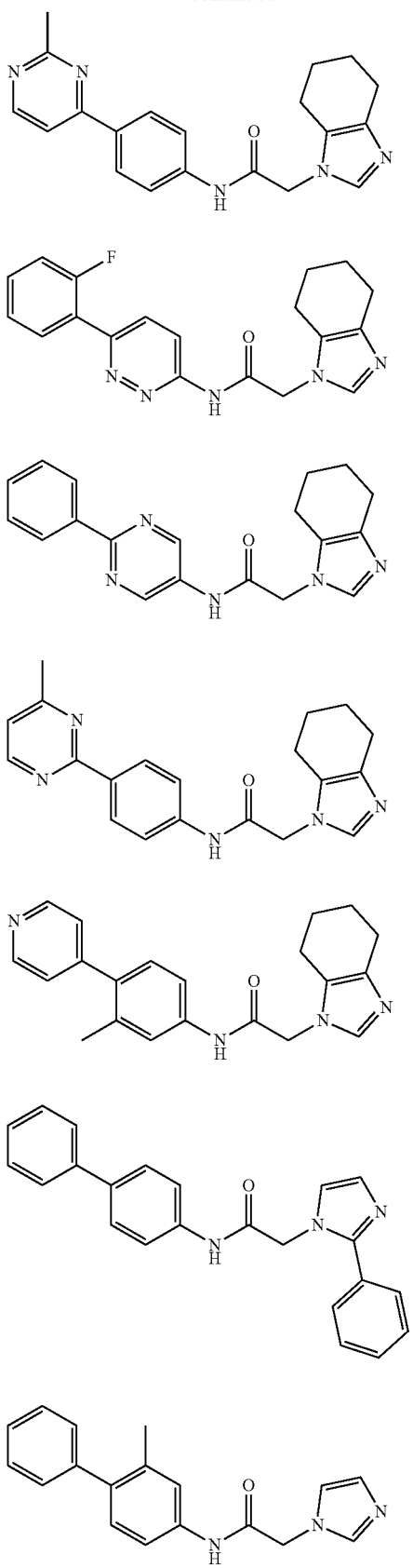
or a pharmaceutically acceptable salt thereof.
In some embodiments, the compound of Formula I is any one of the compounds listed in Table 1, or a pharmaceutically acceptable salt of the compound.
TABLE 1
| # | Structure |
|---|---|
| 1 | 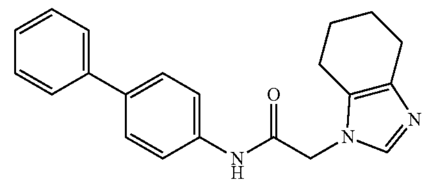 [SMILES: O=C(Cn1cnc2c1CCCC2)Nc1ccc(-c2ccccc2)cc1] |
| 2 | 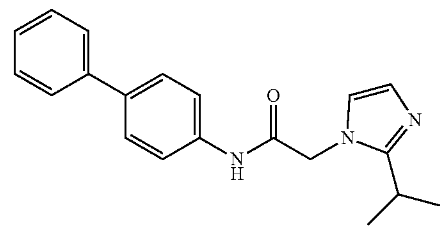 [SMILES: CC(C)c1nccn1CC(=O)Nc1ccc(-c2ccccc2)cc1] |
| 3 | 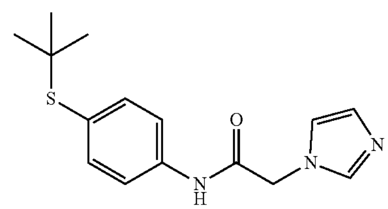 [SMILES: CC(C)(C)Sc1ccc(NC(=O)Cn2ccnc2)cc1] |
| 4 | 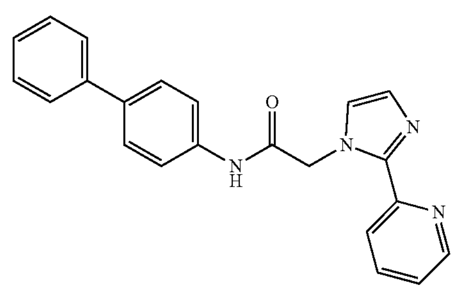 [SMILES: O=C(Cn1ccnc1-c1ccccn1)Nc1ccc(-c2ccccc2)cc1] |
| 5 | 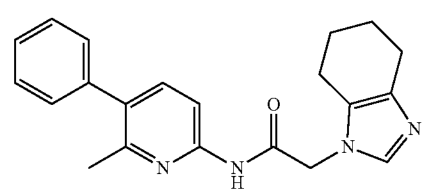 [SMILES: Cc1nc(NC(=O)Cn2cnc3c2CCCC3)ccc1-c1ccccc1] |
| 6 | 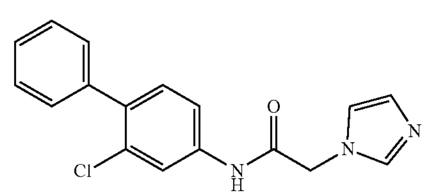 [SMILES: O=C(Cn1ccnc1)Nc1ccc(-c2ccccc2)c(Cl)c1] |

TABLE 1-continued

| # | Structure |
|---|---|
| 7 | (biphenyl)-NH-C(=O)-CH2-(5-isopropyl-tetrazol-1-yl) |
| 8 | (4-(cyclohexylmethoxy)phenyl)-NH-C(=O)-CH2-(imidazol-1-yl) |
| 9 | (4-((indolin-1-yl)methyl)phenyl)-NH-C(=O)-CH2-(imidazol-1-yl) |
| 10 | (4-(adamantan-1-yl)phenyl)-NH-C(=O)-CH2-(imidazol-1-yl) |
| 11 | (biphenyl)-NH-C(=O)-CH2-(2-(pyridin-4-yl)imidazol-1-yl) |
| 12 | (2'-trifluoromethylbiphenyl-4-yl)-NH-C(=O)-CH2-(imidazol-1-yl) |
| 13 | (4-phenyloxazol-2-yl)-NH-C(=O)-CH2-(imidazol-1-yl) |
| 14 | (4-phenoxyphenyl)-NH-C(=O)-CH2-(imidazol-1-yl) |
| 15 | (4-((cyclopentyloxy)methyl)phenyl)-NH-C(=O)-CH2-(imidazol-1-yl) |
| 16 | (4-(4-cyanophenoxy)phenyl)-NH-C(=O)-CH2-(imidazol-1-yl) |
| 17 | (4-isobutylphenyl)-NH-C(=O)-CH2-(imidazol-1-yl) |
| 18 | (4-(cyclopentylthio)phenyl)-NH-C(=O)-CH2-(imidazol-1-yl) |
| 19 | (biphenyl)-NH-C(=O)-CH2-(2-methylimidazol-1-yl) |
| 20 | (biphenyl)-NH-C(=O)-CH2-(pyridin-4-yl) |
| 21 | (biphenyl)-NH-C(=O)-(5,6,7,8-tetrahydroimidazo[1,2-a]pyridin-2-yl) |
| 22 | (5-phenylpyridin-2-yl)-NH-C(=O)-CH2-(4,5,6,7-tetrahydrobenzimidazol-1-yl) |

TABLE 1-continued

| # | Structure |
|---|---|
| 23 | (pyridin-2-yl-phenyl)-NH-C(=O)-CH2-(tetrahydrobenzimidazole) |
| 24 | (2-methylpyrimidin-4-yl-phenyl)-NH-C(=O)-CH2-(tetrahydrobenzimidazole) |
| 25 | (2-fluorophenyl-pyridazin-3-yl)-NH-C(=O)-CH2-(tetrahydrobenzimidazole) |
| 26 | (2-phenylpyrimidin-5-yl)-NH-C(=O)-CH2-(tetrahydrobenzimidazole) |
| 27 | (4-methylpyrimidin-2-yl-phenyl)-NH-C(=O)-CH2-(tetrahydrobenzimidazole) |
| 28 | (pyridin-4-yl-methylphenyl)-NH-C(=O)-CH2-(tetrahydrobenzimidazole) |
| 29 | (biphenyl)-NH-C(=O)-CH2-(2-phenylimidazole) |
| 30 | (2-methylbiphenyl)-NH-C(=O)-CH2-(imidazole) |

The present application also provides compounds of Formula II $$\underset{R^1}{\overset{W}{\underset{N}{\bigvee}}}\overset{X}{\underset{Y}{\bigvee}} N \underset{R^4}{\overset{(\;)_n}{\bigvee}} Z - R^2 - L - \underset{E}{\overset{A = B}{\underset{(\;)_p}{\bigvee}}} D - R^3$$

or a pharmaceutically acceptable salt thereof, wherein:
A is CH, N, or S;
B is CH, N, O, or S;
D is C or N;
E is CH or N;
L is $C_{1-3}$ alkylene or C(=O);
W is CH, $CH_2$, N, or $NR^a$;
X is CH, $CH_2$, N, or $NR^b$;
Y is CH, $CH_2$ or O;
Z is N or $CR^{2'}$;
$R^1$ is H or $C_{1-3}$ alkyl;
$R^2$ is absent or $C_{1-6}$ alkylene;
$R^{2'}$ is H or $C_{1-6}$ alkyl;
or, when Z is $CR^{2'}$, $R^2$ and $R^{2'}$, together with C, can be taken together to form a $C_{1-6}$ heterocyclic ring;
$R^3$ is H, halogen, $C_{1-3}$ alkyl, $C_{3-6}$ cycloalkyl, or $C_{1-3}$ alkoxy;
$R^4$ is H or $C_{1-3}$ alkyl;
$R^{4'}$ is H or $C_{1-3}$ alkyl;
$R^a$ is H or $C_{1-3}$ alkyl;
$R^b$ is $C_{1-3}$ alkyl;
m is 0, 1, or 2;
n is 1 or 2;
p is 0 or 1; and
the dashed lines can be single or double bonds;
with the proviso that when n is 2, $R^1$ is methyl, D is C, $R^3$ is H, and A, B, and E are all CH, then at least one of W, X, and Y is not $CH_2$.

In some embodiments, A is CH. In some embodiments, A is N. In some embodiments, A is S.

In some embodiments, B is CH. In some embodiments, B is N, O, or S.

In some embodiments, D is C.

In some embodiments, E is CH. In some embodiments, E is N.

In some embodiments, L is $C_{1-3}$ alkylene. In some embodiments, L is methylene.

In some embodiments, W is $CH_2$. In some embodiments, W is N.

In some embodiments, X is CH. In some embodiments, X is $CH_2$. In some embodiments, X is $NR^b$.

In some embodiments, $R^b$ is methyl.

In some embodiments, Y is CH. In some embodiments, Y is $CH_2$.

In some embodiments, Z is N. In some embodiments, Z is $CR^{2'}$.

In some embodiments, $R^2$ is absent. In some embodiments, $R^2$ and $R^{2'}$, together with C, form a 5-membered heterocyclic ring having 1 nitrogen atom.

In some embodiments, $R^1$ is H. In some embodiments, $R^1$ is methyl.

In some embodiments, $R^a$ is H or methyl.

In some embodiments, $R^b$ is methyl.

In some embodiments, $R^3$ is H, halogen, or $C_{3-6}$ cycloalkyl. In some embodiments, $R^3$ is halogen. In some embodiments, $R^3$ is chlorine. In some embodiments, $R^3$ is cyclopropyl.

In some embodiments, $R^4$ and $R^{4'}$ are each H. In some embodiments, $R^4$ and $R^{4'}$ are each methyl.

In some embodiments, m is 1 or 2.

In some embodiments, n is 1. In some embodiments, n is 2.

In some embodiments, p is 0. In some embodiments, p is 1.

In some embodiments, provided is a compound of Formula II, or a pharmaceutically acceptable salt thereof, wherein:
A is CH;
B is N, O, or S;
D is C or N;
E is CH or N;
L is $C_{1-3}$ alkylene;
W is $CH_2$;
X is $CH_2$ or $NR^b$;
Y is $CH_2$;
Z is N;
$R^1$ is H or $C_{1-3}$ alkyl;
$R^2$ is absent;
$R^3$ is $C_{1-3}$ alkyl;
$R^4$ is H;
$R^{4'}$ is H;
$R^b$ is $C_{1-3}$ alkyl;
n is 2;
m is 1; and
p is 0.

In some embodiments, provided is a compound of Formula II, or a pharmaceutically acceptable salt thereof, wherein:
A is CH;
B is CH;
D is C;
E is CH;
L is $C_{1-3}$ alkylene;
W is $CH_2$;
X is $NR^b$;
Y is $CH_2$;
Z is N;
$R^1$ is H;
$R^2$ is absent;
$R^3$ is $C_{1-3}$ alkoxy;
$R^4$ is H;
$R^{4'}$ is H;
$R^b$ is $C_{1-3}$ alkyl;
n is 2;
m is 1; and
p is 1.

In some embodiments, provided is a compound of Formula II, or a pharmaceutically acceptable salt thereof, wherein:
A is CH;
B is CH;
D is C;
E is CH;
L is $C_{1-3}$ alkylene;
W is $NR^a$;
X is N;
Y is CH;
Z is N;
$R^1$ is H or $C_{1-3}$ alkyl;
$R^2$ is absent;
$R^3$ is H;
$R^4$ is H;
$R^{4'}$ is H;
$R^a$ is $C_{1-3}$ alkyl;
n is 2;
m is 0; and
p is 1.

In some embodiments, provided is a compound of Formula II, or a pharmaceutically acceptable salt thereof, wherein:
A is CH;
B is CH;
D is C;
E is CH;
L is $C_{1-3}$ alkylene;
W is $NR^a$;
X is $CH_2$;
Y is O;
Z is N;
$R^1$ is H;
$R^2$ is absent;
$R^3$ is H;
$R^4$ is H;
$R^{4'}$ is H;
$R^a$ is H;
n is 2;
m is 1; and
p is 1.

In some embodiments, provided is a compound of Formula II, or a pharmaceutically acceptable salt thereof, wherein:
A is CH;
B is CH;
D is C;
E is CH;
L is C(=O) or $C_{1-3}$ alkylene;
W is $CH_2$;
X is $CH_2$;
Y is $CH_2$;
Z is N;
$R^1$ is $C_{1-3}$ alkyl;
$R^2$ is absent;
$R^3$ is H;
$R^4$ is H or $C_{1-3}$ alkyl;
$R^{4'}$ is H or $C_{1-3}$ alkyl;
n is 1;
m is 1; and
p is 1.

In some embodiments, provided is a compound of Formula II, or a pharmaceutically acceptable salt thereof, wherein:
A is CH;
B is CH;
D is C;
E is CH;
L is $C_{1-3}$ alkylene;
W is $CH_2$;
X is $CH_2$;

Y is CH$_2$;
Z is CR$^{2'}$, and R$^2$ and R$^{2'}$, together with C, are taken together to form a C$_{5-6}$ heterocyclic ring;
R$^1$ is C$_{1-3}$ alkyl;
R$^3$ is H;
R$^4$ is H;
R$^{4'}$ is H;
n is 1;
m is 1; and
p is 1.

In some embodiments, provided is a compound of Formula II, or a pharmaceutically acceptable salt thereof, wherein:
A is CH or S;
B is CH;
D is C;
E is CH;
L is C$_{1-3}$ alkylene;
W is CH$_2$;
X is CH$_2$;
Y is CH$_2$;
Z is N;
R$^1$ is methyl;
R$^2$ is absent;
R$^3$ is H or halogen (e.g., chloro);
R$^4$ is H;
R$^{4'}$ is H;
m is 1;
n is 2; and
p is 0 or 1.

In some embodiments, provided is a compound of Formula II, or a pharmaceutically acceptable salt thereof, wherein:
A is N;
B is O;
D is C;
E is N;
L is C$_{1-3}$ alkylene;
W is CH$_2$;
X is CH$_2$;
Y is CH$_2$;
Z is N;
R$^1$ is methyl;
R$^2$ is absent;
R$^3$ is C$_{3-6}$ cycloalkyl;
R$^4$ is H;
R$^{4'}$ is H;
m is 1;
n is 2; and
p is 0.

In some embodiments, provided is a compound of Formula II, or a pharmaceutically acceptable salt thereof, wherein:
A is CH;
B is CH;
D is C;
E is CH;
L is C$_{1-3}$ alkylene;
W is N;
X is CH;
Y is CH;
Z is N;
R$^1$ is H;
R$^2$ is absent;
R$^3$ is H;
R$^4$ is H;
R$^{4'}$ is H;

m is 1;
n is 2; and
p is 1.

In some embodiments, the compound of Formula II is selected from the group consisting of:

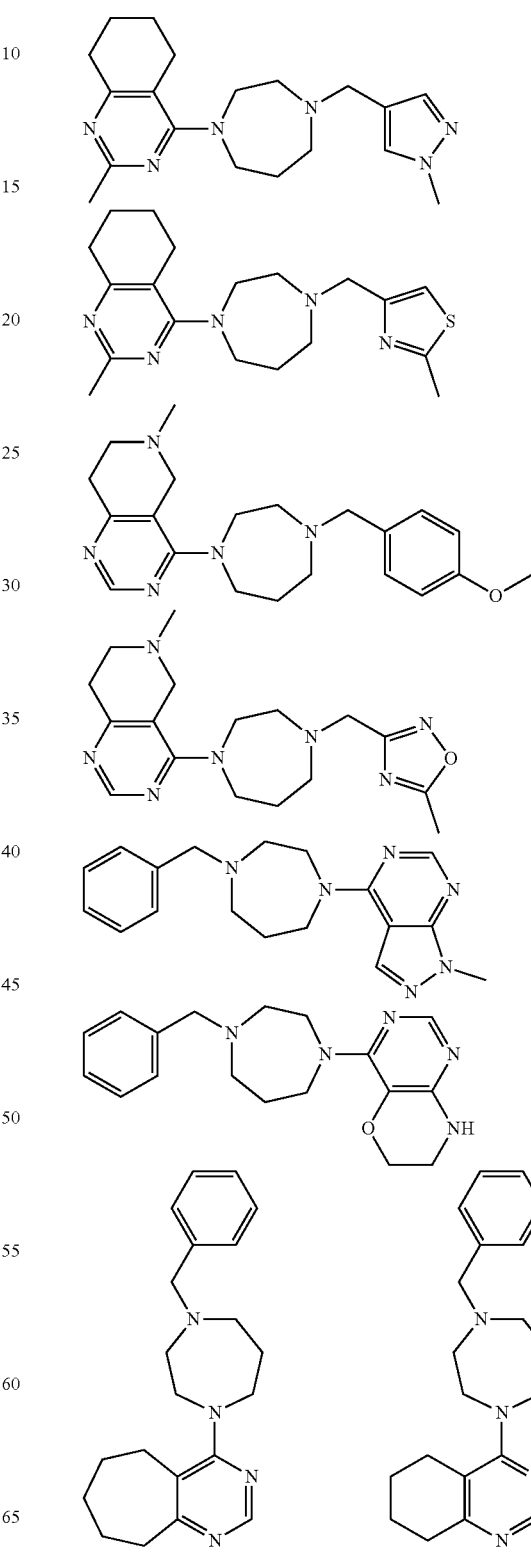

-continued

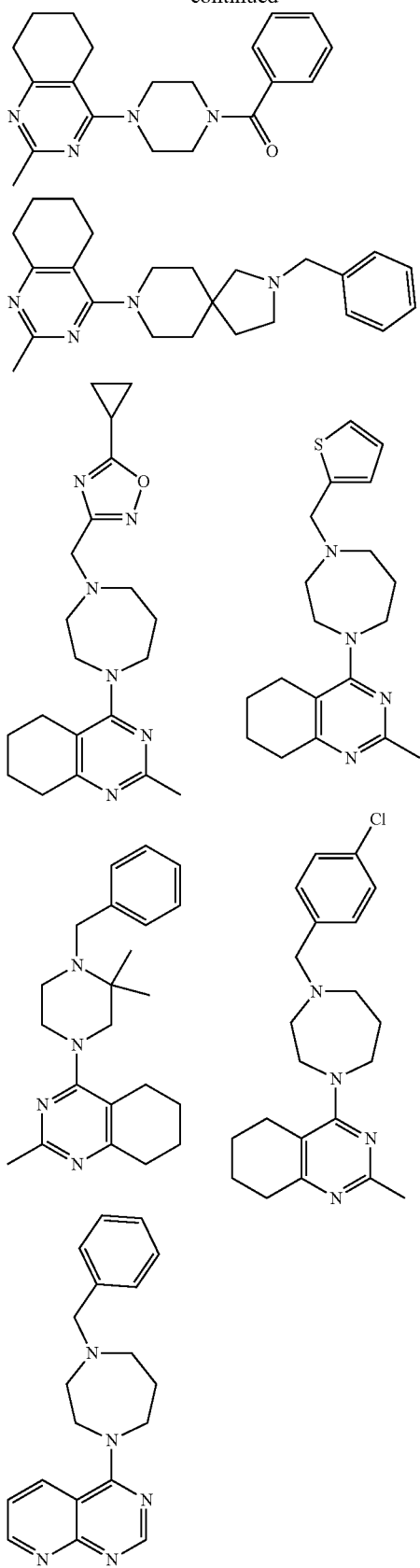

or a pharmaceutically acceptable salt thereof.

In some embodiments, the compound of Formula II is a compound of Formula IIa:

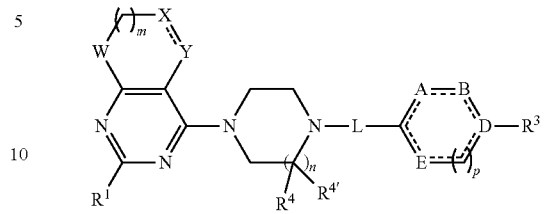

or a pharmaceutically acceptable salt thereof, wherein:
A is CH or N;
B is N, O, or S;
D is C or N;
E is CH or N;
W is $CH_2$ or $NR^a$;
X is CH, $CH_2$, N, or $NR^b$;
Y is CH, $CH_2$ or O;
L is $C_{1-3}$ alkylene or C(=O);
$R^1$ is H or $C_{1-3}$ alkyl;
$R^3$ is $C_{1-3}$ alkyl or $C_{1-3}$ alkoxy;
$R^4$ is H or $C_{1-3}$ alkyl;
$R^{4'}$ is H or $C_{1-3}$ alkyl;
$R^a$ is H or $C_{1-3}$ alkyl;
$R^b$ is $C_{1-3}$ alkyl;
n is 1 or 2;
m is 0, 1 or 2;
p is 0 or 1; and
the dashed lines can be single or double bonds.

In some embodiments, the compound of Formula II is a compound of Formula IIb:

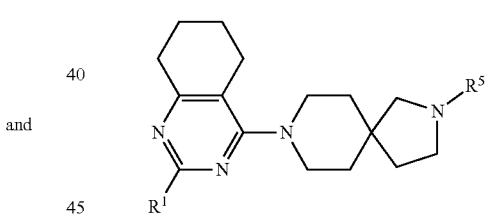

or a pharmaceutically acceptable salt thereof, wherein:
$R^1$ is $C_{1-3}$ alkyl; and
$R^5$ is ($C_{1-3}$ alkyl)phenyl.

In some embodiments, the compound of Formula II is any one of the compounds listed in Table 2, or a pharmaceutically acceptable salt of the compound.

TABLE 2

| # | Structure |
|---|---|
| 31 | 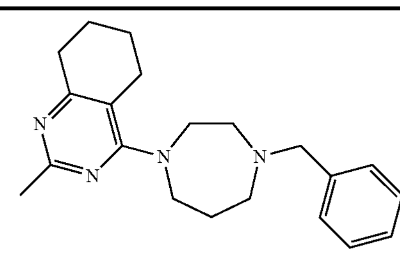 |

TABLE 2-continued
| # | Structure |
|---|---|
| 32 | 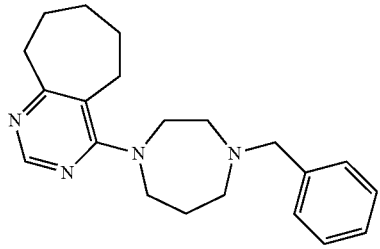 [SMILES: c1ccc(CN2CCCN(c3ncnc4c3CCCCC4)CC2)cc1] |
| 33 | 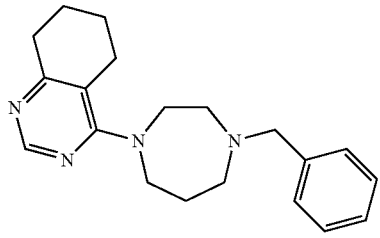 [SMILES: c1ccc(CN2CCCN(c3ncnc4c3CCCC4)CC2)cc1] |
| 34 | 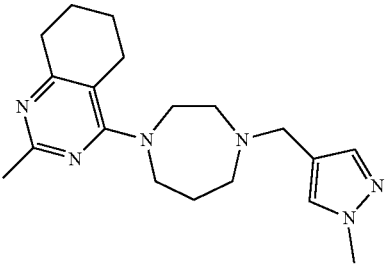 [SMILES: Cc1nc2c(c(N3CCCN(Cc4cnn(C)c4)CC3)n1)CCCC2] |
| 35 | 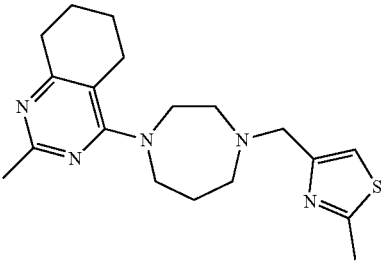 [SMILES: Cc1nc2c(c(N3CCCN(Cc4csc(C)n4)CC3)n1)CCCC2] |
| 36 | 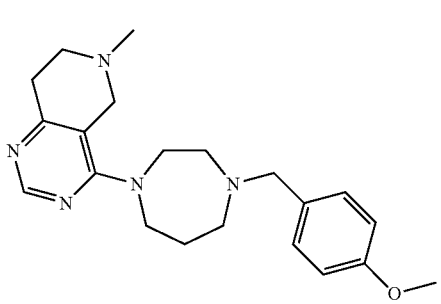 [SMILES: COc1ccc(CN2CCCN(c3ncnc4c3CN(C)CC4)CC2)cc1] |
| 37 | 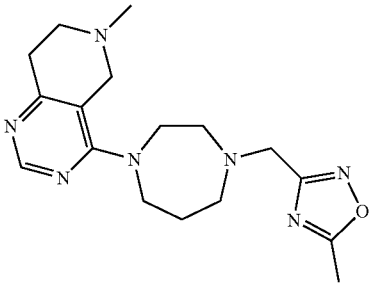 |
| 38 | 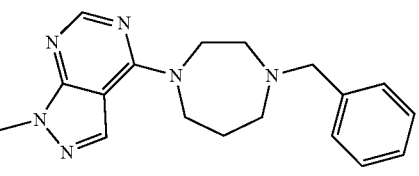 |
| 39 | 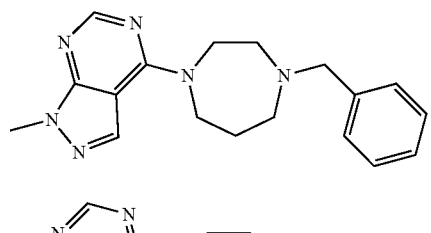 |
| 40 | 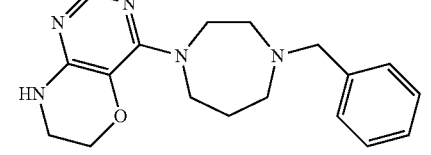 |
| 41 | 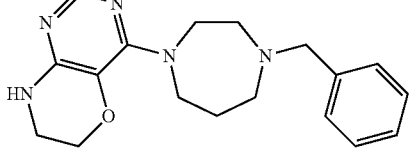 |
| 42 | 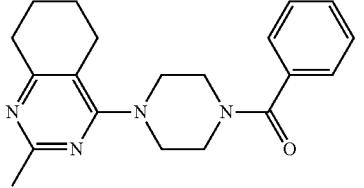 [SMILES: Cc1nc2c(c(N3CCN(C(=O)c4ccccc4)CC3)n1)CCCC2] |
| 43 | 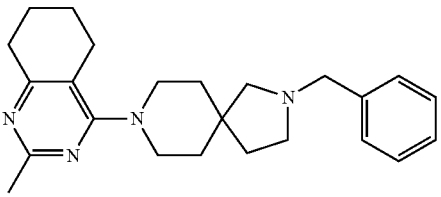 [SMILES: Cc1nc2c(c(N3CCC4(CCN(Cc5ccccc5)C4)CC3)n1)CCCC2] |

TABLE 2-continued

| # | Structure |
|---|---|
| 44 | 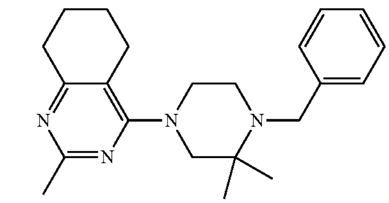 [SMILES: Cc1nc2c(c(N3CCN(Cc4ccccc4)C(C)(C)C3)n1)CCCC2] |
| 45 | 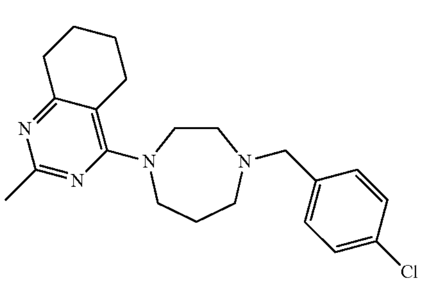 [SMILES: Cc1nc2c(c(N3CCCN(Cc4ccc(Cl)cc4)CC3)n1)CCCC2] |
| 46 | 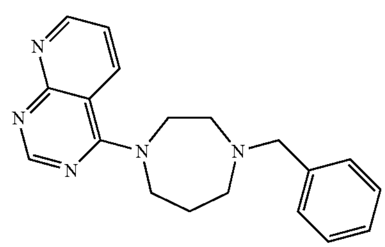 [SMILES: c1ccc(CN2CCCN(c3ncnc4ncccc34)CC2)cc1] |

3. Synthesis of the Compounds of the Disclosure

As will be appreciated, the compounds provided herein, including salts thereof, can be prepared using known organic synthesis techniques and can be synthesized according to any of numerous possible synthetic routes. The compounds thus obtained can be further purified, for example, by flash column chromatography, high performance liquid chromatography, crystallization, or any known purification method.

In one embodiment, compounds of the present disclosure, e.g., compounds of Formula I and Formula II can be synthesized according to the procedures illustrated in synthetic Schemes 1-4 below.

Compounds of Formula I having an imidazopyridine structure can be prepared, for example, using the generalized processes illustrated in Schemes 1 and 2. The proposed synthetic route has three key stages—formation of substituted imidazo[1,2-a]pyridine-2-carbaldehydes (step A), acylation of anilines (step B), and synthesis of final compounds (step C). Step A is well documented in literature (see, e.g., Chavignon et al. (1992) J. Heterocycl. Chem. 29(4):691) and consists of two stages: 1) formation of corresponding 2-(dichloromethyl)imidazo[1,2-a]pyridines by condensation of substituted 2-aminopyridines with 1,1,3-trichloroacetone in 1,2-dimethoxyethane at heating; 2) transformation of 2-(dichloromethyl)imidazo[1,2-a]pyridines at their treatment by calcium carbonate in corresponding imidazo[1,2-a]pyridine-2-carbaldehydes. Step B also has two stages—synthesis of amides of boc-protected aminoacetic acid (R3=H) to avoid formation of side products and the removal of protecting boc-group under acidic conditions. Final step C implies in formation of Schiff bases at the reaction of imidazo[1,2-a]pyridine-2-carbaldehydes with corresponding amines followed by their reduction by sodium borohydride.

In cases when R3=alkane, the synthetic route is shorter and involves 3 stages—alkylation of Alk-substituted aminoacetic acid tert-butyl esters by corresponding 2-(chloromethyl)imidazo[1,2-a]pyridines (step D, Scheme 2), hydrolysis (step E, Scheme 2), and final amides formation (step F, Scheme 2).

Scheme 1

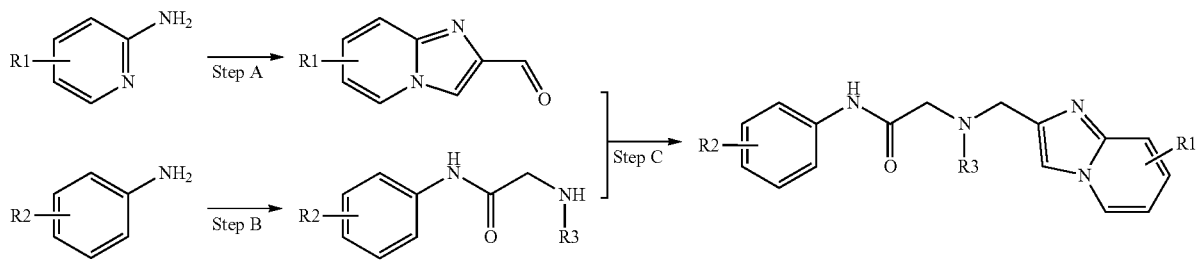

R3 = H Analogues with linker bioisosters

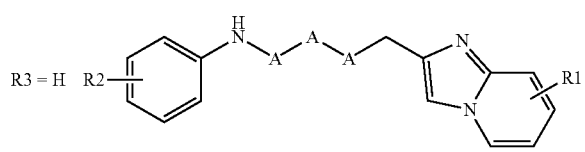

R3 = H

Scheme 2

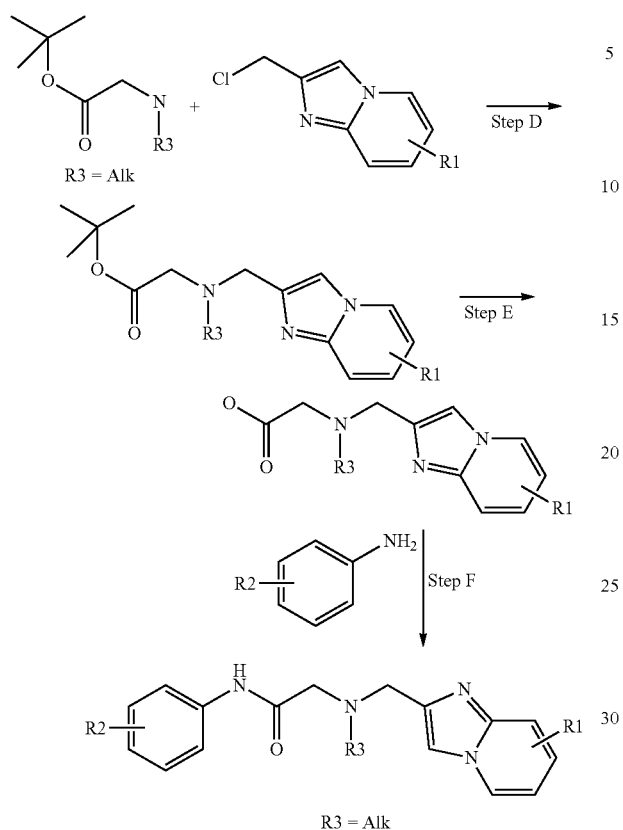

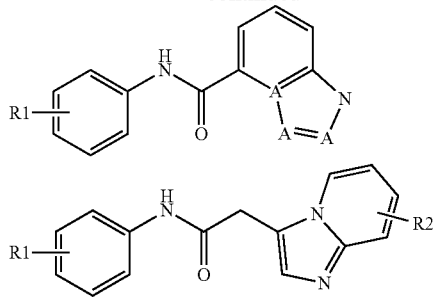

Compounds of Formula II having a pyrimidine/homopiperazine scaffold can be prepared, for example, using the generalized process illustrated in Scheme 4.

Scheme 4

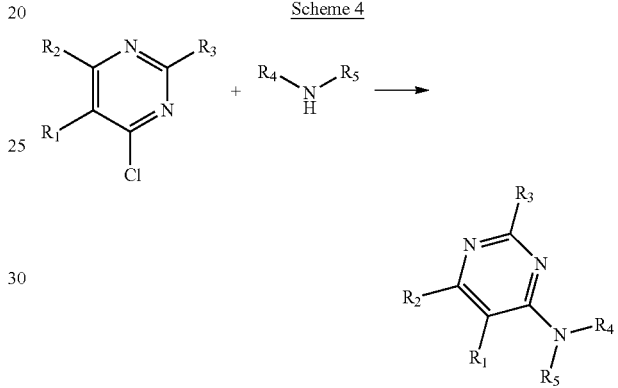

Compounds of Formula I having an imidazole structure can be prepared, for example, using the generalized process illustrated in Scheme 3. The process includes amide bond formation by reaction of corresponding imidazolyl-acetic acids with anilines. Depending on the chemical nature of R1 and R2, different activating agents such as carbodiimides (DCC, EDC), carbonyl diimidazole (CDI) may be used (see, e.g., Montalbetti et al. (2005) Tetrahedron 61:10827).

Scheme 3

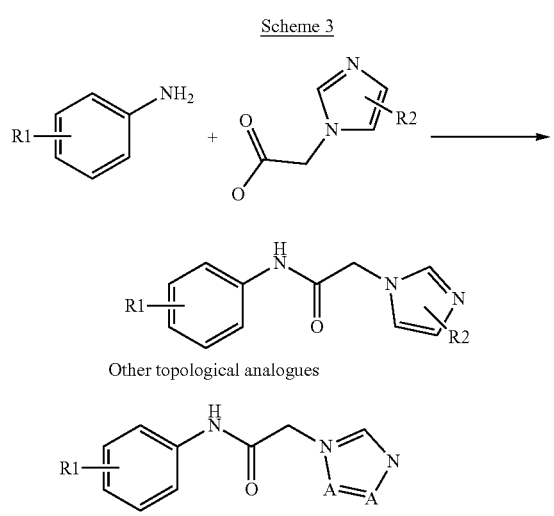

Other topological analogues

It will be appreciated by one skilled in the art that the processes described herein are not the exclusive means by which compounds provided herein may be synthesized and that a broad repertoire of synthetic organic reactions is available to be potentially employed in synthesizing compounds provided herein. The person skilled in the art knows how to select and implement appropriate synthetic routes. Suitable synthetic methods of starting materials, intermediates and products may be identified by reference to the literature, including reference sources such as: Advances in Heterocyclic Chemistry, Vols. 1-107 (Elsevier, 1963-2012); *Journal of Heterocyclic Chemistry* Vols. 1-49 (*Journal of Heterocyclic Chemistry*, 1964-2012); Carreira, et al. (Ed.) *Science of Synthesis, Vols.* 1-48 (2001-2010) and Knowledge Updates KU2010/1-4; 2011/1-4; 2012/1-2 (Thieme, 2001-2012); Katritzky, et al. (Ed.) *Comprehensive Organic Functional Group Transformations*, (Pergamon Press, 1996); Katritzky et al. (Ed.); *Comprehensive Organic Functional Group Transformations II* (Elsevier, 2$^{nd}$ Edition, 2004); Katritzky et al. (Ed.), *Comprehensive Heterocyclic Chemistry* (Pergamon Press, 1984); Katritzky et al., *Comprehensive Heterocyclic Chemistry II*, (Pergamon Press, 1996); Smith et al., *March's Advanced Organic Chemistry*: Reactions, *Mechanisms, and Structure, 6$^{th}$* Ed. (Wiley, 2007); Trost et al. (Ed.), *Comprehensive Organic Synthesis* (Pergamon Press, 1991).

The reactions for preparing compounds described herein can be carried out in suitable solvents which can be readily selected by one of skill in the art of organic synthesis. Suitable solvents can be substantially non-reactive with the starting materials (reactants), the intermediates, or products at the temperatures at which the reactions are carried out, (e.g., temperatures which can range from the solvent's freezing temperature to the solvent's boiling temperature). A given reaction can be carried out in one solvent or a mixture of more than one solvent. Depending on the particular reaction step, suitable solvents for a particular reaction step can be selected by the skilled artisan.

Preparation of compounds described herein can involve the protection and deprotection of various chemical groups. The need for protection and deprotection, and the selection of appropriate protecting groups, can be readily determined by one skilled in the art. The chemistry of protecting groups can be found, for example, in T. W. Greene and P. G. M. Wuts, *Protective Groups in Organic Synthesis*, 3$^{rd}$ Ed., Wiley & Sons, Inc., New York (1999).

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry, or by chromatographic methods such as high performance liquid chromatography (HPLC), liquid chromatography-mass spectroscopy (LCMS), or thin layer chromatography (TLC). Compounds can be purified by those skilled in the art by a variety of methods, including high performance liquid chromatography (HPLC) and normal phase silica chromatography.

Compounds provided herein also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone—enol pairs, amide-imidic acid pairs, lactam—lactim pairs, enamine—imine pairs, and annular forms where a proton can occupy two or more positions of a heterocyclic system, for example, 1H- and 3H-imidazole, 1H-, 2H- and 4H-1,2, 4-triazole, 1H- and 2H-isoindole, and 1H- and 2H-pyrazole. Tautomeric forms can be in equilibrium or sterically locked into one form by appropriate substitution.

All compounds, and pharmaceutically acceptable salts thereof, can be found together with other substances such as water and solvents (e.g., hydrates and solvates) or can be isolated.

In some embodiments, preparation of compounds can involve the addition of acids or bases to affect, for example, catalysis of a desired reaction or formation of salt forms such as acid addition salts.

Example acids can be inorganic or organic acids and include, but are not limited to, strong and weak acids. Some example acids include hydrochloric acid, hydrobromic acid, sulfuric acid, phosphoric acid, p-toluenesulfonic acid, 4-nitrobenzoic acid, methanesulfonic acid, benzenesulfonic acid, trifluoroacetic acid, and nitric acid. Some weak acids include, but are not limited to acetic acid, propionic acid, butanoic acid, benzoic acid, tartaric acid, pyroglutamic acid, gulonic acid, pentanoic acid, hexanoic acid, heptanoic acid, octanoic acid, nonanoic acid, and decanoic acid. Also included are organic diacids such as malonic, fumaric and maleic acid.

Example bases include lithium hydroxide, sodium hydroxide, potassium hydroxide, lithium carbonate, sodium carbonate, potassium carbonate, and sodium bicarbonate. Some example strong bases include, but are not limited to, hydroxide, alkoxides, metal amides, metal hydrides, metal dialkylamides and arylamines, wherein; alkoxides include lithium, sodium and potassium salts of methyl, ethyl and t-butyl oxides; metal amides include sodium amide, potassium amide and lithium amide; metal hydrides include sodium hydride, potassium hydride and lithium hydride; and metal dialkylamides include lithium, sodium, and potassium salts of methyl, ethyl, n-propyl, iso-propyl, n-butyl, tert-butyl, trimethylsilyl and cyclohexyl substituted amides.

In some embodiments, the compounds provided herein, or salts thereof, are substantially isolated. By "substantially isolated" is meant that the compound is at least partially or substantially separated from the environment in which it was formed or detected. Partial separation can include, for example, a composition enriched in the compounds provided herein. Substantial separation can include compositions containing at least about 50%, at least about 60%, at least about 70%, at least about 80%, at least about 90%, at least about 95%, at least about 97%, or at least about 99% by weight of the compounds provided herein, or salt thereof. Methods for isolating compounds and their salts are routine in the art.

The expressions, "ambient temperature" and "room temperature" or "rt" as used herein, are understood in the art, and refer generally to a temperature, e.g. a reaction temperature, that is about the temperature of the room in which the reaction is carried out, for example, a temperature from about 20° C. to about 30° C.

4. Methods of Use

Provided herein are methods of activating the enzymatic activity an E3 ubiquitin ligase in a subject in need thereof. As used herein, the term "subject," refers to any animal, including mammals. For example, mice, rats, other rodents, rabbits, dogs, cats, swine, cattle, sheep, horses, primates, and humans. In some embodiments, the subject is a human. In some embodiments, the method comprises administering to the subject a therapeutically effective amount of a compound provided herein (e.g., a compound of Formula I or Formula II, or a pharmaceutically acceptable salt thereof).

In some embodiments, the subject has diminished E3 ubiquitin ligase enzymatic activity. Examples of E3 ubiquitin ligases include, but are not limited to, Parkin, ARIH1 (HHARI), ARIH2 (TRIAD1), RNF31 (HOIP), RBCK1 (HOIL-1L), MUL1 (MAPL, MULAN), MARCH5 (MITOL), E3A, mdm2, anaphase-promoting complex (APC), UBR5 (EDD1), SOCS, LNXp80, CBX4, CBLL1, HACE1, HECTD1, HECTD2, HECTD3, HECW1, HECW2, HERC1, HERC2, HERC3, HERC4, HUWE1, ITCH, NEDD4, NEDD4L, PPIL2, PRPF19, PIAS1, PIAS2, PIAS3, PIAS4, RANBP2, RNF4, RBX1, SMURF1, SMURF2, STUB1, TOPORS, TRIP12, UBE3A, UBE3B, UBE3C, UBE4A, UBE4B, UBOX5, UBR5, WWP1, and WWP2. In some embodiments, the E3 ubiquitin ligase is Parkin.

In some embodiments of the methods provided herein, the enzymatic activity is activated or enhanced during mitochondrial stress. In some embodiments, the compound, e.g., a compound of Formula I or Formula II, or a pharmaceutically acceptable salt thereof, stimulates mitochondrial quality control. In some embodiments, the compound, e.g., a compound of Formula I or Formula II, or a pharmaceutically acceptable salt thereof, interferes with the auto-inhibition of the ligase.

In some embodiments, the diminished E3 ubiquitin ligase enzymatic activity is due to a disease, aging, or an age-related disorder. Examples of diseases or disorders include, but are not limited to, Parkinson's disease, parkinsonism, Alzheimer's disease, dementia, Amyotrophic lateral sclerosis, Frontotemporal dementia, autism, depression, leprosy, an inclusion body myositis, diabetes mellitus, diabetic kidney disease, a liver disease, a lysosomal storage disorder, a neurological disease, a muscular disease, a mitochondrial disease, and cancer.

In some embodiments, the disease or disorder is Parkinson's disease.

In some embodiments, the disease or disorder is cancer. Example of cancers include, but are not limited to, liver cancer, brain cancer, skin cancer, kidney cancer, lung cancer, colon cancer, pancreatic cancer, hepatocellular carcinoma, glioma, skin cutaneous melanoma, clear cell renal cell carcinoma, non-small cell lung cancer, lung adenocarcinoma, lung squamous cell cancer, colorectal cancer, pancreatic adenocarcinoma, adenoid cystic carcinoma, acute lymphoblastic leukemia, chronic myeloid leukemia, bladder urothelial cancer, head and neck squamous cell carcinoma, esophageal adenocarcinoma, gastric cancer, cervical cancer, thyroid cancer, and endometrioid cancer.

The present application further provides a method treating a disease or disorder associated with diminished E3 ubiquitin ligase enzymatic activity in a subject. In some embodiments, the subject is a human. In some embodiments, the method comprises administering to the subject a therapeutically effective amount of a compound provided herein, e.g., a compound of Formula I or Formula II, or a pharmaceutically acceptable salt thereof.

Provided herein is a method of treating a disease or disorder in a subject. In some embodiments, the subject is a human. In some embodiments, the method comprises:

(a) determining if the disease or disorder is associated with diminished E3 ubiquitin ligase enzymatic activity; and (b) if the disease is determined to be associated with diminished E3 ubiquitin ligase enzymatic activity, administering to the subject a therapeutically effective amount of a compound provided herein, e.g., a compound of Formula I or Formula II, or a pharmaceutically acceptable salt thereof.

In some embodiments, the method of treating a disease or disorder in a subject comprises:

(a) detecting a disease or disorder associated with diminished E3 ubiquitin ligase enzymatic activity; and (b) administering to the subject a therapeutically effective amount of a compound provided herein, e.g., a compound of Formula I or Formula II, or a pharmaceutically acceptable salt thereof.

Provided herein is a method of treating Parkinson's disease in a subject. In some embodiments, the subject is a human. In some embodiments, the method comprises:

(a) determining if the subject has Parkinson's disease; and (b) if the subject has Parkinson's disease, administering to the subject a therapeutically effective amount of a compound provided herein, e.g., a compound of Formula I or Formula II, or a pharmaceutically acceptable salt thereof.

In some embodiments, the method of treating Parkinson's disease in a subject comprises:

(a) detecting Parkinson's disease in a subject; and (b) administering to the subject a therapeutically effective amount of a compound provided herein, e.g., a compound of Formula I or Formula II, or a pharmaceutically acceptable salt thereof.

Provided herein is a method of treating an age-related disorder in a subject. In some embodiments, the subject is a human. In some embodiments, the method comprises:

(a) determining if the subject has an age-related disorder; and (b) if the subject has an age-related disorder, administering to the subject a therapeutically effective amount of a compound provided herein, e.g., a compound of Formula I or Formula II, or a pharmaceutically acceptable salt thereof.

In some embodiments, the method of treating an age-related disorder in a subject comprises:

(a) detecting an age-related disorder in a subject; and (b) administering to the subject a therapeutically effective amount of a compound provided herein, e.g., a compound of Formula I or Formula II, or a pharmaceutically acceptable salt thereof.

Provided herein is a method of treating cancer in a subject. In some embodiments, the subject is a human. In some embodiments, the method comprises:

(a) determining if the subject has cancer; and (b) if the subject has cancer, administering to the subject a therapeutically effective amount of a compound provided herein, e.g., a compound of Formula I or Formula II, or a pharmaceutically acceptable salt thereof.

In some embodiments, the method of treating cancer in a subject comprises:

(a) detecting cancer in a subject; and (b) administering to the subject a therapeutically effective amount of a compound provided herein, e.g., a compound of Formula I or Formula II, or a pharmaceutically acceptable salt thereof.

Example of cancers include, but are not limited to, liver cancer, brain cancer, skin cancer, kidney cancer, lung cancer, colon cancer, pancreatic cancer, hepatocellular carcinoma, glioma, skin cutaneous melanoma, clear cell renal cell carcinoma, non-small cell lung cancer, lung adenocarcinoma, lung squamous cell cancer, colorectal cancer, pancreatic adenocarcinoma, adenoid cystic carcinoma, acute lymphoblastic leukemia, chronic myeloid leukemia, bladder urothelial cancer, head and neck squamous cell carcinoma, esophageal adenocarcinoma, gastric cancer, cervical cancer, thyroid cancer, and endometrioid cancer.

Provided herein are methods of activating the enzymatic activity of an E3 ubiquitin ligase in a cell. In some embodiments, the method comprises contacting the cell with a compound provided herein, e.g., a compound of Formula I or Formula II, or a pharmaceutically acceptable salt thereof. In some embodiments, the contacting is in vitro.

In some embodiments of the methods provided herein, the enzymatic activity is activated or enhanced during mitochondrial stress. In some embodiments, the compound, e.g., a compound of Formula I or Formula II, or a pharmaceutically acceptable salt thereof, stimulates mitochondrial quality control. In some embodiments, the compound, e.g., a compound of Formula I or Formula II, or a pharmaceutically acceptable salt thereof, interferes with the auto-inhibition of the ligase. In some embodiments, the cell has diminished E3 ubiquitin ligase enzymatic activity.

In some embodiments of any of the methods provided herein, the compound (e.g., a compound of Formula I or Formula II) for use in the methods described herein may be used in combination with one or more of the compounds provided and described in the present disclosure.

5. Combination Therapies

In some embodiments, one or more of the compounds provided herein can be administered to a subject in need thereof in combination with at least one additional pharmaceutical agent. In some embodiments, the additional pharmaceutical agent is a compound provided herein (e.g., a compound of Formula I or Formula II).

Additional examples of suitable additional pharmaceutical agents for use in combination with the compounds of the present application for treatment of the diseases or disorders provided herein include, but are not limited to, activators of general autophagy, such as rapamycin and resveratrol (e.g., mTOR pathway inhibition) or AMPK pathway activation (e.g., metformin); activators of lysosomal function/biogenesis, e.g., stimulation of the master regulator TFEB; activators of PINK1 kinase activity, e.g., kinetin; and molecules that activate Parkin by alternative mechanisms, such as phosphor-ubiquitin binding, including phosphor-ubiquitin mimics. In some embodiments, the compounds provided herein may be administered to a subject in need thereof in combination with at least one additional pharmaceutical agent for the treatment of a disease or disorder associated with decreased or diminished E3 ubiquitin ligase activity. In some embodiments, the enzymatic activity is diminished due to a disease, aging, or an age-related disorder.

6. Pharmaceutical Compositions and Formulations

Provided herein are pharmaceutical compositions comprising a compound provided herein (e.g., a compound of Formula I or Formula II, or a pharmaceutically acceptable salt thereof), and at least one pharmaceutically acceptable carrier. When employed as pharmaceuticals, the compounds provided herein can be administered in the form of pharmaceutical compositions; thus, the methods described herein can include administering the pharmaceutical compositions. These compositions can be prepared as described herein or elsewhere, and can be administered by a variety of routes, depending upon whether local or systemic treatment is desired and upon the area to be treated. Administration may be pulmonary (e.g., by inhalation or insufflation of powders or aerosols, including by nebulizer; intratracheal or intranasal), oral, or parenteral. Parenteral administration may include, but is not limited to intravenous, intraarterial, subcutaneous, intraperitoneal, intramuscular injection or infusion; or intracranial, (e.g., intrathecal, intraocular, or intraventricular) administration. Parenteral administration can be in the form of a single bolus dose, or may be, for example, by a continuous perfusion pump. Conventional pharmaceutical carriers, aqueous, powder or oily bases, thickeners and the like may be necessary or desirable. In some embodiments, the compounds provided herein are suitable for oral and parenteral administration. In some embodiments, the compounds provided herein are suitable for oral administration. In some embodiments, the compounds provided herein are suitable for parenteral administration. In some embodiments, the compounds provided herein are suitable for intravenous administration. In some embodiments, the compounds provided herein are suitable for transdermal administration (e.g., administration using a patch or microneedle). Pharmaceutical compositions for topical administration may include transdermal patches (e.g., normal or electrostimulated), ointments, lotions, creams, gels, drops, suppositories, sprays, liquids and powders. Conventional pharmaceutical carriers, aqueous, powder or oily bases, thickeners and the like may be necessary or desirable.

Also provided are pharmaceutical compositions which contain, as the active ingredient, a compound provided herein (e.g., a compound of Formula I or Formula II), or a pharmaceutically acceptable salt thereof, in combination with one or more pharmaceutically acceptable carriers (excipients). In making the compositions provided herein, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments, soft and hard gelatin capsules, suppositories, sterile injectable solutions, and sterile packaged powders.

Some examples of suitable excipients include, without limitation, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include, without limitation, lubricating agents such as talc, magnesium stearate, and mineral oil; wetting agents; emulsifying and suspending agents; preserving agents such as methyl- and propylhydroxy-benzoates; sweetening agents; flavoring agents, or combinations thereof.

The active compound can be effective over a wide dosage range and is generally administered in a pharmaceutically effective amount. It will be understood, however, that the amount of the compound actually administered and the schedule of administration will usually be determined by a physician, according to the relevant circumstances, including the condition to be treated, the chosen route of administration, the actual compound administered, the age, weight, and response of the individual subject, the severity of the subject's symptoms, and the like.

7. Kits

Also provided herein are kits including a compound provided herein, more particularly, a compound of Formula I or Formula II, or a pharmaceutically acceptable salt thereof. In some embodiments, a kit can include one or more delivery systems, e.g., for a compound provided herein, or a pharmaceutically acceptable salt thereof, and directions for use of the kit (e.g., instructions for treating a subject). In some embodiments, a kit can include a compound provided herein, or a pharmaceutically acceptable salt thereof, and one or more additional agents as provided herein.

In some embodiments, the compound is selected from the group of compounds provided in Table 1, or a pharmaceutically acceptable salt thereof. In some embodiments, the compound is selected from the group of compounds provided in Table 2, or a pharmaceutically acceptable salt thereof.

In some embodiments, the kit can include one or more compounds or additional pharmaceutical agents as provided herein, or a pharmaceutically acceptable salt thereof, and a label that indicates that the contents are to be administered to a subject suffering for a disease or disorder associated with diminished or decreased E3 ubiquitin ligase enzymatic activity. In some embodiments, a kit can include one or more compounds as provided herein, or a pharmaceutically acceptable salt thereof, and a label that indicates that the contents are to be administered with one or more additional pharmaceutical agents as provided herein.

EXAMPLES

Example 1: Synthetic Routes

Compounds 1-46, listed in Table 3 below, were synthesized according to the general synthetic schemes described below.

TABLE 3

| Compounds 1-46 | | |
|---|---|---|
| # | Structure | EC$_{50}$ (nM) |
| 1 | biphenyl-NH-C(O)-CH$_2$-(4,5,6,7-tetrahydrobenzimidazol-1-yl) | 371 |
| 2 | biphenyl-NH-C(O)-CH$_2$-(5-isopropylimidazol-1-yl) | 549 |
| 3 | 4-(tert-butylthio)phenyl-NH-C(O)-CH$_2$-(imidazol-1-yl) | 405 |
| 4 | biphenyl-NH-C(O)-CH$_2$-(2-(pyridin-2-yl)imidazol-1-yl) | 164 |
| 5 | (6-methyl-5-phenylpyridin-2-yl)-NH-C(O)-CH$_2$-(4,5,6,7-tetrahydrobenzimidazol-1-yl) | 63 |
| 6 | (2-chloro-4-biphenyl)-NH-C(O)-CH$_2$-(imidazol-1-yl) | 2000 |
| 7 | biphenyl-NH-C(O)-CH$_2$-(5-isopropyltetrazol-1-yl) | 2000 |

TABLE 3-continued

Compounds 1-46

| # | Structure | EC$_{50}$ (nM) |
|---|---|---|
| 8 | 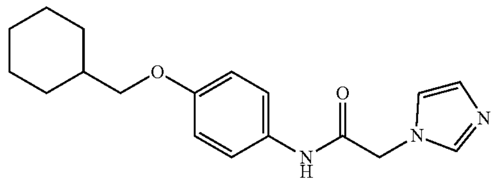 [SMILES: O=C(Cn1ccnc1)Nc1ccc(OCC2CCCCC2)cc1] | 5000 |
| 9 | 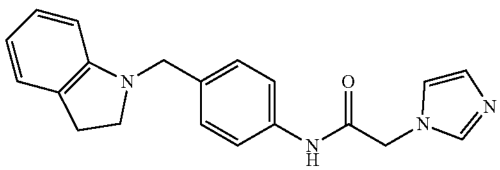 [SMILES: O=C(Cn1ccnc1)Nc1ccc(CN2CCc3ccccc32)cc1] | 5000 |
| 10 | 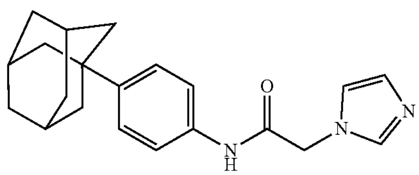 [SMILES: O=C(Cn1ccnc1)Nc1ccc(C23CC4CC(CC(C4)C2)C3)cc1] | 5000 |
| 11 | 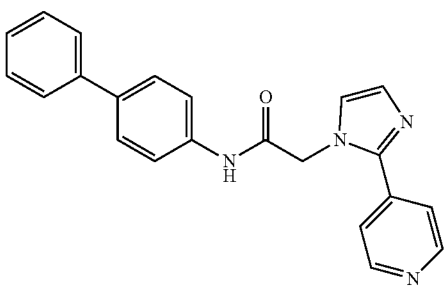 [SMILES: O=C(Cn1ccnc1-c1ccncc1)Nc1ccc(-c2ccccc2)cc1] | 5000 |
| 12 | 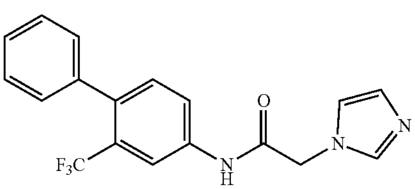 | 5000 |
| 13 | 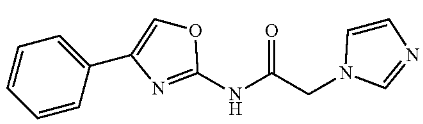 [SMILES: O=C(Cn1ccnc1)Nc1nc(-c2ccccc2)co1] | 5000 |
| 14 | 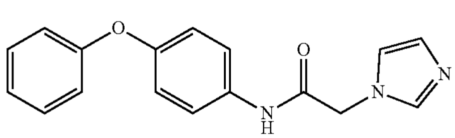 [SMILES: O=C(Cn1ccnc1)Nc1ccc(Oc2ccccc2)cc1] | 5000 |
| 15 | 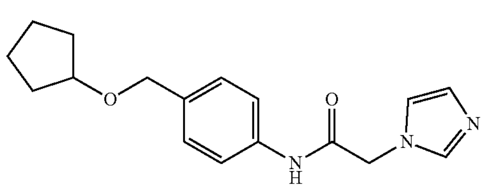 [SMILES: O=C(Cn1ccnc1)Nc1ccc(COC2CCCC2)cc1] | 5000 |

TABLE 3-continued

| # | Structure | EC$_{50}$ (nM) |
|---|---|---|
| 16 | 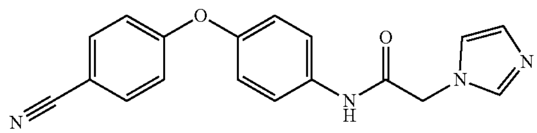 [SMILES: N#Cc1ccc(Oc2ccc(NC(=O)Cn3ccnc3)cc2)cc1] | 5000 |
| 17 | 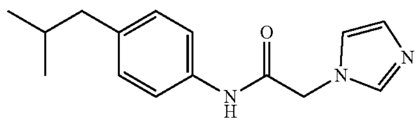 [SMILES: CC(C)Cc1ccc(NC(=O)Cn2ccnc2)cc1] | 5000 |
| 18 | 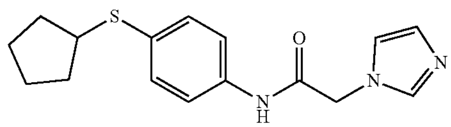 [SMILES: O=C(Cn1ccnc1)Nc1ccc(SC2CCCC2)cc1] | 5000 |
| 19 | 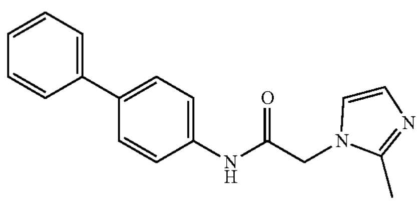 [SMILES: Cc1nccn1CC(=O)Nc1ccc(-c2ccccc2)cc1] | 10000 |
| 20 | 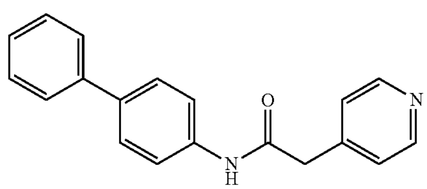 [SMILES: O=C(Cc1ccncc1)Nc1ccc(-c2ccccc2)cc1] | 10000 |
| 21 | 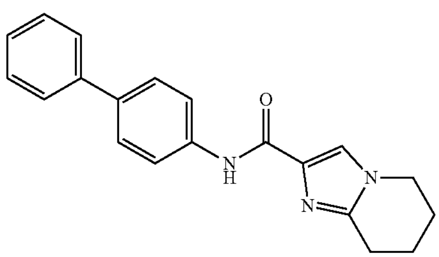 [SMILES: O=C(Nc1ccc(-c2ccccc2)cc1)c1cn2c(n1)CCCC2] | 238 |
| 22 | 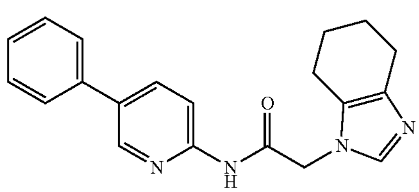 | 246 |
| 23 | 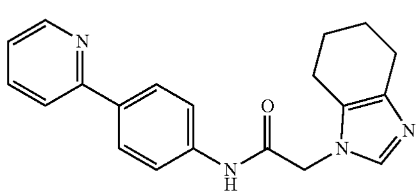 | 272 |

TABLE 3-continued
Compounds 1-46
| # | Structure | EC$_{50}$ (nM) |
|---|---|---|
| 24 | 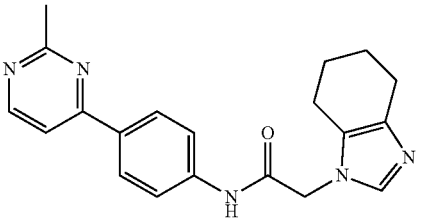 [SMILES: Cc1nccc(-c2ccc(NC(=O)Cn3cnc4c3CCCC4)cc2)n1] | 190 |
| 25 | 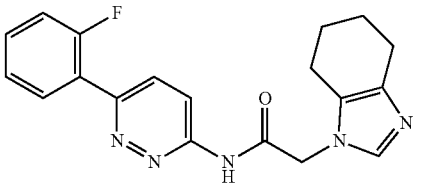 [SMILES: O=C(Cn1cnc2c1CCCC2)Nc1ccc(-c2ccccc2F)nn1] | 382 |
| 26 | 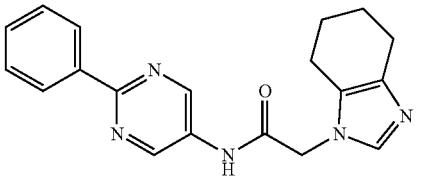 [SMILES: O=C(Cn1cnc2c1CCCC2)Nc1cnc(-c2ccccc2)nc1] | 938 |
| 27 | 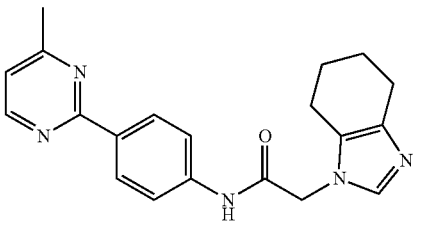 [SMILES: Cc1ccnc(-c2ccc(NC(=O)Cn3cnc4c3CCCC4)cc2)n1] | 190 |
| 28 | 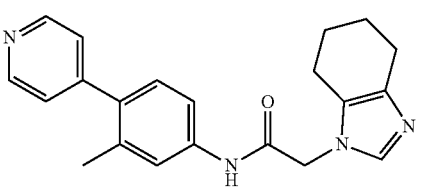 [SMILES: Cc1cc(NC(=O)Cn2cnc3c2CCCC3)ccc1-c1ccncc1] | 134 |
| 29 | 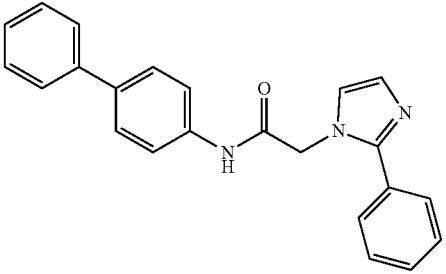 | 2000 |
| 30 | 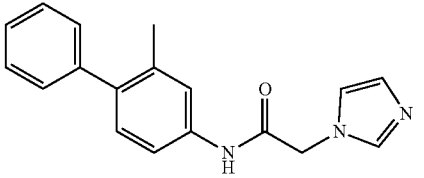 [SMILES: Cc1cc(NC(=O)Cn2ccnc2)ccc1-c1ccccc1] | 5000 |

TABLE 3-continued

| Compounds 1-46 | | |
|---|---|---|
| # | Structure | EC$_{50}$ (nM) |
| 31 | | 990 |
| 32 | | 36 |
| 33 | | 111 |
| 34 | | NA |
| 35 | | 10000 |

TABLE 3-continued

| # | Structure | EC$_{50}$ (nM) |
|---|---|---|
| 36 | 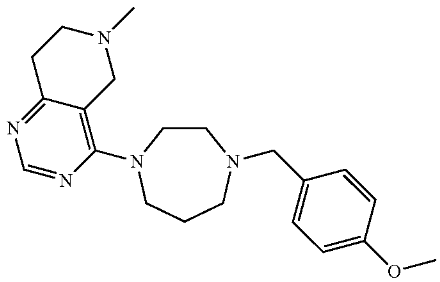 [SMILES: COc1ccc(CN2CCCN(c3ncnc4c3CN(C)CC4)CC2)cc1] | >10000 |
| 37 | 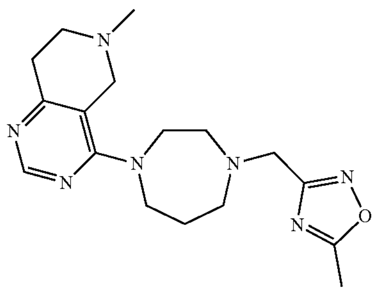 [SMILES: Cc1nc(CN2CCCN(c3ncnc4c3CN(C)CC4)CC2)no1] | NA |
| 38 | 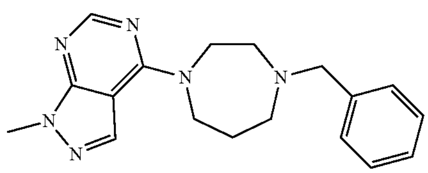 [SMILES: Cn1ncc2c(N3CCCN(Cc4ccccc4)CC3)ncnc21] | NA |
| 39 | 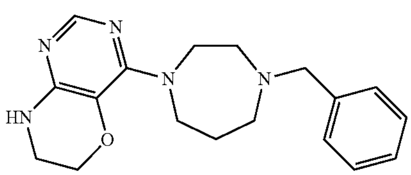 [SMILES: c1ccc(CN2CCCN(c3ncnc4c3OCCN4)CC2)cc1] | NA |
| 40 | 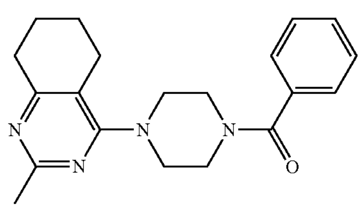 [SMILES: Cc1nc2c(c(N3CCN(C(=O)c4ccccc4)CC3)n1)CCCC2] | >10000 |
| 41 | 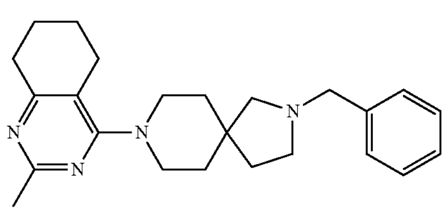 [SMILES: Cc1nc2c(c(N3CCC4(CCN(Cc5ccccc5)C4)CC3)n1)CCCC2] | NA |

TABLE 3-continued
Compounds 1-46
| # | Structure | EC$_{50}$ (nM) |
|---|---|---|
| 42 | 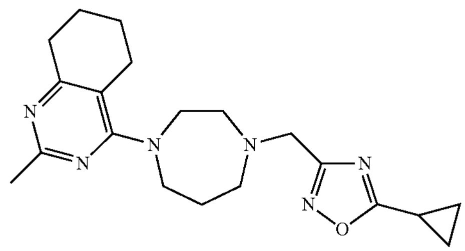 [SMILES: Cc1nc2c(c(N3CCCN(Cc4noc(C5CC5)n4)CC3)n1)CCCC2] | 707 |
| 43 | 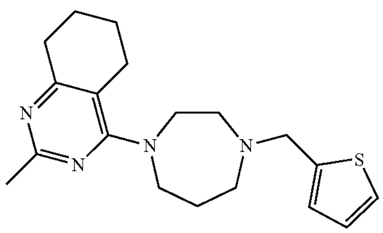 [SMILES: Cc1nc2c(c(N3CCCN(Cc4cccs4)CC3)n1)CCCC2] | 280 |
| 44 | 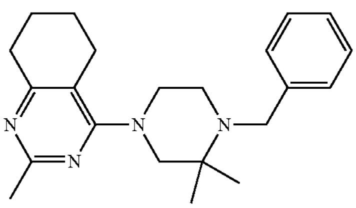 [SMILES: Cc1nc2c(c(N3CCN(Cc4ccccc4)C(C)(C)C3)n1)CCCC2] | 438 |
| 45 | 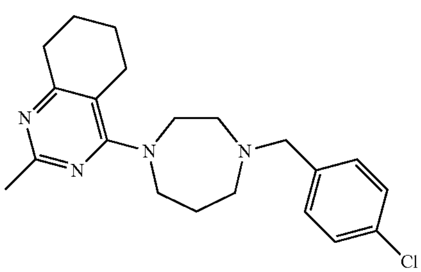 [SMILES: Cc1nc2c(c(N3CCCN(Cc4ccc(Cl)cc4)CC3)n1)CCCC2] | 366 |
| 46 | 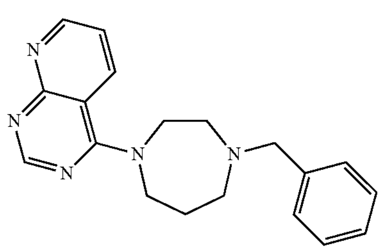 [SMILES: c1ccc(CN2CCCN(c3ncnc4ncccc34)CC2)cc1] | 203 |
A. Synthesis of Compounds 1, 3, 8-10, 12, and 15-20
Compounds 1, 3, 8-10, 12, and 15-20 can be prepared according to the general synthetic scheme below:
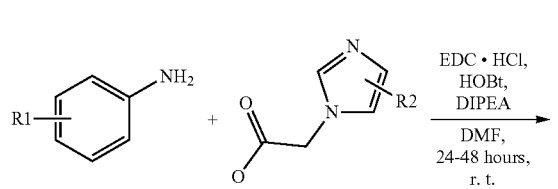
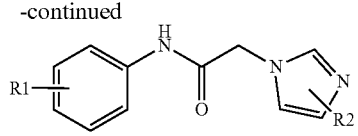
Experimental
A mixture of (3-{[(ethylimino)methylidene]amino} propyl)dimethylamine hydrochloride (EDC·HCl) (1.2 mmol), 1-hydroxybenzotriazole (HOBt) (1.2 mmol), N,N-diisopropylethylamine (0.35 mL, 2 mmol), acid (1.2 mmol), and aniline (1 mmol) in dimethylformamide (7 mL) was stirred for 24-48 hours at room temperature. Then the reaction mixture was treated with water (35 mL), the crude product was filtered and purified by recrystallization from acetonitrile or by HPLC chromatography (methanol/water). Yield: 15-70% depending on the structures of acid and aniline.

The spectral data for each of Compounds 1, 3, 8-10, 12, and 15-20 is listed below:

Compound 1:
$^1$H NMR (DMSO-d$_6$): δ=10.5 (s, 1H, NH), 7.7 (m, 6H, $C_{Ph}$H), 7.4 (m, 3H, $C_{Ph}$H), 7.35 (s, 1H, $C_{imid}$H), 4.85 (s, 2H, CH$_2$), 2.4 (t, 4H, 2CH$_2$), 1.75 (m, 4H, 2CH$_2$) ppm.
LS-MS (m/z): calcd./found for [M+H]$^+$ 332.2/332.2.

Compound 3:
$^1$H NMR (DMSO-d$_6$): δ=10.45 (s, 1H, NH), 7.6 (m, 3H, 2$C_{Ph}$H, $C_{imid}$H), 7.45 (dd, 2H, $C_{Ph}$H), 7.16 (d, 1H, $C_{imid}$H), 6.9 (d, 1H, $C_{imid}$H), 4.9 (s, 2H, CH$_2$), 1.2 (s, 9H, 3CH$_3$) ppm.
LS-MS (m/z): calcd./found for [M+H]$^+$ 290.15/290.2.

Compound 8:
$^1$H NMR (DMSO-d$_6$): δ=10.2 (s, 1H, NH), 7.65 (s, 1H, $C_{imid}$H), 7.45 (dd, 2H, $C_{Ph}$H), 7.15 (d, 1H, $C_{imid}$H), 6.9 (m, 3H, 2$C_{Ph}$H, $C_{imid}$H), 4.85 (s, 2H, CH$_2$), 3.75 (d, 2H, OCH$_2$), 1.75 (m, 6H, 3CH$_2$), 1.2 (m, 3H, CH, CH$_2$), 1.05 (m, 2H, CH$_2$) ppm.
LS-MS (m/z): calcd./found for [M+H]$^+$ 314.21/314.1.

Compound 9:
$^1$H NMR (DMSO-d$_6$): δ=10.35 (s, 1H, NH), 7.65 (s, 1H, $C_{imid}$H), 7.56 (dd, 2H, $C_{Ph}$H), 7.32 (dd, 2H, $C_{Ph}$H), 7.18 (d, 1H, $C_{imid}$H), 7.04 (d, 1H, $C_{Ph}$H), 6.98 (t, 1H, $C_{Ph}$H), 6.9 (d, 1H, $C_{imid}$H), 6.58 (m, 2H, $C_{Ph}$H), 4.8 (s, 2H, CH$_2$), 4.2 (s, 2H, NCH$_2$), 3.25 (t, 2H, CH$_2$), 2.9 (t, 2H, CH$_2$) ppm.
LS-MS (m/z): calcd./found for [M+H]$^+$ 333.19/333.1.

Compound 10:
$^1$H NMR (DMSO-d$_6$): δ=10.25 (s, 1H, NH), 7.65 (s, 1H, $C_{imid}$H), 7.45 (dd, 2H, $C_{Ph}$H), 7.3 (dd, 2H, $C_{Ph}$H), 7.1 (d, 1H, $C_{imid}$H), 6.85 (d, 1H, $C_{imid}$H), 4.9 (s, 2H, CH$_2$), 2.05 (m, 3H, $C_{adam}$H), 1.8 (m, 12H, $C_{adam}$H$_2$) ppm.
LS-MS (m/z): calcd./found for [M+H]$^+$ 336.24/336.1.

Compound 12:
$^1$H NMR (DMSO-d$_6$): δ=10.8 (s, 1H, NH), 8.2 (d, 1H, $C_{Ph}$H), 7.85 (m, 1H, $C_{Ph}$H), 7.65 (s, 1H, $C_{imid}$H), 7.4 (m, 4H, $C_{Ph}$H), 7.3 (m, 2H, $C_{Ph}$H), 7.2 (d, 1H, $C_{imid}$H), 6.9 (d, 1H, $C_{imid}$H), 5.0 (s, 2H, CH$_2$) ppm.
LS-MS (m/z): calcd./found for [M+H]$^+$ 346.3/346.2.

Compound 15:
$^1$H NMR (DMSO-d$_6$): δ=10.35 (s, 1H, NH), 7.65 (s, 1H, $C_{imid}$H), 7.56 (dd, 2H, $C_{Ph}$H), 7.26 (dd, 2H, $C_{Ph}$H), 7.16 (d, 1H, $C_{imid}$H), 6.9 (d, 1H, $C_{imid}$H), 4.9 (s, 2H, CH$_2$), 4.4 (s, 2H, OCH$_2$), 3.9 (m, 1H, CH), 1.65 (m, 6H, CH$_2$), 1.5 (m, 2H, CH$_2$) ppm.
LS-MS (m/z): calcd./found for [M+H]$^+$ 300.19/300.2.

Compound 16:
$^1$H NMR (DMSO-d$_6$): δ=10.55 (s, 1H, NH), 7.9 (dd, 2H, $C_{Ph}$H), 7.7 (dd, 2H, $C_{Ph}$H), 7.65 (s, 1H, $C_{imid}$H), 7.1 (m, 5H, 4$C_{Ph}$H, $C_{imid}$H), 6.9 (d, 1H, $C_{imid}$H), 4.9 (s, 2H, CH$_2$) ppm.
LS-MS (m/z): calcd./found for [M+H]$^+$ 319.12/319.2.

Compound 17:
$^1$H NMR (DMSO-d$_6$): δ=10.2 (s, 1H, NH), 7.65 (s, 1H, $C_{imid}$H), 7.45 (dd, 2H, $C_{Ph}$H), 7.3 (d, 1H, $C_{imid}$H), 7.2 (dd, 2H, $C_{Ph}$H), 6.9 (d, 1H, $C_{imid}$H), 4.9 (s, 2H, CH$_2$), 2.4 (d, 2H, CH$_2$), 1.8 (m, 1H, $C_{isoprop}$H), 0.9 (d, 6H, 2$C_{isoprop}$H$_3$) ppm.
LS-MS (m/z): calcd./found for [M+H]$^+$ 258.18/258.2.

Compound 18:
$^1$H NMR (DMSO-d$_6$): δ=10.35 (s, 1H, NH), 7.65 (s, 1H, $C_{imid}$H), 7.56 (dd, 2H, $C_{Ph}$H), 7.34 (dd, 2H, $C_{Ph}$H), 7.18 (d, 1H, $C_{imid}$H), 6.9 (d, 1H, $C_{imid}$H), 4.9 (s, 2H, CH$_2$), 3.55 (quint, 1H, CH), 2 (m, 2H, CH$_2$), 1.7 (m, 2H, CH$_2$), 1.5 (m, 4H, 2CH$_2$) ppm.
LS-MS (m/z): calcd./found for [M+H]$^+$ 302.15/302.2.

Compound 19:
$^1$H NMR (DMSO-d$_6$): δ=10.5 (s, 1H, NH), 7.7 (m, 6H, $C_{Ph}$H), 7.4 (m, 3H, $C_{Ph}$H), 7.1 (d, 1H, $C_{imid}$H), 6.75 (d, 1H, $C_{imid}$H), 4.85 (s, 2H, CH$_2$), 2.3 (s, 3H, CH$_3$) ppm.
LS-MS (m/z): calcd./found for [M+H]$^+$ 292.16/292.2.

Compound 20:
$^1$H NMR (DMSO-d$_6$): δ=10.5 (s, 1H, NH), 8.55 (d, 2H, $C_{pyr}$H), 7.7 (m, 6H, $C_{Ph}$H), 7.4 (m, 5H, 3$C_{Ph}$H, 2$C_{pyr}$H), 3.8 (s, 2H, CH$_2$) ppm.
LS-MS (m/z): calcd./found for [M+H]+ 289.15/289.0.

B. Synthesis of Compounds 2, 4, 6, 7, 11, and 14

Compounds 2, 4, 6, 7, 11, and 14 may be prepared according to the general synthetic scheme below:

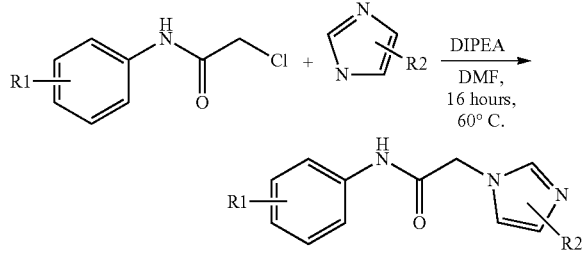

Experimental

A mixture of corresponding 2-chloro-N-phenylacetamide (1 mmol), imidazole (1.5 mmol), N,N-diisopropylethylamine (0.35 ml, 2 mmol) in dimethylformamide (7 mL) was stirred for 16 hours at 60° C. Then the reaction mixture was cooled to room temperature and treated with water (35 ml). The crude product was filtered and purified by recrystallization from acetonitrile or by HPLC chromatography (methanol/water). Yield: 15-70% depending on the structures of the starting materials.

The spectral data for each of Compounds 2, 4, 6, 7, 11, and 14 is listed below:

Compound 2:
$^1$H NMR (DMSO-d$_6$): δ=10.5 (s, 1H, NH), 7.7 (m, 6H, $C_{Ph}$H), 7.5 (m, 2H, $C_{Ph}$H), 7.35 (m, 1H, $C_{Ph}$H), 7.1 (d, 1H, $C_{imid}$H), 6.8 (d, 1H, $C_{imid}$H), 4.95 (s, 2H, CH$_2$), 3.0 (sep, 1H, $C_{isoprop}$H), 1.2 (d, 6H, 2$C_{isoprop}$H$_3$) ppm.
LS-MS (m/z): calcd./found for [M+H]$^+$ 320.2/320.2.

Compound 4:
$^1$H NMR (DMSO-d$_6$): δ=10.5 (s, 1H, NH), 8.5 (d, 1H, $C_{pyr}$H), 8.15 (d, 1H, $C_{pyr}$H), 7.9 (t, 1H, $C_{pyr}$H), 7.65 (m, 6H, $C_{Ph}$H), 7.45 (m, 2H, $C_{Ph}$H), 7.4 (d, 1H, $C_{imid}$H), 7.35 (m, 2H, $C_{Ph}$H, $C_{pyr}$H), 7.1 (d, 1H, $C_{imid}$H), 5.5 (s, 2H, CH$_2$) ppm.
LS-MS (m/z): calcd./found for [M+H]$^+$ 355.17/355.2.

Compound 6:
$^1$H NMR (DMSO-d$_6$): δ=10.55 (s, 1H, NH), 7.9 (t, 1H, $C_{Ph}$H), 7.7 (d, 1H, $C_{Ph}$H), 7.65 (s, 1H, $C_{imid}$H), 7.45 (m, 6H, $C_{Ph}$H), 7.2 (d, 1H, $C_{imid}$H), 6.9 (d, 1H, $C_{imid}$H), 5.0 (s, 2H, CH$_2$) ppm.
LS-MS (m/z): calcd./found for [M+H]$^+$ 312.1/312.2.

Compound 7:
$^1$H NMR (DMSO-d$_6$): δ=10.45 (s, 1H, NH), 7.66 (m, 6H, $C_{Ph}$H), 7.62 (m, 2H, $C_{Ph}$H), 7.46 (m, 5H, $C_{Ph}$H), 7.35 (m, 2H, $C_{Ph}$H, $C_{imid}$H), 7.1 (d, 1H, $C_{imid}$H), 4.95 (s, 2H, CH$_2$) ppm.
LS-MS (m/z): calcd./found for [M+H]$^+$ 354.18/354.1.

Compound 11:

¹H NMR (DMSO-d₆): δ=10.5 (s, 1H, NH), 8.85 (d, 1H, $C_{pyr}$H), 8.6 (d, 1H, $C_{pyr}$H), 8.05 (d, 1H, $C_{pyr}$H), 7.65 (m, 6H, $C_{Ph}$H), 7.45 (m, 3H, $2C_{Ph}$H, $C_{pyr}$H), 7.4 (d, 1H, $C_{imid}$H), 7.3 (m, 1H, $C_{Ph}$H), 7.1 (d, 1H, $C_{imid}$H), 5.05 (s, 2H, CH₂) ppm. LS-MS (m/z): calcd./found for [M+H]⁺ 355.17/355.2.

Compound 14:

¹H NMR (DMSO-d₆): δ=10.55 (s, 1H, NH), 7.62 (m, 2H, $C_{Ph}$H, $C_{imid}$H), 7.57 (m, 1H, $C_{Ph}$H), 7.35 (t, 2H, $C_{pH}$H), 7.06 (m, 2H, $C_{Ph}$H, $C_{imid}$H), 6.95 (m, 4H, $C_{Ph}$H), 6.86 (d, 1H, $C_{imid}$H), 4.85 (s, 2H, CH₂) ppm.

LS-MS (m/z): calcd./found for [M+H]⁺ 294.13/294.2.

C. Synthesis of Compound 30

Compound 30 may be prepared according to the synthetic scheme below:

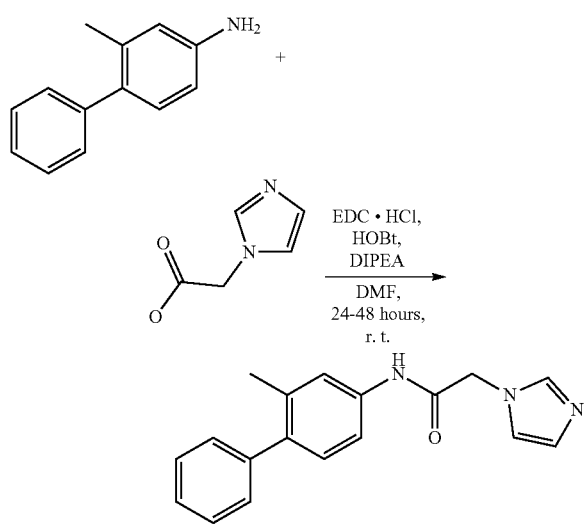

Experimental

A mixture of (3-{[(ethylimino)methylidene]amino}propyl)dimethylamine hydrochloride (EDC·HCl) (1.2 mmol), 1-hydroxybenzotriazole (HOBt) (1.2 mmol), N,N-diisopropylethylamine (0.35 ml, 2 mmol), 2-(1H-imidazol-1-yl)acetic acid (1.2 mmol), and 3-methyl-4-phenylaniline (1 mmol) in dimethylformamide (7 mL) was stirred for 36 hours at room temperature. Then the reaction mixture was treated with water (35 mL), the crude product was filtered and purified by recrystallization from acetonitrile. Yield: 40%.

The spectral data for Compound 30 is listed below:

Compound 30:

¹H NMR (DMSO-d₆): δ=10.55 (s, 1H, NH), 7.65 (s, 1H, $C_{imid}$H), 7.45 (m, 4H, $C_{Ph}$H), 7.37 (m, 3H, $C_{Ph}$H), 7.17 (m, 2H, $C_{Ph}$H, $C_{imid}$H), 6.9 (d, 1H, $C_{imid}$H), 4.9 (s, 2H, CH₂), 2.2 (s, 3H, CH₃) ppm.

LS-MS (m/z): calcd./found for [M+H]⁺ 292.16.1/292.0.

D. Synthesis of Compound 5

Compound 5 may be prepared according to the synthetic scheme below:

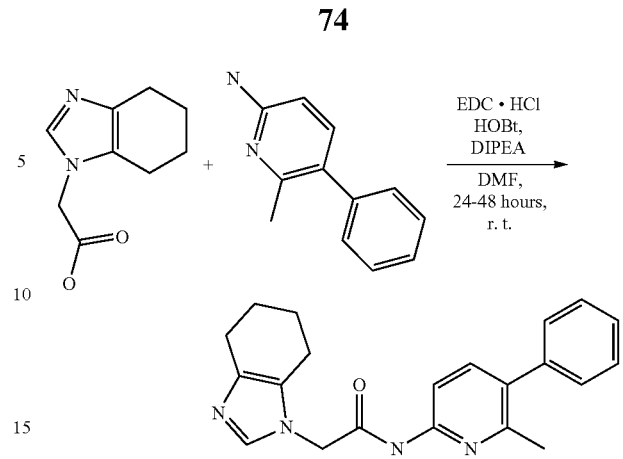

The spectral data from compound 5 is listed below:

Compound 5:

¹H NMR (DMSO-d₆): δ=10.9 (s, 1H, NH), 7.95 (d, 1H, $C_{py}$H), 7.65 (d, 1H, $C_{py}$H), 7.3-7.5 (m, 6H, $C_{Ph}$H; $C_{imid}$H), 4.85 (s, 2H, CH₂CO), 2.4 (m, 4H, 2CH₂; s, 3H, CH₃), 1.7 (m, 4H, 2CH₂) ppm.

LS-MS (m/z): calcd./found for [M+H]⁺ 347.21/347.2.

E. Synthesis of Compound 31

A mixture of 4-chloro-2-methyl-5,6,7,8-tetrahydroquinazoline (0.183 g, 1 mmol), 1-benzyl-1,4-diazepan (0.228 g, 1.2 mmol), and N,N-diisopropylethylamine (0.35 mL, 2 mmol) in dimethylacetamide (7 mL) was stirred for 16 hours at 90° C. Then the reaction mixture was cooled to room temperature and treated with brine (35 mL). The mixture was extracted with ethyl acetate (2×70 mL). The combined organic layers were washed with water (70 mL), brine (70 mL), dried over Na₂SO₄, filtered, and concentrated under reduced pressure. Purification by HPLC chromatography (methanol/water) afforded 0.188 g (0.56 mmol, 56% yield) of Compound 31 as an oil. LS-MS (m/z): calcd./found for [M+H]⁺ 337.48/337.4.

F. Synthesis of Compound 32

Compound 32 may be prepared according to the synthetic scheme below:

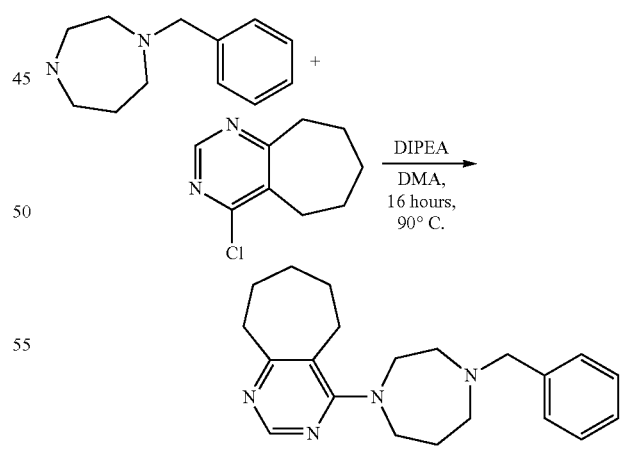

The spectral data from compound 32 is listed below.

Compound 32:

¹H NMR (DMSO-d₆): δ=8.3 (s, 1H, $C_{quin}$H), 7.3 (m, 5H, $C_{Ph}$H), 3.55 (s, 2H, CH₂Ph), 3.5 (m, 4H, 2CH₂), 2.7 (m, 4H, 2CH₂), 2.55 (m, 4H, 2CH₂), 1.85 (m, 2H, CH₂), 1.75 (m, 2H, CH₂), 1.6 (m, 4H, 2CH₂) ppm.

LS-MS (m/z): calcd./found for [M+H]⁺ 337.28/337.2.

G. Synthesis of Compound 33

Compound 33 may be prepared according to the synthetic scheme below:

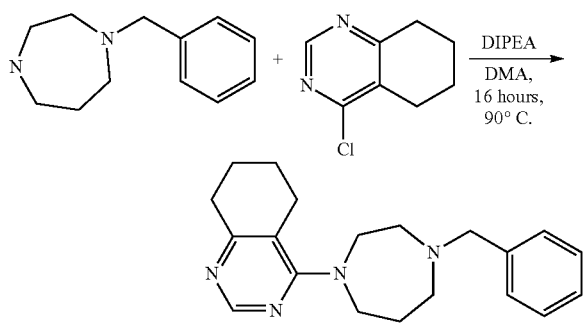

The spectral data from compound 33 is listed below.

Compound 33:

$^1$H NMR (DMSO-d$^6$): δ=8.3 (s, 1H, C$_{quin}$H), 7.3 (m, 5H, C$_{Ph}$H), 3.65 (m, 4H, 2CH$_2$), 3.55 (s, 2H, CH$_2$Ph), 2.7 (m, 4H, 2CH$_2$), 2.55 (m, 4H, 2CH$_2$), 1.85 (m, 2H, CH$_2$), 1.75 (m, 2H, CH$_2$), 1.6 (m, 2H, CH$_2$) ppm.

LS-MS (m/z): calcd./found for [M+H]$^+$ 323.26/323.2.

Example 2: Ames Test of Compounds 1-4 and 31

The bacterial reverse mutation assay (Ames Test) was used to evaluate the mutagenic properties of tested Compounds 1-4 and 31. The test used amino acid-dependent strains of *Salmonella typhimurium* and *Escherichia coli* to detect point mutations which involved substitution, addition or deletion of one or a few DNA base pairs. Point mutations were introduced in the histidine (*Salmonella typhimurium*) or the tryptophan (*Escherichia coli*) operon, making the tester strains incapable of producing these amino acids. The test detected mutations that revert the mutations present in the bacteria, restoring the functional capability to synthesize histidine or tryptophan. The revertant bacteria were detected by the ability to grow in the absence of the amino acid required by the parent test strain. A mutagenic potential of a tested compound was assessed by exposing these bacterial strains to different concentrations of the compounds and estimating number of revertant colonies grown in the absence (trace quantities) of the amino acid.

A. Materials and Equipment

Cell strains used in the assay included the *Salmonella typhimurium* strains TA 98 (Xenometrix PSS-0110), TA 100 (Xenometrix PSS-0111), TA 1535 (Xenometrix PSS-0112), and TA 1537 (Xenometrix PSS-0113), and *Escherichia coli* strains wp2 [pKM101] (Xenometrix PSS-0116) and wp2 uvrA (Xenometrix PSS-0115).

Reagents and consumables included: DMSO (Sigma Cat #34869), DMSO stock solution of the tested compound(s) at 45 mM, magnesium sulfate MgSO$_4$·H$_2$O (Fluka Cat #83266), citric acid monohydrate (Enamine, Ukraine), potassium phosphate dibasic K$_2$HPO$_4$ (Helicon Cat #Am-0348), sodium ammonium phosphate Na$_2$NH$_2$PO$_4$ (Sigma Cat #S9506), D-glucose monohydrate (Sigma Cat #49158), Agar (Sigma Cat #A1296), L-histidine (Sigma Cat #H$_{6034}$), biotin (Sigma Cat #B4639), L-tryptophan (Sigma Cat #T8941), nutrient broth #2 (Oxoid Cat #CV0067), ampicillin (Sigma Cat #A9393), 2-nitrofluorene (Sigma Cat #N16754), 4-nitroquinoline N-oxide (Sigma Cat #N8141), 9-aminoacridine (Enamine, Ukraine; T5111202), sodium azide (Helicon Cat #Am-0639), sodium chloride (Sigma Cat #S3014), magnesium chloride MgCl$_2$·6H$_2$O (Sigma Cat #M2670), 35 mm Petri dish (Corning Cat #430588), and 1.5 mL Eppendorf tubes (Greiner bio-one Cat #616201).

The media used was Vogel-Bonner E medium (7.5 mM MgSO$_4$, 10 mM citric acid monohydrate, 60 mM K$_2$HPO$_4$, 15 mM Na$_2$NH$_2$PO$_4$); GM medium (glucose minimal agar medium) (Vogel-Bonner E medium supplemented with 0.5% glucose, 1.5% agar); GM liquid medium (glucose minimal medium) (Vogel-Bonner E medium supplemented with 0.5% glucose); and Top agar (0.6% agar, 0.6% NaCl, 0.05 mM histidine and 0.05 mM biotin (for *S. typhimurium*) or 0.05 mM tryptophan (for *E. coli*)).

Equipment included an Innova 4080 Incubator Shaker (New Brunswick Scientific, USA), a BioMate 3 UV/Vis spectrophotometer (Thermo Scientific, USA), a Termaks Incubator, B8054 (Termaks, Norway), the water purification system NANOpure Diamond D11911 (Thermo Scientific Barnstead, USA), and pipettors 2-20 µL, 20-100 µL, and 100-1000 µL (Thermo Scientific, USA).

B. Methods

Experiments with a test compound and positive and negative controls were conducted in duplicate on five tester strains (*S. typhimurium*: TA 98, TA 100, TA 1535, TA 1537; and *E. Coli*: wp2[pKM101]+wp2 uvrA mixed 1:2). As the positive controls, compounds with known mutagenic activity were used: 2-nitrofluorene (0.1 µg/plate) for TA 98, 4-nitroquinoline N-oxide (0.02 µg/plate) for TA 100, NaN$_3$ (0.15 µg/plate) for TA 1535, 9-aminoacridine (7.5 µg/plate) for TA 1537, and 4-nitroquinoline N-oxide (0.02 µg/plate) for *E. coli*. DMSO was used as the negative control.

For each experiment, tester strain cultures were grown overnight in Oxoid nutrient broth #2 at 37° C. with shaking at 235 rpm to a density of 1-2×10$^9$ colony forming units/mL (OD$_{540}$~2).

The tester strain (10 µL of night culture) was mixed with the test agent (10 L of the DMSO stock) and GM liquid medium (30 µL). The obtained mixture was incubated at room temperature for 5 min in a sterile 1.5 mL tube. Then, to the tube was added 200 µL of molten top agar stored at 44° C. to prevent solidifying. After mixing with a pipette, the mixture was poured onto the surface of a GM agar plate (2.0 mL of GM agar per plate). After solidifying the top agar, the plate was inverted and incubated at 37° C. for 48 hours. Then, results were expressed as number of revertant colonies per plate.

C. Results

The final concentrations of the tested compounds were determined to be 50 µM, 100 µM and 200 µM. Precipitate was observed in a strain-compound-GM medium mixture in the samples with final concentrations of 200 µM for Compounds 1 and 4.

Tested Compounds 1, 2, 4 and 31 had no mutagenic potential for the tester strains. The test Compound 3 at the concentration of 200 µM revealed mutagenic activity for the tester strains TA 98, TA 1537, TA 1535 and *E. coli*. Compound 3 had mutagenic activity at both 100 and 200 µM for the strain TA 100.

The results are shown in Table 4 below.

TABLE 4

Results of the mutagenicity assay for the tested compounds

| Cell Strain | Conc. (μM) | Mean ± SD Compound 31 | Fold increase (over baseline*) | Mean ± SD Compound 1 | Fold increase (over baseline*) | Mean ± SD Compound 2 | Fold increase (over baseline*) | Mean ± SD Compound 3 | Fold increase (over baseline*) | Mean ± SD Compound 4 | Fold increase (over baseline*) |
|---|---|---|---|---|---|---|---|---|---|---|---|
| TA 98 | 0 | 2.5 ± 0.7 | | 2.5 ± 0.7 | | 2.5 ± 0.7 | | 2.5 ± 0.7 | | 2.5 ± 0.7 | |
| | 200 | 1 ± 1.41 | 0.3 | 0 ± 0 | 0 | 0.5 ± 0.7 | 0.2 | >1000 | >312 | 0 ± 0 | 0 |
| | 100 | 1 ± 0 | 0.3 | 0.5 ± 0.7 | 0.2 | 0.5 ± 0.7 | 0.2 | 0.5 ± 0.7 | 0.2 | 0 ± 0 | 0 |
| | 50 | 0.5 ± 0.7 | 0.2 | 1.5 ± 0.7 | 0.46 | 1 ± 1.41 | 0.3 | 1.5 ± 0.7 | 0.46 | 1.5 ± 0.7 | 0.46 |
| | positive | 7 ± 1.41 | | 7 ± 1.41 | | 7 ± 1.41 | | 7 ± 1.41 | | 7 ± 1.41 | |
| TA 100 | 0 | 5.5 ± 0.7 | | 5.5 ± 0.7 | | 5.5 ± 0.7 | | 5.5 ± 0.7 | | 5.5 ± 0.7 | |
| | 200 | 6 ± 1.41 | 0.97 | 0 ± 0 | 0 | 10 ± 0 | 1.61 | >300 | >48 | 4 ± 1.41 | 0.65 |
| | 100 | 6 ± 0 | 0.97 | 0 ± 0 | 0 | 6 ± 2.83 | 0.97 | >200 | >32 | 7.5 ± 3.54 | 1.2 |
| | 50 | 6.5 ± 0.7 | 1.04 | 0 ± 0 | 0 | 8.5 ± 6.36 | 1.37 | 5.5 ± 0.7 | 0.85 | 5.5 ± 2.12 | 0.89 |
| | positive | 189.5 ± 19.09 | | 189.5 ± 19.09 | | 189.5 ± 19.09 | | 189.5 ± 19.09 | | 189.5 ± 19.09 | |
| TA 1535 | 0 | 3 ± 1.41 | | 3 ± 1.41 | | 3 ± 1.41 | | 3 ± 1.41 | | 3 ± 1.41 | |
| | 200 | 2.5 ± 0.7 | 0.57 | 0 ± 0 | 0 | 1 ± 0 | 0.23 | >150 | >34 | 0 ± 0 | 0 |
| | 100 | 1 ± 0 | 0.23 | 0 ± 0 | 0 | 3 ± 0 | 0.68 | 0 ± 0 | 0 | 1.5 ± 0.7 | 0.34 |
| | 50 | 2.5 ± 2.12 | 0.57 | 1 ± 0 | 0.23 | 0 ± 0 | 0 | 1.5 ± 0.7 | 0.34 | 1 ± 0 | 0.23 |
| | positive | 307.5 ± 10.6 | | 307.5 ± 10.6 | | 307.5 ± 10.6 | | 307.5 ± 10.6 | | 307.5 ± 10.6 | |
| TA 1537 | 0 | 1.5 ± 0.7 | | 1.5 ± 0.7 | | 1.5 ± 0.7 | | 1.5 ± 0.7 | | 1.5 ± 0.7 | |
| | 300 | 0.5 ± 0.7 | 0.23 | 1 ± 0 | 0.45 | 0.5 ± 0.7 | 0.23 | 12.5 ± 4.94 | 5.68 | 0.5 ± 0.7 | 0.23 |
| | 200 | 0 ± 0 | 0 | 1 ± 1.41 | 0.45 | 1 ± 0 | 0.45 | 0.5 ± 0.7 | 0.23 | 0 ± 0 | 0 |
| | 100 | 1 ± 1.41 | 0.45 | 0.5 ± 0.7 | 0.23 | 1.5 ± 2.12 | 0.68 | 1 ± 1.41 | 0.45 | 0.5 ± 0.7 | 0.23 |
| | 50 | 1119 ± 21.21 | | 1119 ± 21.21 | | 1119 ± 21.21 | | 1119 ± 21.21 | | 1119 ± 21.21 | |
| | positive | 4 ± 0 | | 4 ± 0 | | 4 ± 0 | | 4 ± 0 | | 4 ± 0 | |
| E. coli | 0 | 0 ± 0 | 0 | 0 ± 0 | 0 | 2 ± 2.82 | 0.5 | >300 | >75 | 5.5 ± 2.12 | 1.38 |
| | 200 | 1.5 ± 0.7 | 0.38 | 0 ± 0 | 0 | 1.5 ± 0.7 | 0.38 | 7 ± 0 | 1.75 | 1.5 ± 0.7 | 0.38 |
| | 100 | 4.5 ± 3.53 | 1.13 | 0 ± 0 | 0 | 2.5 ± 2.12 | 0.63 | 4 ± 0 | 1 | 3 ± 1.41 | 0.75 |
| | 50 | 13 ± 0 | | 13 ± 0 | | 13 ± 0 | | 13 ± 0 | | 13 ± 0 | |
| | positive | 2.5 ± 0.7 | | 2.5 ± 0.7 | | 2.5 ± 0.7 | | 2.5 ± 0.7 | | 2.5 ± 0.7 | |

*Baseline - mean of the negative control + SD

Example 3: Assessment of Cytotoxicity for Compounds 1-4 and 31

Compounds 1-4 and 31 were tested in a cytotoxicity assay. The assay was based on the conversion of the non-fluorescent dye resazurin to the fluorescent compound rezorufin in the reducing environment of living cell cytoplasm. The more living cells in a sample result in higher fluorescence, while less living cells result in lower fluorescence.

A. Materials and Equipment

Reagents and consumables included: DMSO Chromasolv Plus, HPLC grade, ≥99.7% (Sigma-Aldrich, USA; Cat #34869), DMEM (4.5 g/L) liquid without L-Glutamine (PAA, UK; Cat #E15-009), Dulbecco's PBS (1×) without Ca and Mg (PAA, UK; Cat #H15-002), L-glutamine (200 mM) (PAA, UK; Cat #M11-004), Fetal Bovine Serum "GOLD" EU approved (PAA, UK; Cat #A15-151), penicillin/streptomycin (100×) (PAA, UK; Cat #P11-010), resazurin (SynbiaS, Ukraine; Cat #62758-13-8), doxorubicin, valium for solution for injection (Arterium, Ukraine; pharmaceutical), trypsin EDTA (10×) 0.5%/0.2% in DPBS (PAA, UK; Cat #L11-003), Costar® 96-well cell culture cluster round bottom with polystyrene lid (Corning Incorporated, Cat #3790), disposable pipettor tips (Thermo Scientific, Fisherbrand, Eppendorf USA), centrifuge tubes, 50 mL (Santa Cruz, USA; Cat #sc-200251), Falcon® 96-well plate, black/clear (BD, Cat #358078), and serological pipettes 5 mL, 10 mL, 25 mL (Greiner Bio-One).

Equipment included: a cell culture $CO_2$ incubator, model CCL-170B-8 (ESCO, Singapore), a centrifuge 5804R (Eppendorf, USA), an etched hemacytometer, dark-line counting chamber (Hausser Scientific, USA; Cat #3500), CyBi®-SELMA, semi-automatic 96-fold pipettor (Analytik Jena AG), a Labculture Biological Safety Cabinet, Class II, Type A2 (ESCO), an inverted Microscope, Model CK2 (Olympus Optical Co., Ltd., Japan), a microscope Leica DM LS2 (Leica Microsystems Wetzlar GmbH, Germany), a multi-mode microplate reader POLARstar Omega (BMG Labtech GMBH, Germany), a Titertek Multidrop 384 Model 832 (Thermo Scientific/Titertek, USA), StakMax Microplate Handling System (Molecular Devices), PIPETMAN pipettes 2-20 μL, 50-200 μL, 200-1000 μL (Gilson, USA), and multichannel electronic pipettes 2-125 μL, 5-250 μL, 15-1250 μL, Matrix (Thermo Scientific, USA).

B. Methods

HepG2 cells were cultivated in a humidified atmosphere at 37° C. and 5% $CO_2$ in 75 $cm^2$ flasks to 80-90% of confluence and split twice per week with a subcultivation ratio of 1:4. The cell layer was rinsed with PBS to remove all traces of serum. Then 3.0 mL of solution containing 0.25% (w/v) trypsin and 0.53 mM EDTA was added to the flask and incubated about 10 minutes. The HepG2 cells were detached using a scraper and re-suspended in DMEM containing 10% FBS and 2 mM glutamine. The cell suspension with a final concentration of $5 \times 10^5$ cells/mL was dispensed into sterile 96-well black wall clear flat bottom plates as previously described (McMillian et al. (2002) Cell Biol. Toxicol. 18(3):157-173; Mulvihill et al. (2009) Future Med. Chem. 1(6):1153-1171) and the test compounds were added.

The compound DMSO stock solutions were diluted with PBS to achieve an intermediate concentration of 1 mM. The cell proliferation assessment was performed at different concentrations of compounds ranging from 0.1 μM to 100 μM. Doxorubicin at a final concentration of 20 μM was used as a positive control. After compound addition, cells were incubated for 24 hours in a humidified atmosphere at 37° C. and 5% $CO_2$.

Resazurin was added to the final concentration (50 µM) and incubated for 4 hours under the same conditions. Presence of rezorufin (cell viability) was quantified by measuring fluorescence (Ex—490 nm, Em—540 nm; see Vega-Avila and Pugsley (2011) Proc. West Pharmacol. Soc. 54:10-14).

The percent of cell proliferation inhibition was calculated by applying the following formula:

$$CPI = \left(\frac{AVG_{Highcontrols} - Well_{RFU}}{AVG_{Highcontrols} - AVG_{Lowcontrols}}\right) * 100,$$

CPI—cell proliferation inhibition;
AVG High control—mean of RFU of wells containing cell suspension and PBS;
Well RFU—RFU of target well with test compound; and
AVG Low controls—mean of RFU of wells containing cell suspension and doxorubicin.

$IC_{50}$ values were calculated using GraphPad Prism software.

C. Results

Doxorubicin was used as a reference compound to assess inhibition of cell proliferation. The data of HepG2 cell proliferation inhibition by doxorubicin at 20 µM were used as high control and the value of RFU was taken for 100% of inhibition.

HepG2 cell proliferation inhibition (%) by the Compounds 1-4 and 31 is listed in Table 5 below.

TABLE 5

HepG2 cell proliferation inhibition (%) by the Compounds 1-4 and 31.

| Concentration of compounds, µM | HepG2 proliferation inhibition (%) | | | | |
|---|---|---|---|---|---|
| | 21 | 1 | 2 | 3 | 4 |
| 100 µM | −17.7 | 0.1 | 14.7 | 0.5 | −5.5 |
| 30 µM | −5.4 | −2.5 | 2.4 | −0.1 | −3.8 |
| 10 µM | −2.2 | −3.9 | 2.6 | 2.6 | −1.4 |
| 3 µM | −0.9 | −1.8 | 5.6 | 3.9 | 5.4 |
| 1 µM | −1.5 | −0.6 | 1.2 | 2.4 | 0.8 |
| 0.3 µM | −0.8 | −2.0 | 2.8 | 0.2 | 0.1 |
| 0.1 µM | 2.0 | −0.1 | −1.8 | −2.1 | −1.8 |

Based on the results of the study of proliferation inhibition of HepG2 cells at different concentrations ranging from 100 µM to 0.1 µM, none of the tested compounds exhibited significant cytotoxic effects.

Example 4: In Vitro Predictor hERG Fluorescence Polarization Assay for Compounds 1-4 and 31

A preliminary assessment of human Ether-a-go-go-Related Gene (hERG) binding for Compounds 1-4 and 31 a fluorescence polarization assay was performed. Fluorescence polarization (FP) readout technology is based on the observation that when a small fluorescent molecule (the tracer) is excited by the polarized light, the emitted light is largely depolarized because of the rapid rotation of the molecule in the solution during its fluorescence lifetime. The hERG predictor assay provides valuable information about the possible binding of test compounds to the potassium channel and potential QT prolongation on echocardiogram.

A. Materials and Equipment

Reagents and consumables used included DMSO Chromasolv Plus, HPLC grade, ≥99.7% (Sigma-Aldrich, USA; Lot #34869), Predictor™ hERG Fluorescence Polarization Assay kit (Invitrogen; Cat #PV5365), Corning assay plate, 384 wells, U-bottom, black polystyrene (Corning, USA; Cat. #3677), and Compounds 1-4 and 31.

Equipment included a TECAN ULTRA Multifunctional Plate Reader (Tecan, Austria), micropipettes 0.5-5 µL, 2-20 µL, 15-200 µL, 100-1000 µL (Finntip, Eppendorf, Gilson), a multichannel pipette (30 µL) (Thermo Matrix, USA), and a water purification system, NANOpure Diamond D11911 (Thermo Scientific Barnstead, USA).

B. Methods

All experiments were performed using the Predictor™ hERG Fluorescence Polarization Assay in accordance with the manufacturer's protocol PV5365 (Invitrogen, Carlsbad, Calif.).

The hERG reaction was performed by incubating the tracer and membranes with hERG channel for 2-4 hours in the solution. The fluorescence polarization was maximal when nothing interfered with the reaction of the tracer and hERG membranes (minimal tracer rotation). But when a tested compound competed with the tracer for the hERG channel, the polarization of emitted light lowered due to the ability of free unbound tracer to rotate rapidly in the solution. The reference compound (E-4031, provided by the manufacturer) was used to validate assay performance. The calibration curve of the E-4031 was used to compare the $IC_{50}$ of E-4031 in the performed assay with the manufacturer's provided data. "Sigmoidal dose-response (variable slope)" function of GraphPad Prism software was used for the calibration curve building and calculation of $IC_{50}$ for E-4031 assessment. The $IC_{50}$ value for E-4031 was found to be approximately 70 nM in accordance with the published data.

All test points for the compounds were performed in quadruplicates. Three dilutions of the tested compounds were assessed—1 µM, 5 µM and 20 µM.

A set of positive and negative controls (Assay blank—no tracer added, Assay Negative—30 µM of E-4031 that represented 100% tracer displacement and gave minimum assay polarization value) was performed with 4 repeats.

C. Results

Figure 18:
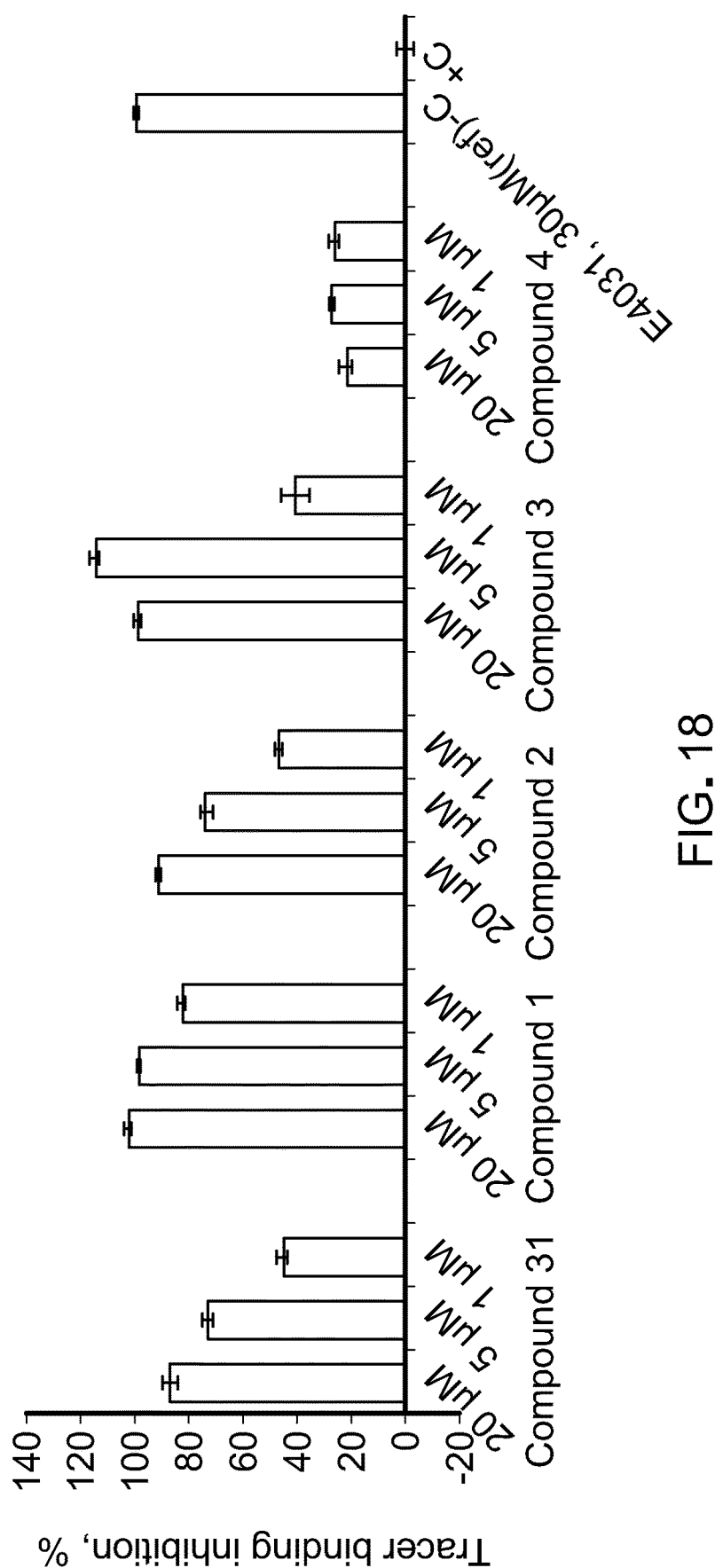
FIG. 18 is a bar graph showing tracer binding inhibition from in vitro hERG fluorescence polarization assay for compounds 1-4 and 31.
Figure 19A:
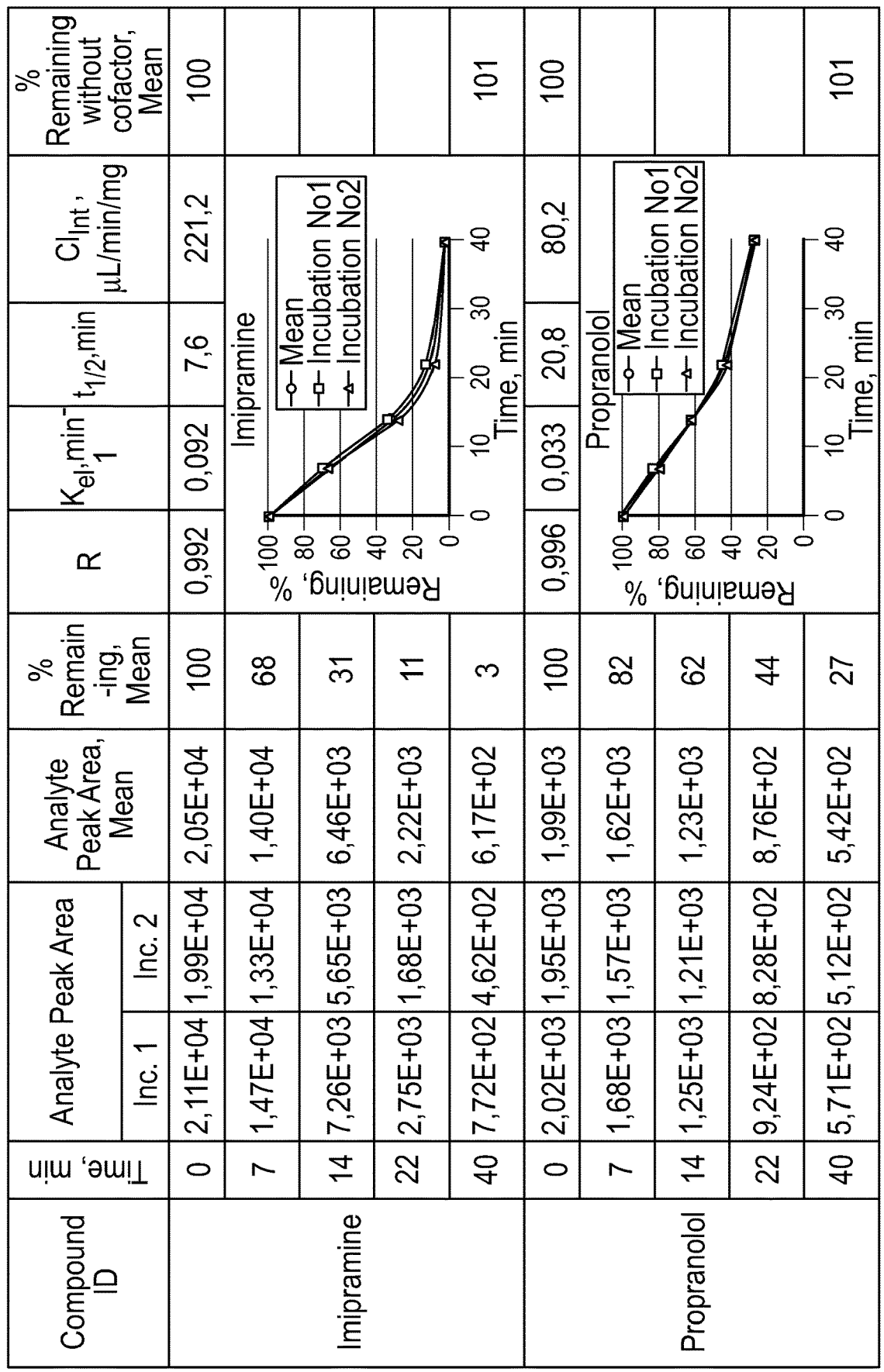
Figure 19C:
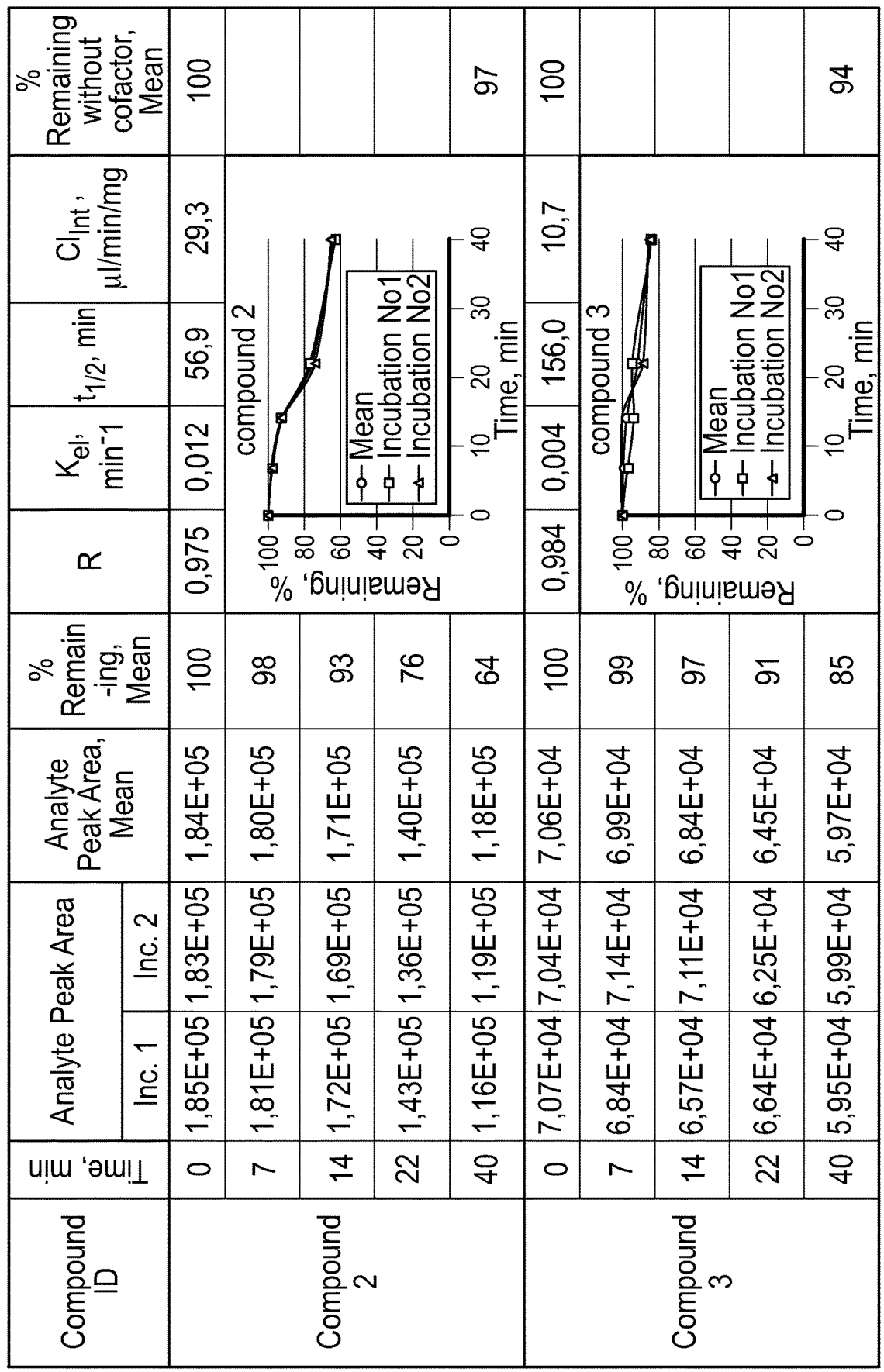
Figure 19D:
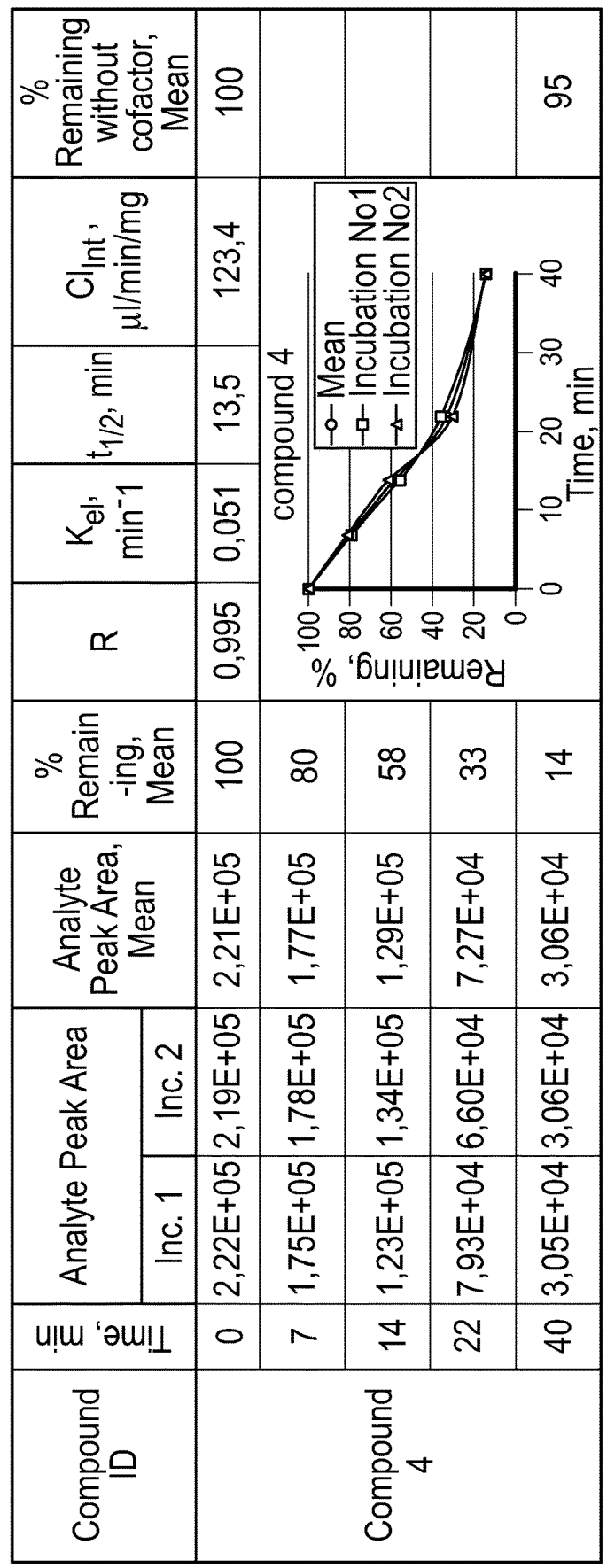
Figure 20A:
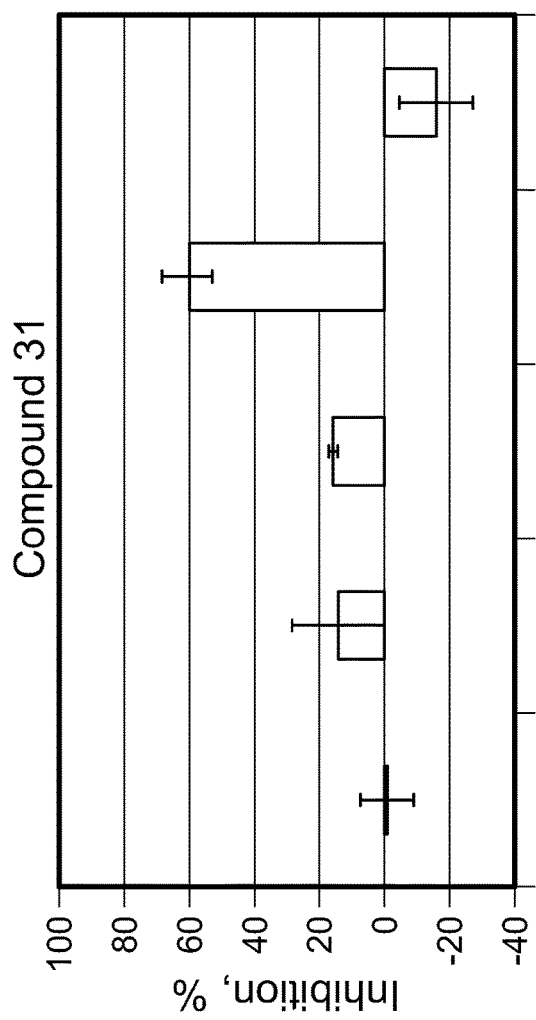
FIGS. 20A-20E are the CYP inhibition profiles for compounds 1-4 and 31.
Figure 20B:
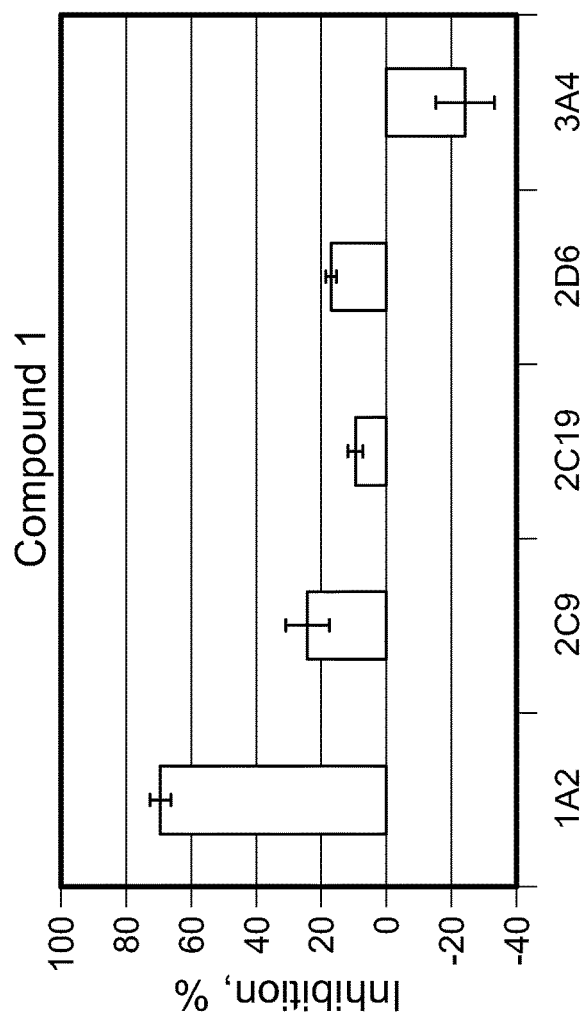
Figure 20C:
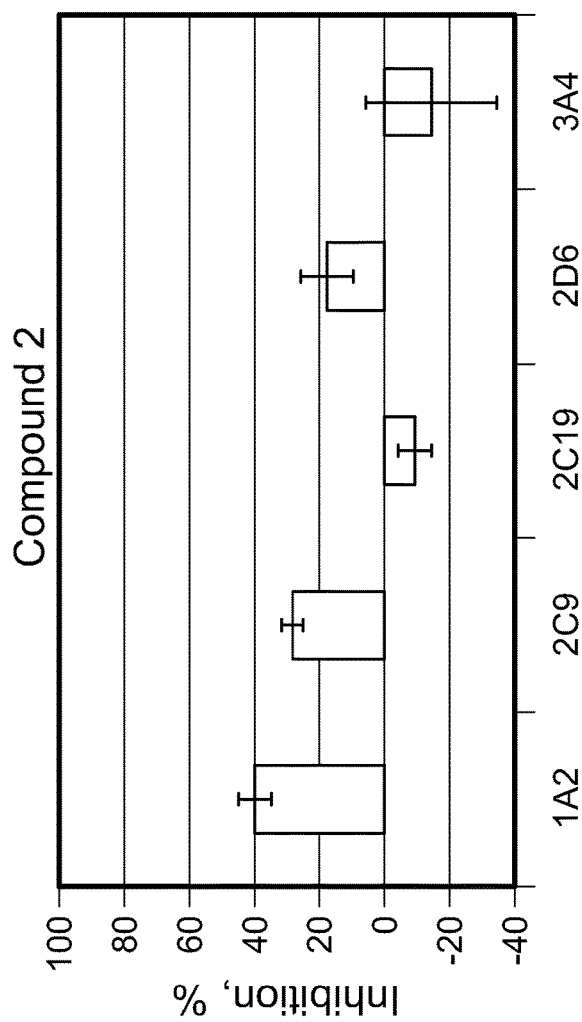
Figure 20D:
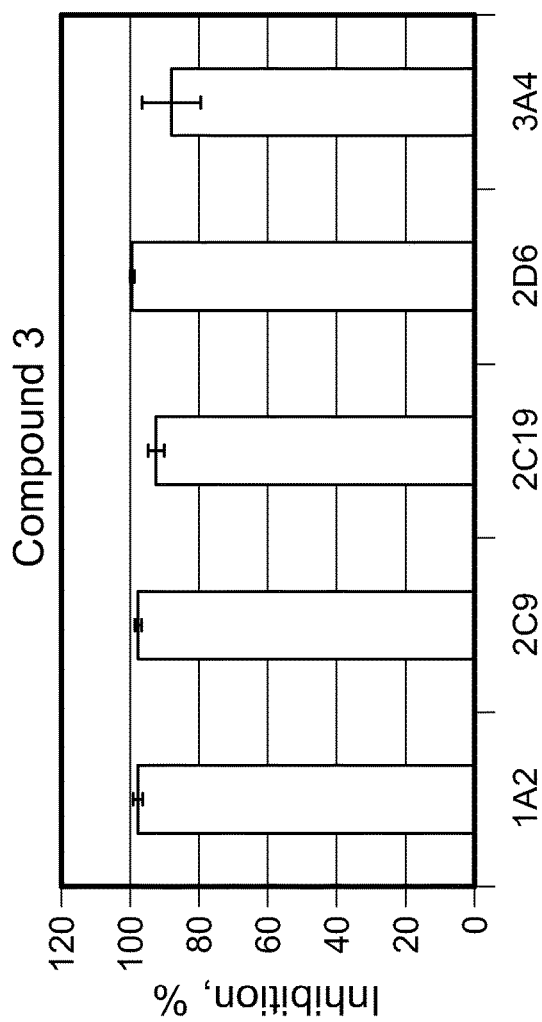
Figure 20E:
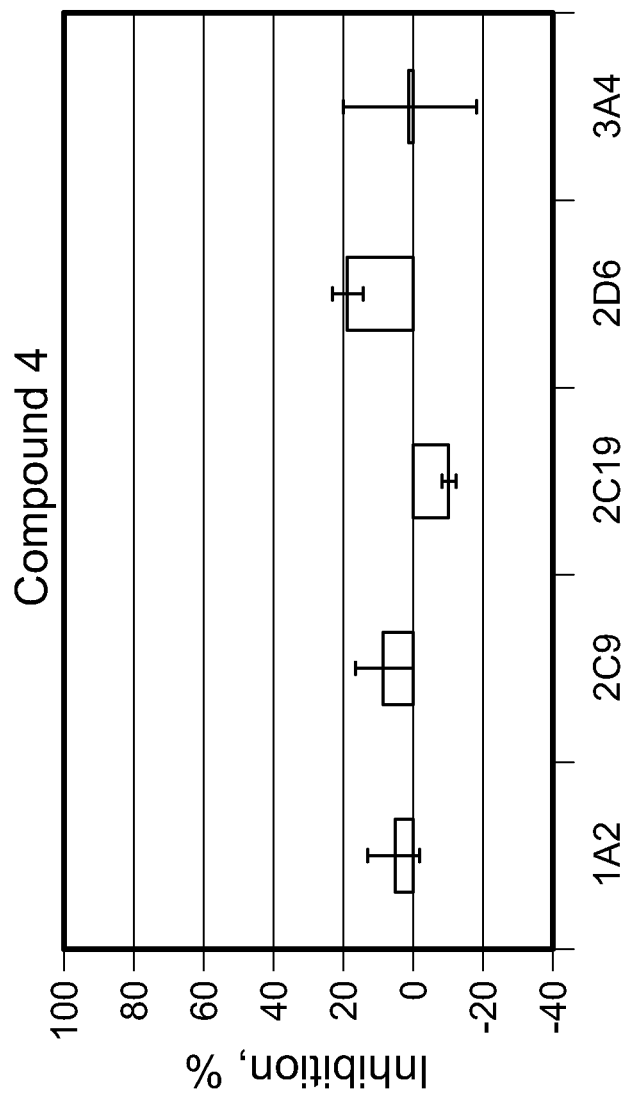

Compounds 1, 2, 3 and 31 showed significant and dose dependent inhibition of the tracer binding, suggesting possible presence of hERG liability. Compound 4 showed low inhibition of the tracer binding without dose dependence. See Table 6 below and FIG. 18.

TABLE 6 hERG binding profile for Compounds 1-4 and 21

| | Binding values, % | | | | Mean | SE |
|---|---|---|---|---|---|---|
| Compound 31, 20 µM | 92.6 | 80.0 | 87.8 | 90.2 | 88 | 2.7 |
| Compound 31, 5 µM | 73.4 | 78.2 | 68.6 | 73.4 | 73 | 2.0 |
| Compound 31, 1 µM | 47.6 | 48.8 | 41.0 | 44.6 | 45 | 1.7 |
| Compound 1, 20 µM | 105.3 | 102.3 | 99.2 | 105.3 | 103 | 1.4 |
| Compound 1, 5 µM | 99.2 | 98.0 | 100.5 | 99.2 | 99 | 0.5 |
| Compound 1, 1 µM | 81.2 | 87.2 | 79.4 | 83.6 | 83 | 1.7 |
| Compound 2, 20 µM | 92.6 | 92.0 | 90.8 | 90.2 | 91 | 0.5 |
| Compound 2, 5 µM | 69.8 | 80.6 | 69.8 | 75.8 | 74 | 2.6 |
| Compound 2, 1 µM | 44.0 | 49.4 | 45.2 | 49.4 | 47 | 1.4 |
| Compound 3, 20 µM | 98.6 | 98.6 | 102.3 | 97.4 | 99 | 1.0 |
| Compound 3, 5 µM | 111.9 | 117.3 | 113.7 | 118.5 | 115 | 1.5 |
| com Compound | 42.2 | 49.4 | 26.6 | 45.8 | 41 | 5.0 |
| Compound 4, 20 µM | 17.0 | 25.4 | 27.2 | 18.8 | 22 | 2.5 |

TABLE 6-continued hERG binding profile for Compounds 1-4 and 21

|  | Binding values, % | | | | Mean | SE |
|---|---|---|---|---|---|---|
| Compound 4, 5 µM | 25.4 | 27.8 | 27.2 | 29.0 | 27 | 0.8 |
| Compound 4, 1 µM | 22.4 | 32.0 | 24.2 | 27.2 | 26 | 2.1 |
| E4031, 30 µM(ref) −C | 99.8 | 101.1 | 98.6 | 100.5 | 100 | 0.5 |
| +C | −5.9 | 3.8 | −5.3 | 7.4 | 0 | 3.3 |

Example 5: Assessment of Caco-2 A-B Permeability for Compounds 1-4 and 31

A Caco-2 permeability assay was performed to determine the suitability of Compounds 1-4 and 31 for oral dosing by predicting the in vivo absorption of drugs in the intestine by measuring the rate of transport of the compound across the Caco-2 cell line.

A. Materials and Equipment

Reagents and consumables used included: Trypsin EDTA (10×) 0.5%/0.2% in DPBS (PAA, UK; Cat #L11-003), HEPES, High Purity Grade (Helicon, Am-0485), Dulbecco's PBS (1×) without Ca and Mg (PAA, UK; Cat #H15-002), Hanks' BSS (1×) without Ca and Mg and without phenol red (PAA, UK; Cat #H15-009), DMSO Chromasolv Plus, HPLC grade, ≥99.7% (Sigma-Aldrich, USA; Cat #34869), DMEM (4.5 g/L) liquid without L-glutamine (PAA, UK; Cat #E15-009), L-glutamine (200 mM) (PAA, UK; Cat #M11-004), Fetal Bovine Serum "GOLD" EU approved (PAA, UK; Cat #A15-151), penicillin/streptomycin (100×) (PAA, UK; Cat #P11-010), acetonitrile Chromasolv, gradient grade, for HPLC, ≥99.9% (Sigma-Aldrich, USA; Cat #34851), formic acid for mass spectrometry, ~98% (Fluka, USA; Cat #94318), Falcon® HTS 24-multi-well insert systems with media feeder tray (BD Biosciences, USA; Prod #351181), Falcon® 24-well TC-treated cell PS permeable support companion plate (BD, Prod #353504), centrifuge tubes, 50 mL (Santa Cruz, USA; Cat #sc-200251), serological pipettes 5 mL, 10 mL, 25 mL (Greiner Bio-One), disposable pipettor tips (Thermo Scientific, Fisherbrand, Eppendorf USA), 1.1 mL microtubes in microracks (Thermo Scientific, USA), Zorbax Eclipse Plus C18 column 2.1×50 mm, 3.5 m (Agilent Technologies, Inc. USA), propranolol hydrochloride ≥99% (TLC), powder (Sigma-Aldrich, USA; Cat #P0884), imipramine hydrochloride ≥99% (TLC) (Sigma-Aldrich, USA; Lot #17379), and atenolol, analytical reference material, ≥98.5% (HPLC) (Sigma-Aldrich, USA; Cat #74827).

Equipment included: a cell culture $CO_2$ incubator, model CCL-170B-8 (ESCO, Singapore), a centrifuge 5804R (Eppendorf, USA), a centrifuge 4-15C (Qiagen) (Sigma, Germany), an etched hemacytometer, dark-line counting chamber (Hausser Scientific, USA; Cat #3500), a gradient HPLC system VP (Shimadzu, Japan), an Innova 4080 Incubator Shaker (New Brunswick Scientific, USA), a Millicell-ERS system ohm meter (Millipore, Cat #MERS 000 01), an MS/MS detector API 3000 PE with TurbolonSpray Electrospray module (PE Sciex, USA), a multichannel manual pipette (Thermo Labsystems Finnpipette, FA16-50R), multichannel electronic pipettes 2-125 µL, 5-250 µL, 15-1250 µL, Matrix (Thermo Scientific, USA), PIPETMAN pipettes 2-20 µL, 50-200 µL, 200-1000 µL (Gilson, USA), VWR membrane nitrogen generators N2-04-L1466, nitrogen purity 99%+(VWR, USA), and a water purification system NANOpure Diamond D11911 (Thermo Scientific Barnstead, USA).

All measurements were performed using a Shimadzu VP HPLC system that included a vacuum degasser, gradient pumps, reverse phase HPLC column, column oven and autosampler. The HPLC system was coupled with a tandem mass spectrometer API 3000 (PE Sciex). The TurbolonSpray ion source was used in both positive and negative ion modes. Acquisition and analysis of the data were performed using Analyst 1.5.2 software (PE Sciex).

The LC-MS conditions were as follows. Column: Agilent ZORBAX Eclipse Plus C18; Mobile phase A: Acetonitrile:Water:Formic acid=100:1000:1; Mobile phase B: Acetonitrile:Formic acid=1000:1; Gradient: 0 min 25% B, 1.1 min 100% B, 1.5 min 100% B, 1.51 min 25% B, 2.7 min stop; Elution rate: 400 µL/min; Column temperature: 30° C.; Injection volume: 2 µL; Ion source: Turbo spray; Ionization model: ESI; Scan type: Positive Q3 Multiple Ions; Nebulize gas: 15 L/min, Curtain gas: 8 L/min; Ionspray voltage: 5000 V, Temperature: 400° C.

B. Methods

Caco-2 cells were cultivated in 75 $cm^2$ flasks to 80-90% of confluence according to the ATCC and Millipore recommendations (Millipore protocol note PC1060EN00P) in a humidified atmosphere at 37° C. and 5% $CO_2$. Cells were detached with Trypsin/EDTA solution and re-suspended in the cell culture medium to a final concentration of $2\times10^5$ cells/mL. 500 µL of the cell suspension was added to each well of an HTS 24-multiwell insert system and 35 mL of prewarmed complete medium was added to the feeder tray. Caco-2 cells were incubated in the multiwell insert system for 10 days before the transport experiments. The medium in the filter plate and feeder tray was changed every other day. After 10 days of cell growth, the integrity of the monolayer was verified by measuring the transepithelial electrical resistance (TEER) for every well using the Millicell-ERS system ohm meter. The TEER values obtained were greater than 1000Ω (between 1400 and 1500Ω) as required by the assay conditions. The 24-well insert plate was removed from its feeder plate and placed in a new sterile 24-well transport analysis plate. The medium was aspirated and inserts washed with PBS.

To determine the rate of drug transport in apical (A) to basolateral (B) direction, 300 µL of the test compound solution in buffer (HBSS, 5.6 mM glucose, 10 mM HEPES, pH=7.4) was added into the filter wells and 1000 µL of the same buffer was added to wells in the transport analysis plate. The plates were incubated for 90 min. at 37° C. with shaking at 50 rpm. 75 µL aliquots were taken from the apical and basolateral compartment for LC-MS/MS analysis. All samples for LC-MS/MS analysis were extracted by acetonitrile (×2 volume) followed by protein sedimentation by centrifuging at 10000 rpm for 10 minutes. Supernatants were analyzed using the HPLC system coupled with a tandem mass spectrometer.

Imipramine, propranolol (high permeability), and atenolol (low permeability) were used as reference compounds.

The apparent permeability (Papp) was calculated for the Caco-2 permeability assay using the following equation:

$$P_{app}=(V_A/((Area)\times(Time))\times([drug]_{acc}/[drug]_{initial,d}),$$
where:

VA—volume of transport buffer in acceptor well;
Area—surface area of the insert (equals to effective growth area of the insert—0.31 sq.cm);
Time—time of the assay;
$[drug]_{acc}$—concentration of test compound in acceptor well;

[drug]$_{initial,d}$—initial concentration of test compound in a donor well; and Papp is expressed in $10^{-6}$ cm/sec.

C. Results

The A-B permeability data for Compounds 1-4 and 31 reference compounds imipramine, propranolol, and atenolol is listed in Table 7 below. The A-B permeability values for the reference compounds correspond to the literature data (see, e.g., Lau et al. (2004) Drug Metab. Dispos. 32:937-942; Fujikawa et al. (2005) Bioorg. Med. Chem. 13(15): 4721-4732; Rubas et al. (1996) J. Pharm. Sci. 85(2):165-169). The permeability of all test compounds can be classified as medium to high permeability.

TABLE 7

A-B permeability data of Compounds 1-4 and 31

| Compound ID | Permeability ($10^{-6}$ cm/s) | | | |
|---|---|---|---|---|
| | 1 | 2 | Mean | SD |
| Imipramine | 21.1 | 17.8 | 19.5 | 2.4 |
| Propranolol | 23.0 | 20.6 | 21.8 | 1.7 |
| Atenolol | 0.5 | 0.4 | 0.5 | 0.1 |
| 31 | 52.8 | 45.2 | 49.0 | 5.4 |
| 1 | 8.3 | 12.1 | 10.2 | 2.7 |
| 2 | 17.9 | 18.5 | 18.2 | 0.4 |
| 3 | 39.5 | 41.7 | 40.6 | 1.6 |
| 4 | 15.9 | 14.6 | 15.3 | 0.9 |

Example 6: Assessment of Metabolic Stability in Mouse Liver Microsomes for Compounds 1-4 and 31

The metabolic stability of Compounds 1-4 and 31 and two reference compounds (imipramine and propranolol) in liver microsomes was determined at five time points over 40 minutes using HPLC-MS. Metabolic stability was defined as the percentage of parent compound lost over time in the presence of a metabolically active test system, such as rodent liver microsomal fractions.

A. Materials and Equipment

Reagents and consumable used included: DMSO Chromasolv Plus, HPLC grade, ≥99.7% (Sigma-Aldrich, USA; Cat #34869), acetonitrile Chromasolv, gradient grade, for HPLC, ≥99.9% (Sigma-Aldrich, USA; Cat #34851), potassium phosphate monobasic ACS Grade (Helicon, Cat #Am-0781), potassium phosphate dibasic ACS Grade (Helicon, Cat #Am-0705), magnesium chloride hexahydrate (Helicon, Cat #Am-0288), microsomes from liver, pooled, male BALB/c mice, glucose-6-phosphate dehydrogenase from baker's yeast (S. cerevisiae), type XV (Sigma-Aldrich, USA; Cat #G6378), glucose-6-phosphate sodium salt, Sigma Grade, crystalline (Sigma-Aldrich, USA; Cat #G7879), NADPH tetrasodium salt, ≥95% (Santa Cruz Biotechnology, Inc., USA; Cat #sc-202725), formic acid for mass spectrometry, ~98% (Fluka, USA; Cat #94318), DMSO stock solutions of the test compounds at 10 mM, propranolol hydrochloride ≥99% (TLC), powder (Sigma-Aldrich, USA; Cat #P0884), imipramine hydrochloride ≥99% (TLC) (Sigma-Aldrich, USA; Lot #17379), Zorbax Eclipse Plus C18 column 2.1×50 mm, 3.5 m (Agilent Technologies, Inc. USA), and 1.1 mL microtubes in microracks, pipettor tips (Thermo Scientific, USA).

Equipment included: a gradient HPLC system VP (Shimadzu, Japan), an MS/MS detector API 3000 PE with TurbolonSpray Electrospray module (PE Sciex, USA), VWR membrane nitrogen generators N2-04-L1466, nitrogen purity 99%+(VWR, USA), Innova 4080 Incubator Shaker (New Brunswick Scientific, USA), a water purification system NANOpure Diamond D11911 (Thermo Scientific Barnstead, USA), a centrifuge 4-15C (Qiagen) (Sigma, Germany), and multichannel electronic pipettes 2-125 μL, 5-250 μL, 15-1250 μL, Matrix (Thermo Scientific, USA; Cat ##2001, 2002, 2004).

All measurements were performed using a Shimadzu VP HPLC system including vacuum degasser, gradient pumps, reverse phase HPLC column, column oven and autosampler. The HPLC system was coupled with a tandem mass spectrometer API 3000 (PE Sciex). The TurbolonSpray ion source was used in both positive and negative ion modes. Acquisition and analysis of the data were performed using Analyst 1.5.2 software (PE Sciex).

B. Methods

Mouse hepatic microsomes were isolated from pooled (50), perfused livers of BALB/c male mice according to the standard protocol (Hill, J. R. in Current Protocols in Pharmacology 7.8.1-7.8.11, Wiley Interscience, 2003). The batch of microsomes was tested for quality control using imipramine, propranolol and verapamil as reference compounds. Microsomal incubations were carried out in 96-well plates in 5 aliquots of 40 μL each (one for each time point). Liver microsomal incubation medium contained PBS (100 mM, pH 7.4), MgCl$_2$ (3.3 mM), NADPH (3 mM), glucose-6-phosphate (5.3 mM), glucose-6-phosphate dehydrogenase (0.67 units/mL) with 0.42 mg of liver microsomal protein per mL. Control incubations were performed replacing the NADPH-cofactor system with PBS. Compounds 1-4 and 31 (2 μM, final solvent concentration 1.6%) were each incubated with microsomes at 37° C. while shaking at rpm. Incubations were performed in duplicates. Five time points over 40 minutes were analyzed. The reactions were stopped by adding 12 volumes of 90% acetonitrile-water to incubation aliquots, followed by protein sedimentation by centrifuging at 5500 rpm for 3 minutes. Supernatants were analyzed using the HPLC system coupled with tandem mass spectrometer. The elimination constant ($k_{el}$), half-life ($t_{1/2}$) and intrinsic clearance ($Cl_{int}$) were determined in a plot of ln(AUC) versus time, using linear regression analysis:

$$k_{el} = -\text{slope} \quad t_{1/2} = \frac{0.693}{k}$$

$$Cl_{int} = \frac{0.693}{t_{1/2}} \times \frac{\mu l_{incubation}}{mg_{microsomes}}.$$

In order to indicate the quality of the linear regression analysis, the R (correlation coefficient) values were provided. In some cases, the last time point was excluded from the calculations to ensure acceptable logarithmic linearity of decay.

C. Results

Mouse microsomal stability data for two reference compounds (imipramine and propranolol) and Compounds 1-4 and 31 are shown in FIGS. 19A-19D. Compounds 4 and 31 showed low stability, Compounds 1 and 2 exhibited moderate stability and Compound 3 showed high metabolic stability in the mouse hepatic microsomal test system. "No cofactor" control data indicated that the observed instability was primarily determined by CYP450 activity.

Example 7: In Vitro CYP450 Inhibition for Compounds 1-4 and 31

A preliminary assessment of inhibition of the major CYP450 panel (1A2, 2C9, 2C19, 2D6, 3A4) by Compounds 1-4 and 31 at a single compound concentration (10 μM) was made. CYP450 inhibition profiling provides valuable information regarding any possible drug-drug interactions for a test compound.

A. Materials and Equipment

Reagents and consumable used included: DMSO Chromasolv Plus, HPLC grade, ≥99.7% (Sigma-Aldrich, USA; Cat #34869); acetonitrile Chromasolv, gradient grade, for HPLC, ≥99.9% (Sigma-Aldrich, USA; Cat #34851); P450-Glo™ Screening Systems (Promega Corp.) that included CYP 1A2 (Cat. #V9770), CYP 2C9 (Cat. #V9790), CYP 2C19 (Cat. #V9880), CYP 2D6 (Cat. #V9890), CYP 3A4 (Cat. #V9800), and Luciferin-PPXE (Cat. #V9910); Corning assay plate 384 wells (Corning, USA; Cat. #3673); and Matrix 96-well assay plates (Matrix, Thermo Scientific, USA; Cat. #4919).

Equipment included: a multi-mode microplate reader POLARstar Omega (BMG Labtech GMBH, Germany); a dry thermostat CT50 (Ukrorgsynthez, Ukraine; CT 50); micropipettes 0.5-5 μL, 2-20 μL, 15-200, 100-1000 μL (Finntip, Eppendorf, Gilson); and multichannel electronic pipette 1.0-30 μL, Matrix (Thermo Scientific, USA; Cat #2060).

B. Methods

All experiments were performed using P450-Glo™ Assay Systems (Promega) in accordance with the manufacturer's protocols. The P450-Glo™ Assays provide a luminescent readout-based method for measuring cytochrome P450 activity. A conventional cytochrome P450 reaction was performed by incubating the cytochrome P450 and a luminogenic cytochrome P450 substrate. The substrates in the P450-Glo™ assays are derivatives of beetle luciferin. The derivatives themselves are not substrates for luciferase but are converted by cytochrome P450s to luciferin, which in turn reacts with luciferase to produce light. The amount of light produced was directly proportional to cytochrome P450 activity. All test points were performed in quadruplicates. Control membranes (without CYPs) represented the Negative control (baseline). DMSO final concentration was 0.25%.

The following reference compounds were used to assess CYP inhibition:

| CYP | Reference inhibitor | Ref. inhibitor conc., uM | CYP inhibition, % |
|---|---|---|---|
| 1A2 | alfa-naphthoflavone | 4 | 99.64 |
| 2C9 | fluconazole | 120 | 84.46 |
| 2C19 | omeprazole | 24 | 84.06 |
| 2D6 | quinidine | 1 | 88.42 |
| 3A4 | ketoconazole | 20 | 102.76 |

Concentrations of alfa-naphthoflavone, quinidine, ketoconazole, fluconazole and omeprazole are shown as 4× of Promega protocol recommendations or 4× of their $IC_{50}$ found in the literature (see, e.g., Li et al. (2004) Drug Metab. Dispos. 32(8):821-827; Niwa et al. (2005) Biol. Pharm. Bull. 28(9):1805-1808).

C. Results

The CYP inhibition profiles for Compounds 1-4 and 31 are shown below and in FIGS. 20A-20E. At the concentration of 10 μM, Compound 3 showed very high inhibition of all 5 tested CYP450. CYP 1A2 was significantly inhibited by Compounds 1 and 2. CYP 2D6 was significantly inhibited by Compound 31. Compound 4 did not show a significant inhibition of any CYP450 isoform.

1. CYP Inhibition Profile for Compound 31

| CYP | Inhibition, % | | | | Mean | SE |
|---|---|---|---|---|---|---|
| 1A2 | 16.7 | -0.7 | 3.6 | -22.5 | -0.7 | 8.1 |
| 2C9 | 50.4 | -18.3 | 11.9 | 13.7 | 14.5 | 14.1 |
| 2C19 | 14.0 | 18.2 | 14.4 | 18.2 | 16.2 | 1.2 |
| 2D6 | 41.0 | 75.7 | 66.5 | 59.0 | 60.6 | 7.4 |
| 3A4 | | -17.9 | 4.1 | -34.5 | -16.1 | 11.2 |

2. CYP Inhibition Profile for Compound 1

| CYP | Inhibition, % | | | | Mean | SE |
|---|---|---|---|---|---|---|
| 1A2 | 73.2 | 60.1 | 69.6 | 73.2 | 69.0 | 3.1 |
| 2C9 | 40.6 | 11.1 | 15.7 | 28.5 | 24.0 | 6.6 |
| 2C19 | 5.0 | 7.4 | 11.6 | 13.5 | 9.4 | 1.9 |
| 2D6 | | 18.5 | 13.7 | 18.8 | 17.0 | 1.6 |
| 3A4 | -6.9 | -37.2 | -29.0 | | -24.4 | 9.1 |

3. CYP Inhibition Profile for Compound 2

| CYP | Inhibition, % | | | | Mean | SE |
|---|---|---|---|---|---|---|
| 1A2 | 49.3 | 30.4 | 47.1 | 34.8 | 40.4 | 4.6 |
| 2C9 | 36.6 | 30.3 | 25.4 | 21.4 | 28.4 | 3.3 |
| 2C19 | -25.0 | -8.6 | 0.8 | -5.3 | -9.5 | 5.5 |
| 2D6 | | 25.3 | 0.5 | 26.0 | 17.3 | 8.4 |
| 3A4 | -53.8 | 12.4 | -1.4 | | -14.3 | 20.2 |

4. CYP Inhibition Profile for Compound 3

| CYP | Inhibition, % | | | | Mean | SE |
|---|---|---|---|---|---|---|
| 1A2 | 98.6 | 96.4 | 95.7 | 100.0 | 97.6 | 1.0 |
| 2C9 | 96.2 | 98.8 | 98.0 | 97.4 | 97.6 | 0.5 |
| 2C19 | 97.4 | 89.9 | 94.6 | 88.0 | 92.5 | 2.1 |
| 2D6 | 98.9 | 100.3 | 99.6 | 99.9 | 99.7 | 0.3 |
| 3A4 | 64.8 | 86.9 | 103.4 | 97.9 | 88.3 | 8.5 |

5. CYP Inhibition Profile for Compound 4

| CYP | Inhibition, % | | | | Mean | SE |
|---|---|---|---|---|---|---|
| 1A2 | 12.3 | 9.4 | 15.9 | -15.2 | 5.6 | 7.1 |
| 2C9 | 27.3 | 11.9 | 4.6 | -11.1 | 8.2 | 8.0 |
| 2C19 | -11.4 | -11.8 | -4.3 | -13.7 | -10.3 | 2.1 |
| 2D6 | | 24.3 | 20.2 | 10.7 | 18.4 | 4.0 |
| 3A4 | -4.1 | 37.2 | -29.0 | | 1.4 | 19.3 |

Experimental Methods for Examples 8-11 Below are as Follows.

Cell Culture and Treatments

All cells were maintained at 37° C. under humidified conditions. CCCP (Sigma-Aldrich) was added to the culture media as a 2× stock concentration. Test compounds 1, 2, 3, 4, and 31 were synthesized by Enamine and dissolved in DMSO (Sigma-Aldrich) at a stock concentration of 10 mM. Aliquots were stored at −80° C. HeLa cells (ATCC) and HeLa cells stably expressing untagged Parkin, EGFP-Parkin, 3×FLAG-Parkin C431S or EGFP-Parkin and mitoKeima were cultured in DMEM (Invitrogen) containing 10% FBS (BioWest). Rat adrenal pheochromocytoma cells (PC12) cells were grown in RPMI with 5% FBS and 10% horse serum. For differentiation, cells were washed in PBS and plated on collagen coated plates in low serum media containing 1% horse serum. Cells were differentiated for 14 days by addition of 100 ng/mL nerve growth factor (NGF).

Primary fibroblasts (Cell Applications) were cultured in fibroblast growth medium (FGM): DMEM containing 10% FBS, 1% penicillin-streptomycin and 1% non-essential amino acids. Direct conversion to neurons was performed utilizing short hairpin RNA targeting polypyrimidine-tract-binding protein (shPTB), which affects proneuronal microRNA circuits (Xue et al., Cell (2013) 152:82-96. Cells were seeded with 40,000 cells/mL and allowed to adhere overnight. 48 h after transduction with pLKO. 1_shPTB lentivirus, positive cells were selected with 2 µg/mL puromycin in fibroblast growth medium. On day 6 media was changed to FGM containing 10 ng/mL fibroblast growth factor (FGF, Genscript). On day 8, media was changed to differentiation media (DMEM:F12 (Invitrogen), 25 µg/mL insulin, 50 µg/mL transferrin, 0.1 µM putrescine 0.03 µM Na-selenite (all Sigma-Aldrich), and 15 ng/mL FGF) containing 5% FBS. On days 10 and 12 media was replaced with differentiation media containing reduced serum (2% FBS). On day 14, media was changed to differentiation media containing 2% FBS and 0.01 µg/mL BDNF, GDNF, CNTF and NT3 (all peprotech) and 2% of anti-oxidant free B27 (Invitrogen) for 48 h. Experiments were performed on day 16 in differentiation media containing growth factors and B27.

Sandwich ELISA Assays

For ELISA assays, 96-well standard bind plates (Mesoscale Discovery) were coated with antibodies (FLAG, Sigma, F3165 or pSer65-Ub, both 1:250) in bicarbonate buffer (15 mM $Na_2CO_3$, 35 mM $NaHCO_3$, pH 9.4) overnight and blocked with 5% BSA in TBS containing 0.02% Tween-20 (TBST). For Parkin Ub-charging, cell lysates were prepared in RIPA buffer (50 mM Tris pH 8.0, 150 mM NaCl, 1% NP-40, 0.5% deoxycholate, 0.1% sodium dodecyl sulphate (SDS)). 25 µg of lysates were added to the plates and incubated for 2 h. To quantify pSer65-Ub, cell lysates were prepared in NP-40 buffer (50 mM Tris pH 7.6, 150 mM NaCl, and 0.5% NP-40) and diluted to 0.18% NP-40 with 1% BSA in TBST. 6.25 µg of lysates were added to the plates overnight and incubated at 4° C. After primary antibody incubation, plates were washed and incubated with mouse detection antibodies (Ub, CST, #3933 or Ub, Millipore, MAB 150 both 1:250) for 1 h at RT. Secondary sulfo-tag conjugated antibodies were incubated for 1 h in 1% BSA/TBST before plates were measured in 2× READ buffer using a Mesoscale Discovery Sector Imager 2400 (both Mesoscale Discovery).

Immunofluorescence

Cells were grown on poly-D-lysine coated glass coverslips. After treatments, cells were fixed in 4% paraformaldehyde and permeabilized using 1% Triton X-100, for each 10 min. Cells were blocked in 10% goat serum. Primary and secondary antibodies were diluted in 1% BSA/PBS and each incubated for 1 h at RT. Primary antibodies used: DNA (mouse, 1:250, Progen, AC-30-10), NBR1 (mouse, 1:100, Abnova H00004077-M01), NDP52 (rabbit, 1:400, Proteintech, 12229-1-AP), OPTN (mouse, 1:200, Santa Cruz, sc-166576), p62 (mouse, 1:400, BD Biosciences, 610832), pSer65-Ub (rabbit, 1:500, in-house (Fiesel et al., EMBO Reports (2015) 16:1114-30; Fiesel et al., (2015) Autophagy 11:2125-2126)), TAX1BP1 (rabbit, 1:200, Cell Signaling, #5105), TOM20 (mouse, 1:100, Santa Cruz, sc-17764), TOM20 (rabbit, 1:2000, Proteintech, 11802-1-AP). Secondary antibodies conjugated to AlexaFluor-568 or-647 (Invitrogen) were diluted 1:1000. Hoechst 33342 (Invitrogen) was diluted 1:5000 to counterstain the nuclei.

Western Blot

Cells were harvested in RIPA buffer or NP-40 lysis buffer containing protease and phosphatase inhibitors (Complete and PhosStop, Roche Applied Science) with the exception of Parkin Ub charging experiments where preheated (95° C.) SDS lysis buffer (50 mM Tris pH 7.6, 150 mM NaCl, 1% SDS) was used. Concentration of cell lysates were determined with bicinchoninic acid (Pierce Biotechnology). For Parkin Ub charging experiments, aliquots of lysates were treated with 0.1 µM NaOH for 1 h at 37° C. pH was neutralized with equinormal HCl.

Protein was subjected to SDS-PAGE using 4-20% or 8-16% Tris-Glycine gels (Invitrogen) and transferred onto polyvinylidene fluoride (PVDF) (Millipore). Membranes were incubated with primary antibodies overnight at 4° C. followed by HRP-conjugated secondary antibodies (1:10, 000; Jackson ImmunoResearch Laboratories). Primary antibodies used: beta III tubulin (rabbit, 1:1000, CST, #5568, CST), FLAG (mouse, 1:250,000, Sigma, F3165), GAPDH (mouse, 1:100,000-500,000, Meridian Life science, H86504M), GST (1:10,000, Sigma, G7781), MFN1 (mouse, 1:5,000, Abcam, ab57602), MFN2 (mouse, 1:5,000, Abcam, ab56889), Parkin (mouse, 1:2,000, Cell Signaling, #4211), pSer65-Ub (rabbit, 1:15,000, in-house (Fiesel et al., EMBO Reports (2015) 16:1114-30; Fiesel et al., (2015) Autophagy 11:2125-2126)), TOM70 (rabbit, 1:5,000, Proteintech, 14528-1-AP)), UBE2L3 (rabbit, 1:10,000, ProteinTech, 14415-1-AP), VDAC1 (mouse, 1:5,000, Abcam, ab14734), vinculin (mouse, 1:100,000, Sigma, V9131).

Mitochondrial Depolarization Assay

Mitochondrial depolarization was assessed using a JC10 assay kit (Sigma, MAK159). HeLa Parkin cells were seeded with 70,000 cells/well in 20 µL volume into 384-well plates with clear bottom. The following day 5 µL of CCCP or compounds were added as 5× solutions. Equal volume of DMSO served as a negative control. Cells were incubated for 4 h before 12.5 µL of JC10 dye diluted in buffer A was added to the wells. One hour later the reaction was stopped with 12.5 µL of buffer B and the plate was measured immediately on a Spectramax M5 plate reader (Molecular devices) with bottom read using dual fluorescence (green: Ex 485 nm, Em 538 nm, cut-off at 515 nm; red: Ex 544 nm, Em 590 nm, cut-off at 570 nm). Mitochondrial depolarization was assessed by building the green to red ratio.

Example 8: Enzymatic Activation of Parkin in HeLa Cells

Figure 13:
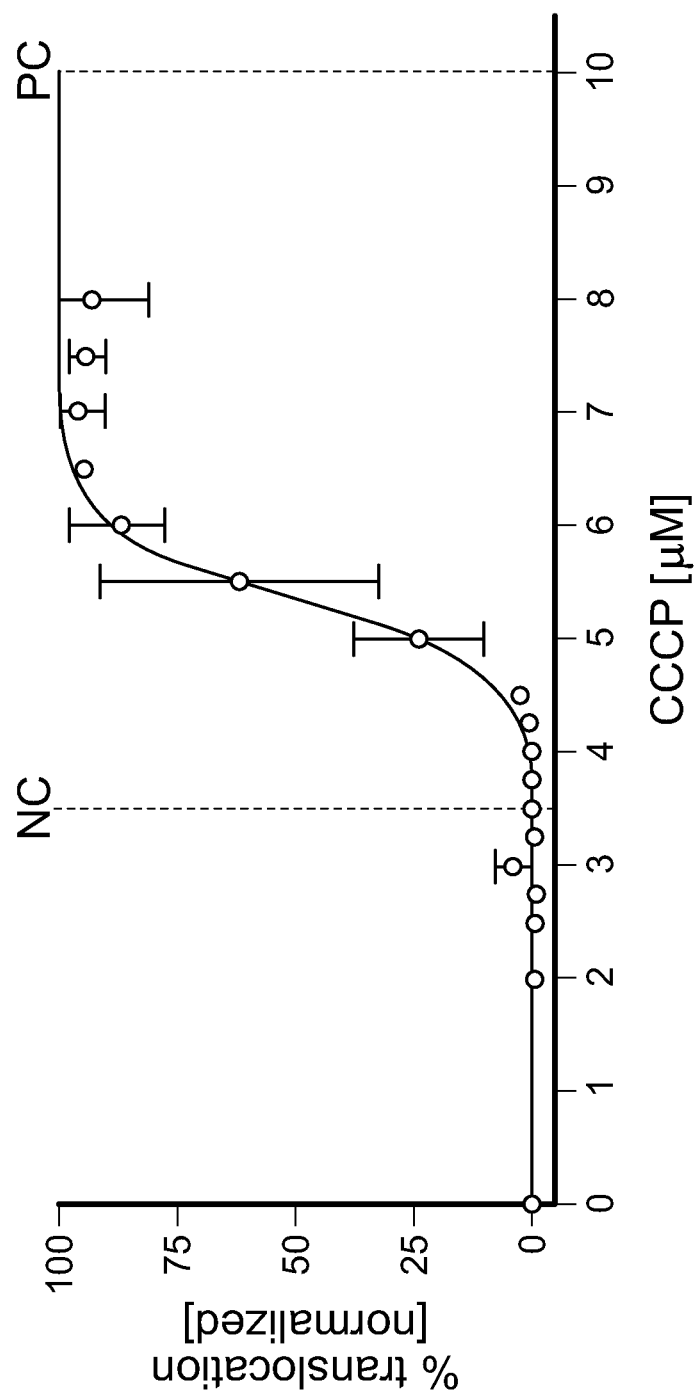
FIG. 13 shows the normalized EGFP-Parkin translocation [%] in response to different CCCP doses.
Figure 14:
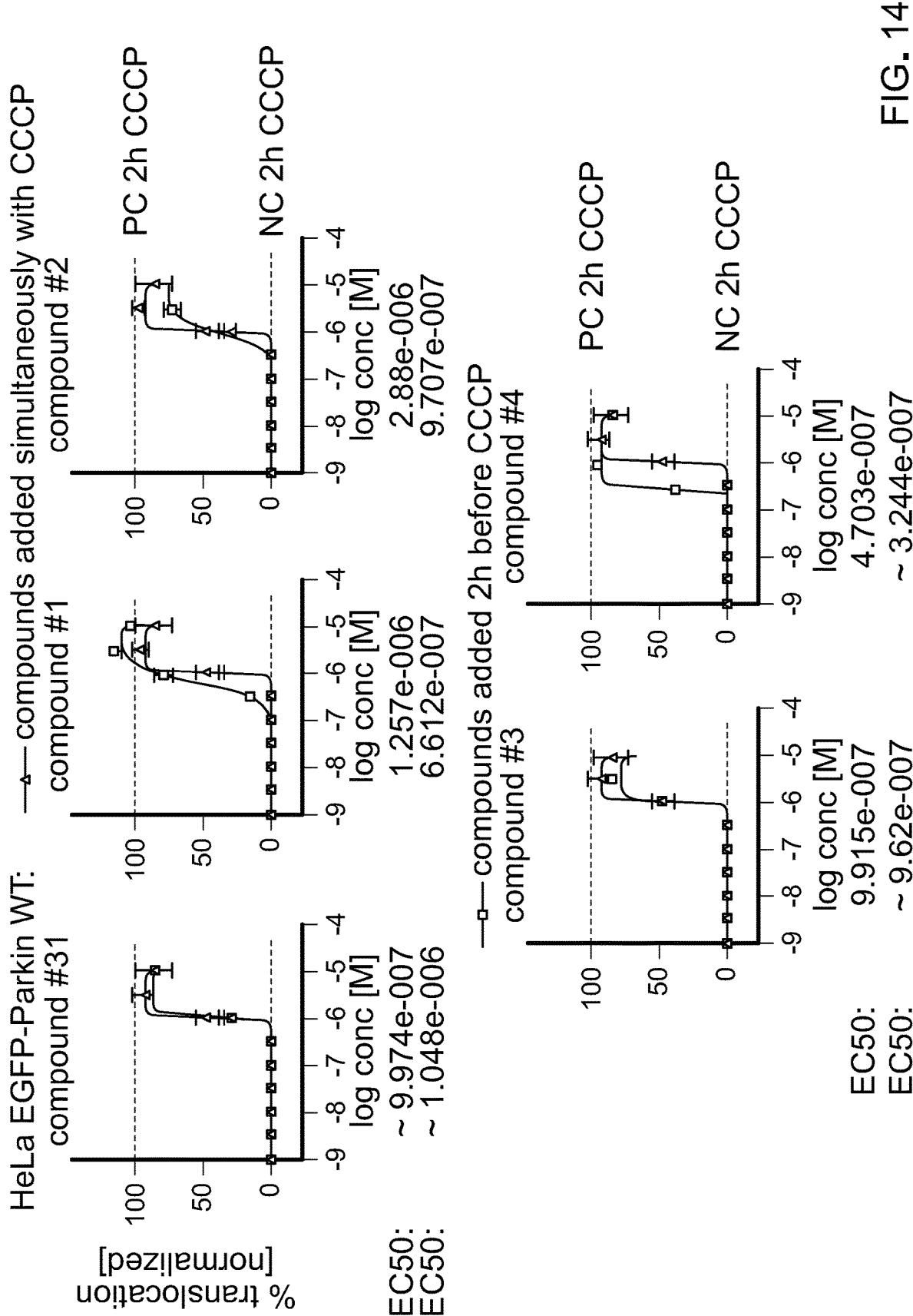
FIG. 14 shows HeLa EGFP-Parkin cells seeded in 384-well plates and treated with 3.5 μM CCCP as the negative control and 10 μM CCCP for the positive control. Cells were either pretreated for 2 h with compounds 1, 2, 3, 4, or 31 before low dose CCCP was added or the compound and CCCP were added at the same time. Cells were fixed and analyzed with HCI for Parkin translocation. Both experimental regimens led to similar $EC_{50}$ values for all five compounds.

Functional testing of compounds was performed using an established primary HCI assay for Parkin translocation, which correlates well with enzymatic activation (Fiesel et al., J. Cell Science (2014) 127:3488-3504; Fiesel et al., Human Mutation (2015) 36:774-786). In brief, 1400 HeLa cells stably expressing EGFP-Parkin were seeded into optical 384-well plates (Greiner BioOne) in 25 µL media and allowed to adhere for 40 h. Compounds 1, 2, 3, 4, and 31 were added to the plate as 2× concentrated stocks. Control wells were treated with equal volume of DMSO in media. After 2 h, unless otherwise stated, CCCP was added as 2× concentrated stock with a final assay concentration of 10 µM for PC wells and 3.5 µM for test and NC wells. This low dose of CCCP was experimentally determined by a dose response curve of CCCP to result in no Parkin translocation (FIG. 13). After another 2 h, cells were fixed in 4% paraformaldehyde for 10 min and stained with Hoechst 33342 (1:5000, Invitrogen) before plates were imaged and analyzed.

Image acquisition was performed on a BD Pathway 855 with the Attovision V1.6 software (BD Biosciences). Wells were imaged with a 20× objective using a 2×2 montage with laser autofocus. EGFP exposure time was 0.0175 sec, Hoechst 0.0015 sec. Raw images were not processed and directly analyzed using a build-in 'RING—2 output' algorithm. Values were exported and normalized using JMP 11 software and transferred to GraphPad Prism 7 for quality control, graphing and curve fitting for DRCs with a variable slope using four parameters. The primary screening assay typically showed S/B of 3.0-3.5 with CV of less than 5%. Values were normalized to both PC and NC values from 24 wells each per plate and the Z' score was calculated. Plates with Z'<0.5 were repeated.

Figure 10:
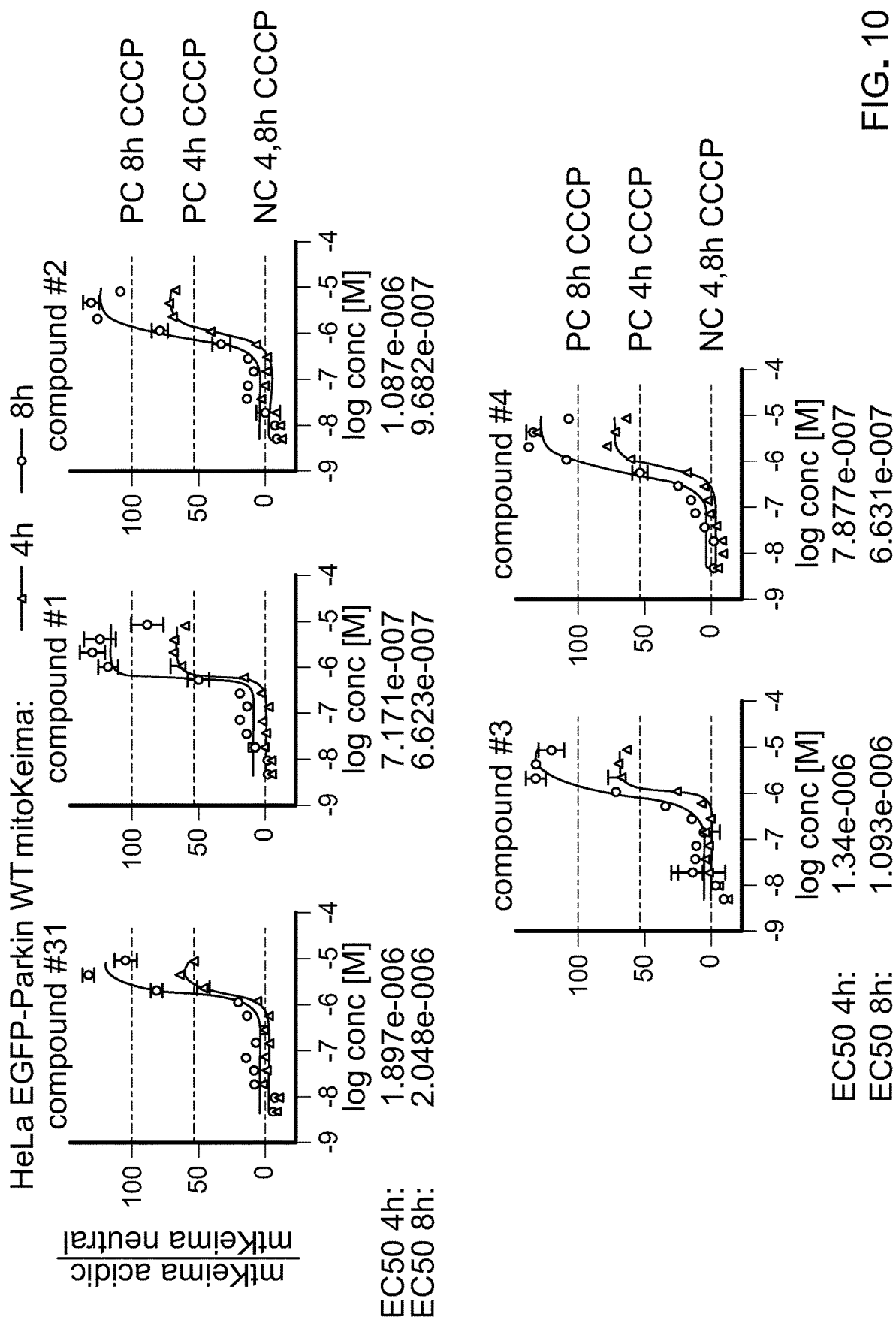
FIG. 10 shows DRCs of Compounds 1, 2, 3, 4, and 31 in a mitophagy assay. HeLa mtKeima cells were pre-treated for 2 h with 12 different doses of Compounds 1, 2, 3, 4, and 31 before low-dose CCCP was added (3 μM final concentration). 10 μM CCCP was added to positive control wells. Cells were imaged live after 4 h and 8 h of CCCP. Values were normalized to the positive and negative (3 μM CCCP) control values for each time point. Curve fitting was used to calculate $EC_{50}$ values.
Figure 11:
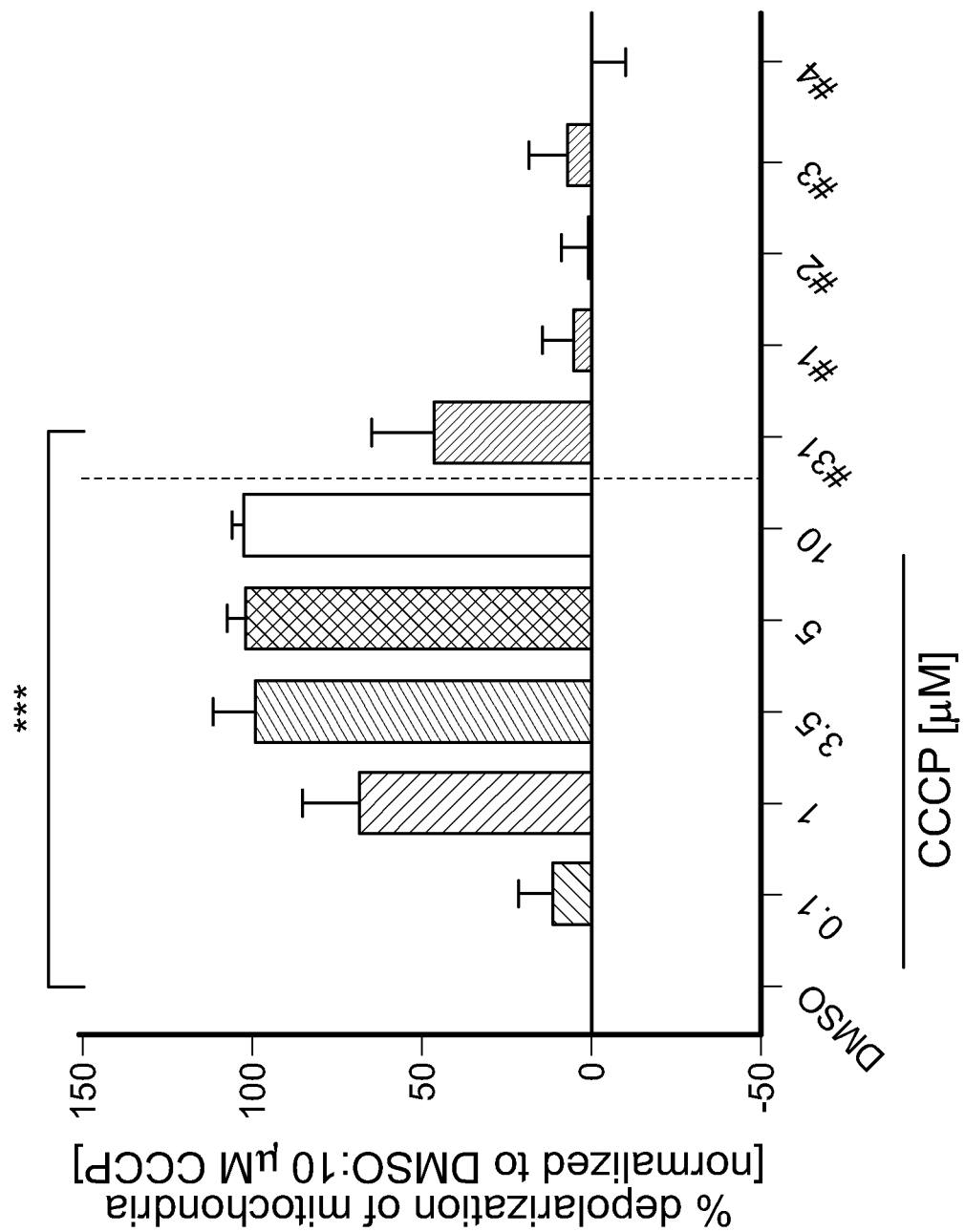
FIG. 11 shows quality control of mitochondrial membrane potential (JC-10 assay) upon treatment with Compounds 1, 2, 3, 4, and 31. In order to exclude compounds that diminish the mitochondrial membrane potential, a JC-10 assay was used. HeLa cells were plated in 384-well plates and treated with different doses of CCCP or with 5 μM of Compounds 1, 2, 3, 4, and 31 as indicated for 2 h. The JC-10 dye was added to the live cells and cells are stained for 45 minutes. The plates were then measured with a fluorescent plate reader. JC-10 is a mitochondrial dye that emits red fluorescence in the presence of mitochondrial membrane potential. The fluorescence will change to green in the absence of mitochondrial membrane potential. While Compounds 1, 2, 3, and 4 did not show an effect on JC-10, Compound 31 significantly increased depolarization of mitochondria compared to the DMSO control. Shown are average values of 3 independent experiments. Statistical analysis was performed by one-way ANOVA with Tukey's post-hoc test. ***, p<0.0005.

High-resolution imaging confirmed enhanced Parkin co-localization with mitochondria after treatment with compounds 1, 2, 3, 4, and 31 and a low dose CCCP. This combination also induced the pSer65-Ub mitophagy tag as detected by antibody staining (Fiesel et al., EMBO Reports (2015) 16:1114-30; Fiesel et al., Autophagy (2015) 11:2125-2126) and further quantified by HCI in DRC format. Compared with Parkin translocation, $EC_{50}$ values for pSer65-Ub signal amplification were similar. Yet, compound wells with higher compound concentrations showed exceeding pSer65-Ub levels compared to PC wells (FIG. 10). No noticeable effect on cell survival was observed for any of the compounds even at high concentrations. Neither compound alone nor low dose CCCP treatment (NC) was sufficient to activate Parkin translocation or induce pSer65-Ub signal amplification, even after prolonged time points.

Figure 8:
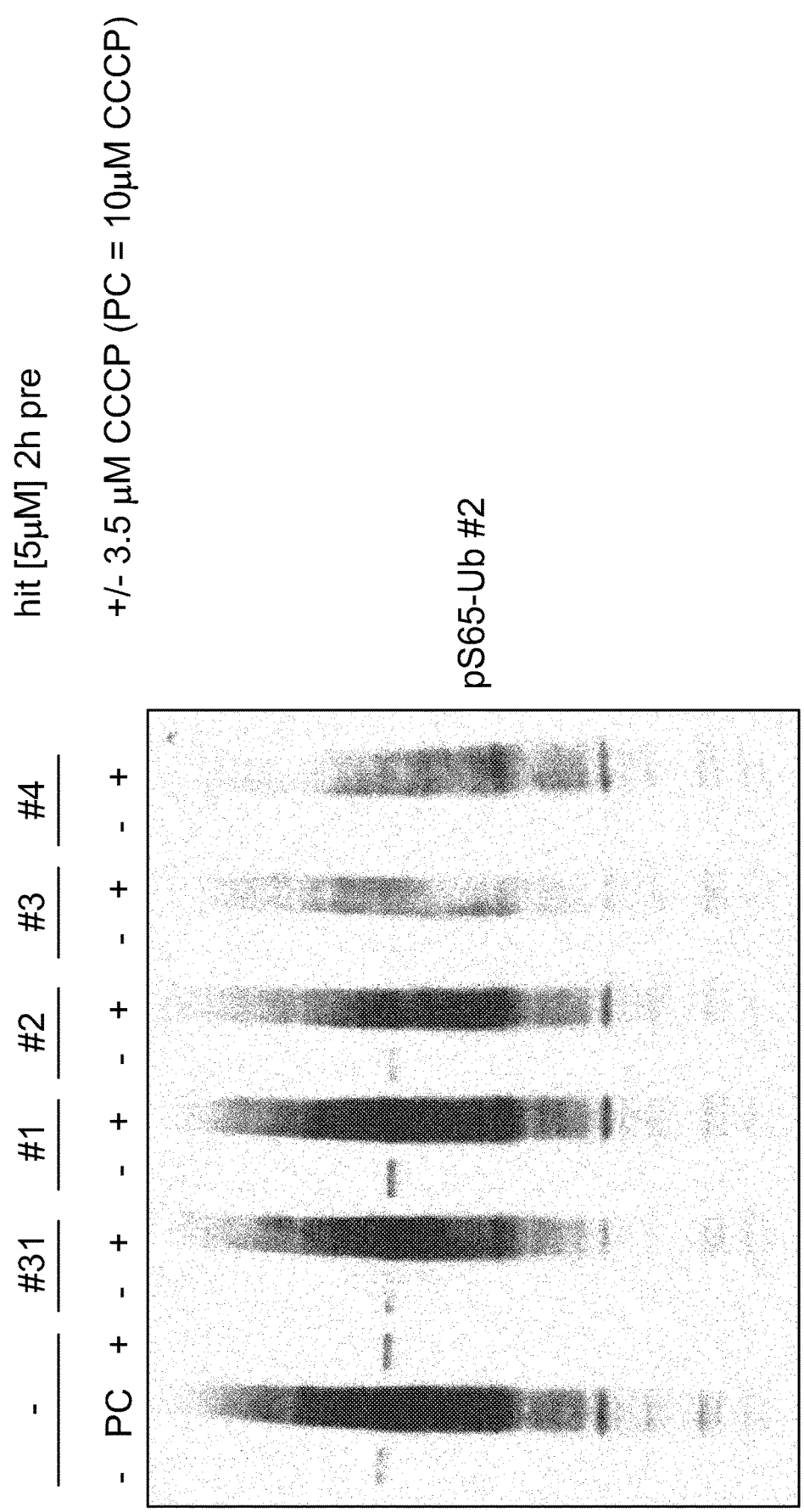
FIG. 8 shows enhanced amplification of pS65-Ub signal by pre-treatment with Compounds 1, 2, 3, 4, and 31. HeLa cells stably expressing untagged Parkin were left untreated or pre-treated with 5 µM of Compounds 1, 2, 3, 4, and 31 for 2 h and treated without (−) or with (+) low dose CCCP (3.5 µM CCCP). The positive control (PC) was treated with 10 µM CCCP for 2 h. Lysates were loaded onto 8-16% Tris-Glycine gels, blotted onto membranes and probed with antibodies against pS65-Ub. While low-dose CCCP treatment alone does not lead to pS65-Ub accumulation, cells treated with Compounds 1, 2, 3, 4, and 31 showed robust induction of pS65-Ub to the positive control.

As readout for its activation, a catalytic site mutant that can be used to trap Ub-charged Parkin was employed. Using HeLa cells stably expressing 3×FLAG-Parkin C431S, and as indicated by an upwards shifted band, Ub-charged Parkin was generally increased with either compound as seen by western blot or by sandwich ELISA. To further validate effects on enhanced activation, we used HeLa cells expressing untagged native Parkin. PC treatment with 10 µM CCCP induced pSer65-Ub signals and the complete degradation of some substrates (e.g., Mitofusins) while the most abundant, VDAC1, was still ubiquitylated (FIG. 8). Similar effects were seen when cells had been pre-incubated with 5 µM of compound before a low dose CCCP, which had no effect on its own.

Example 9: Downstream Mitophagy Activation in HeLa Cell Lines

To validate the activation of Parkin further downstream in the pathway, co-recruitment of endogenous autophagy receptors to mitochondria in HeLa EGFP-Parkin cells was analyzed. These dual adaptors recognize pSer65-Ub chains on damaged mitochondria and facilitate their engulfment by autophagosomal membrane via their interaction with LC3 proteins (Lazarou et al., Nature (2015) 524:309-14; Heo et al., Mol. Cell (2015) 60:7-20).

For pSer65-Ub analysis (Puschmann et al., Brain (2017) 140:98-117 (2017); Fiesel et al., EMBO Reports (2015) 16:1114-30 (2015); Ando et al., Mol. Neurodegen. (2017) 12:32), EGFP-Parkin HeLa cells were seeded and treated as above. After fixation, cells were permeabilized with 1% Triton X-100 in PBS for 10 min and blocked in 10% goat serum for 1 h. 20 µL of primary anti-pSer65-Ub antibody (1:500 in 1% BSA in PBS) were added per well and incubated for 1 h. After washing, goat anti-rabbit AlexaFluor-568 antibody was added for 1 h. Nuclei were counterstained with Hoechst 33342 (1:5000 in PBS) before plates were imaged as described above with additional acquisition for red fluorescence (exposure time 0.05 sec). pSer65-Ub signal was analyzed after segmentation as above as the signal intensity in the cytoplasmic ring.

All five compounds (1, 2, 3, 4, and 31) increased co-localization of OPTN and of NBR1, NDP52, p62, and TAX1BP1 with Parkin on damaged mitochondria. Concomitant with enhanced recruitment of autophagy adaptors, a robust reduction of mitochondrial DNA in immunofluorescence staining was observed.

To confirm mitophagy, HeLa cells expressing the pH-sensitive, mitochondria-targeted reporter mitoKeima46 were employed. A characteristic shift in the excitation wavelength of mitoKeima upon lysosomal fusion was used to determine mitochondrial turnover using HCl. For mitoKeima experiments (Kim et al., Mol. Neurodegen. (2016) 11:55), cells were seeded in DMEM media lacking phenol red in L per well. Hoechst counterstain was added as a 5× stock in 5 µL volume. Cells were treated with 2× stock solutions of compounds and of CCCP as above. Equal amounts of DMSO were used for controls. Cells were imaged live and autofocus was used for each time point. Exposure times of neutral and acidic mitoKeima were 0.02 and 0.05 sec, respectively. Segmentation of cells was performed as above and for each region of interest the ratio of acidic and neutral mitoKeima was calculated. Values were normalized to the positive and negative controls.

Figure 9:
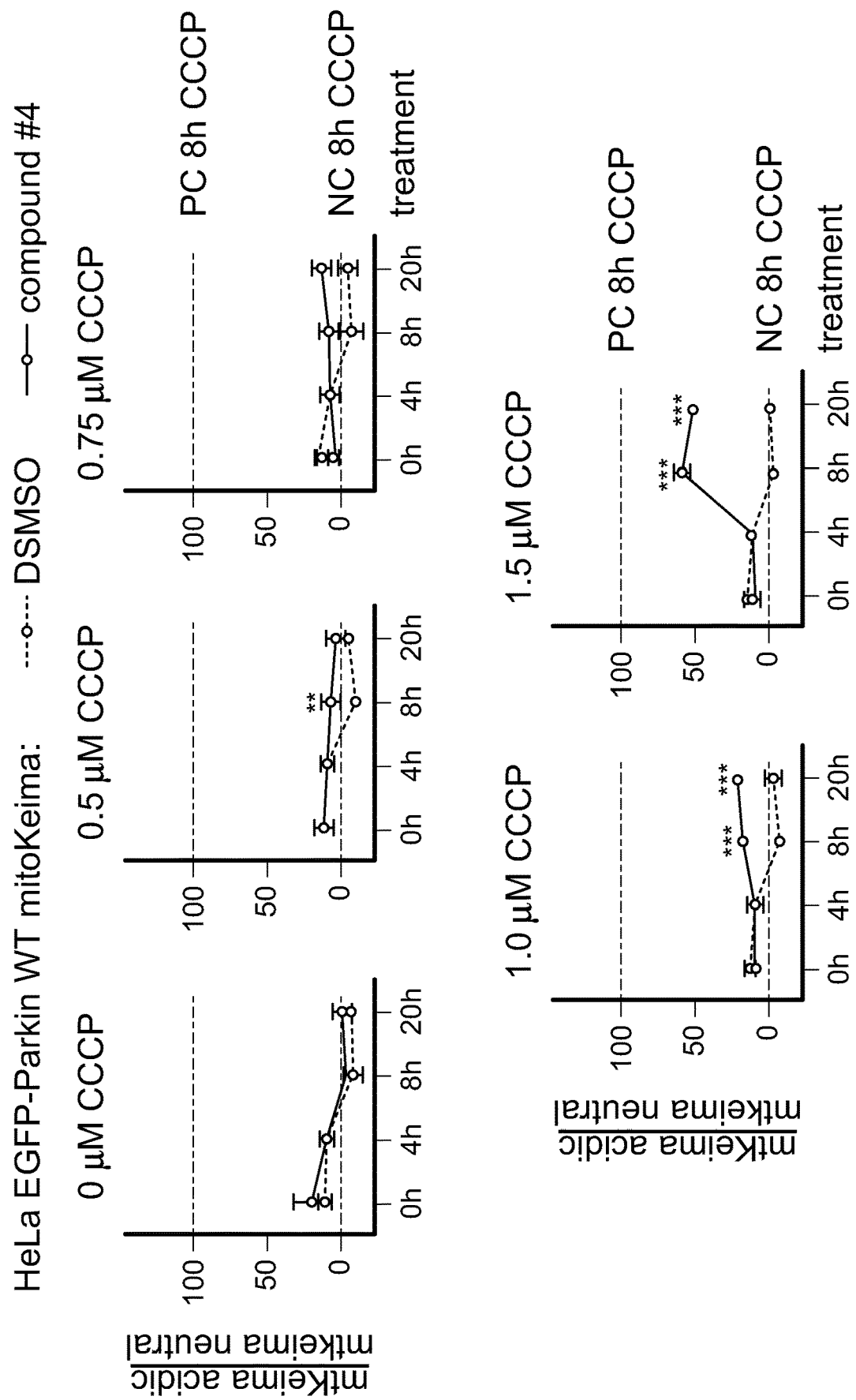
FIG. 9 shows enhanced mitophagy flux upon pre-treatment with compound 4 in the presence of mitochondrial damage. HCI in 384-well plates was used to calculate the ratio of acidic to neutral mtKeima. Upon treatment with 10 μM CCCP, there was significant increase of the mtKeima ratio. Pre-treatment with compound 4 (dashed line, here shown 5 μM of compound 4) induced this also at low-dose CCCP concentrations while low dose CCCP alone (solid line) had only little effect on the ratio of acidic to neutral mtKeima.
Figure 9:
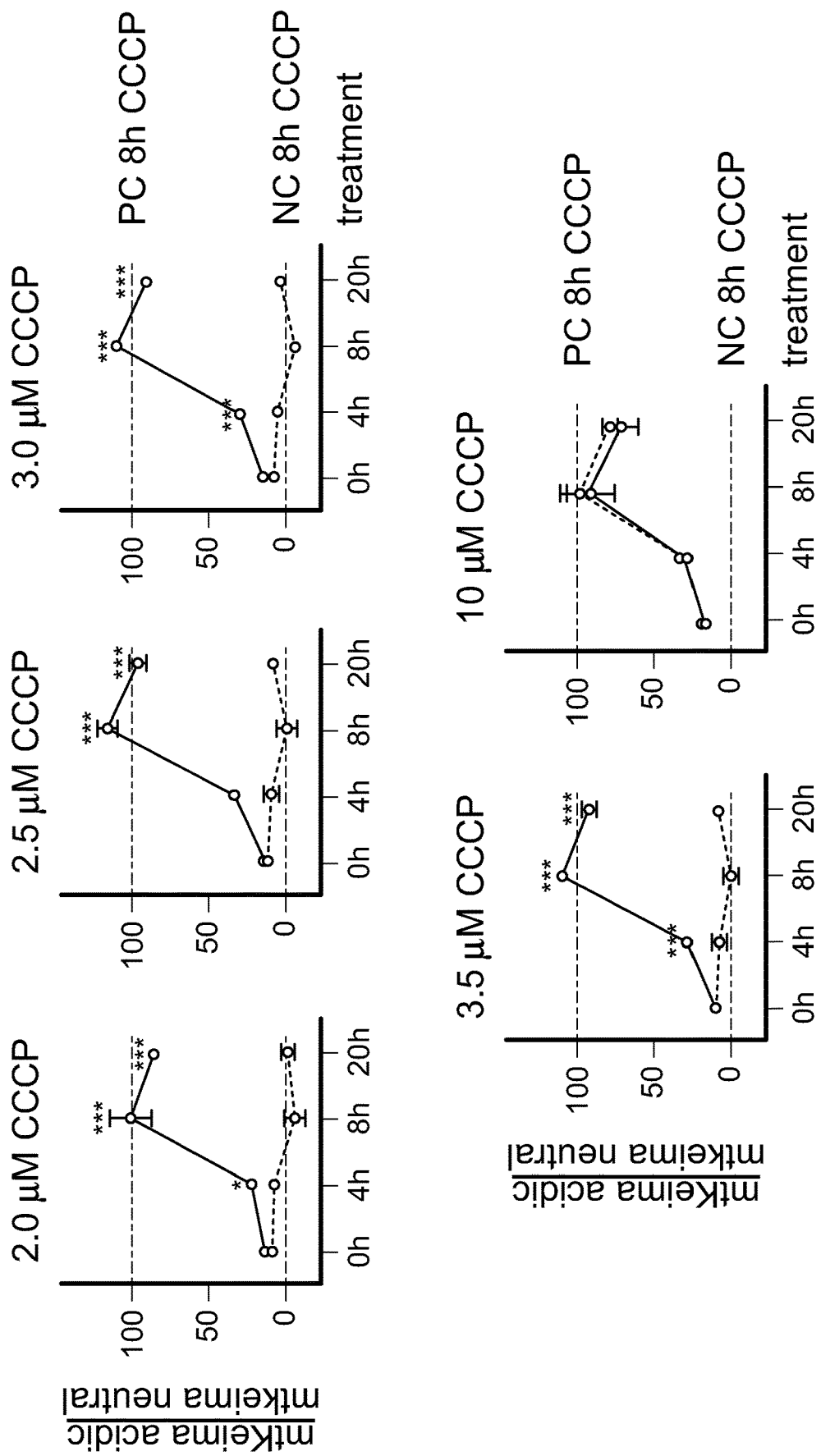
Figures 15A, 15B:
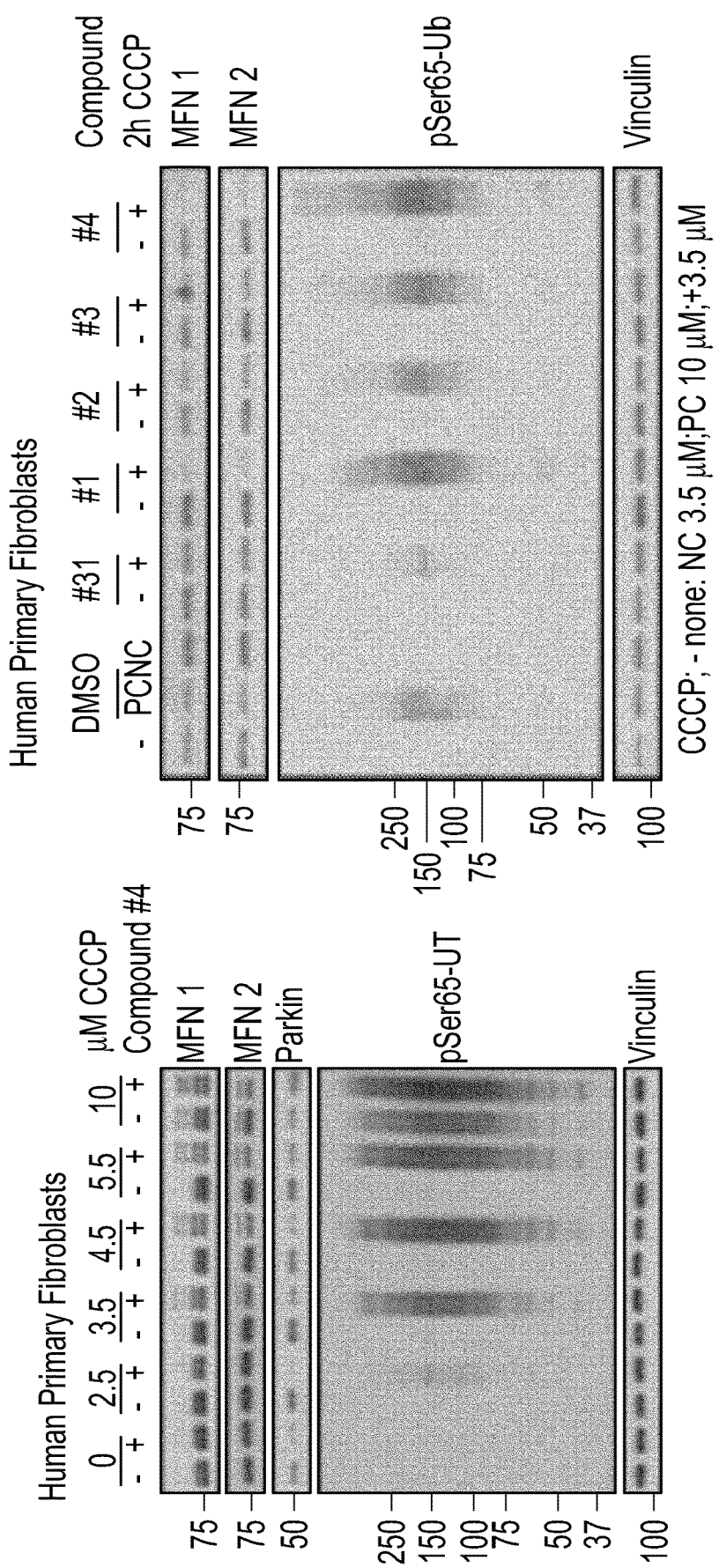
Figures 16A, 16B:
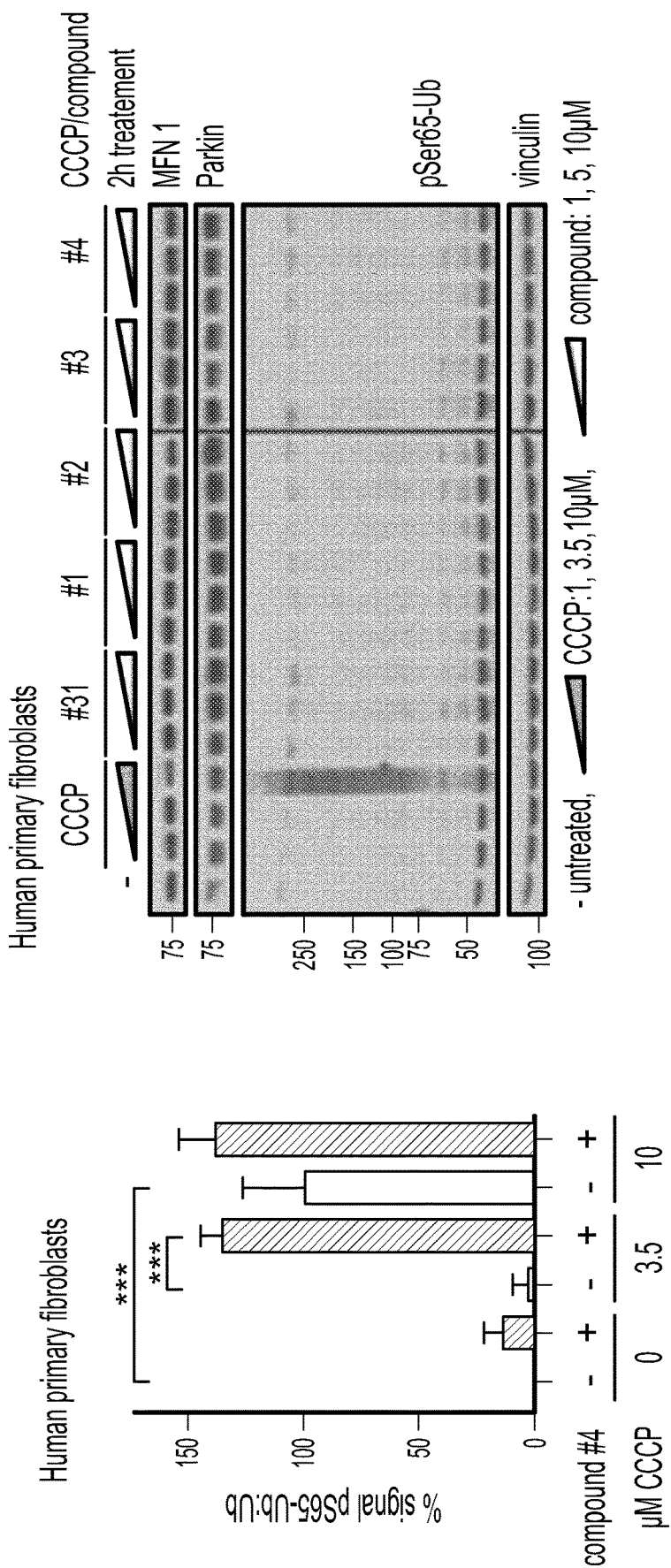
FIGS. 16A-16D shows effects in primary and neuronal cells.

Treatment with compound 4 in combination with various CCCP concentrations (≥1 µM) resulted in a dose and time-dependent increase of mitophagy, similar to the high dose positive control (FIG. 9). Peak values were obtained after 8 h of treatment indicating that a portion of the mitochondria had already been removed. Cells treated with low dose CCCP alone (up to 3.5 µM), did not show any increase of mitoKeima acidification even at later time points. To determine $EC_{50}$ values for the mitophagy assay, compounds 1, 2, 3, 4, and 31 were tested in DRC format. Curve fit of data points after 4 and 8 h resulted in the same trend in terms of potency within the group as the other quantitative assays (FIG. 10). The activities of the compounds were in the nano- to micromolar range, comparable with their potency in the Parkin translocation and pSer65-Ub amplification assays Example 10: Parkin Activation in Primary Cells and Neuronal Cultures To validate Parkin activating drugs in primary cells, compound 4 was tested in combination with different low dose CCCP concentrations in human dermal fibroblasts. Similar to HeLa cells, 3.5 µM CCCP alone was not sufficient to induce a mitophagy response. When cells were pretreated with compound 4 followed by a low dose CCCP, enhanced ubiquitylation of the Parkin substrates MFN1/2 was observed (FIG. 15A). Consistently, treatment with compound 4 significantly induced pSer65-Ub levels in the presence of low dose CCCP (FIG. 18A). This NC concentration was used to test all five compounds side by side and found that while all five compounds induced a response to a certain extent, compounds 1 and 4 showed the strongest effects on MFN1/2 degradation and pSer65-Ub induction (FIG. 15B). In the absence of CCCP, the compounds did not induce any mitoQC response in primary fibroblast. Additionally, compounds with concentrations ten times higher than the $EC_{50}$ for Parkin translocation did not induce a mitoQC response (FIG. 16B).

Figures 16C, 16D:
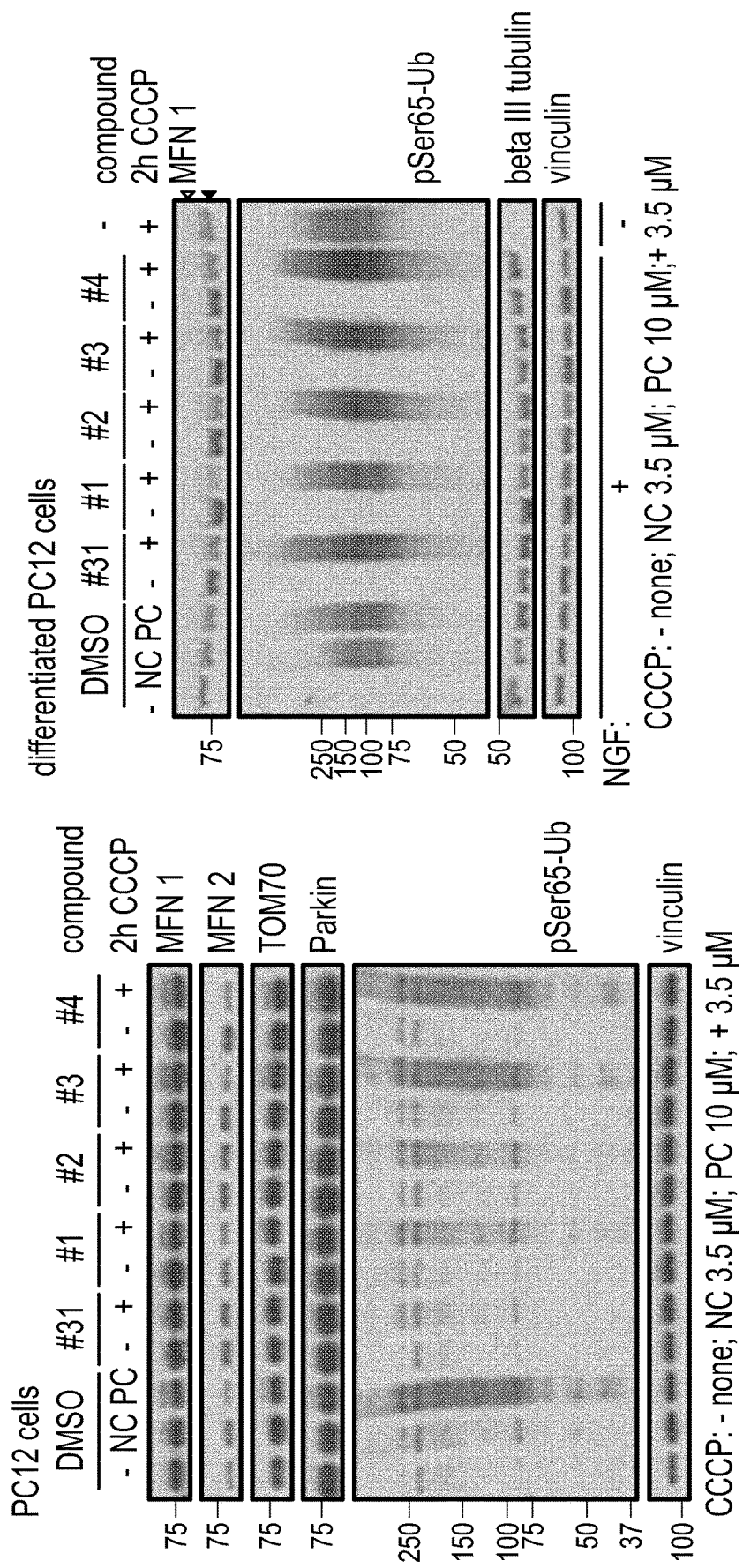

Next, induced Neurons (iNeurons) were generated from the fibroblast cultures. Neuronal conversion was confirmed by the neuronal marker beta-III-tubulin. While there was only a subtle effect on MFN1 ubiquitylation, all five compounds robustly induced pSer65-Ub levels (FIG. 15C). To ensure that compounds could also be used in an animal model, their ability to activate endogenous Parkin in rat PC-12 cells was tested. All five compounds robustly induced pSer65-Ub in undifferentiated (FIG. 15D and FIG. 16C) and neuronal differentiated cells (FIG. 15D), although here 3.5 µM CCCP alone did induce pSer65-Ub slightly. Nevertheless, cells pretreated with compounds showed more pronounced substrate ubiquitylation and degradation comparable to PC cells that were treated with 10 µM CCCP (see FIG. 15C and FIGS. 16C-16D).

Example 11: In Vitro Enzyme Activity and Drug Binding

Figures 15E, 15F:
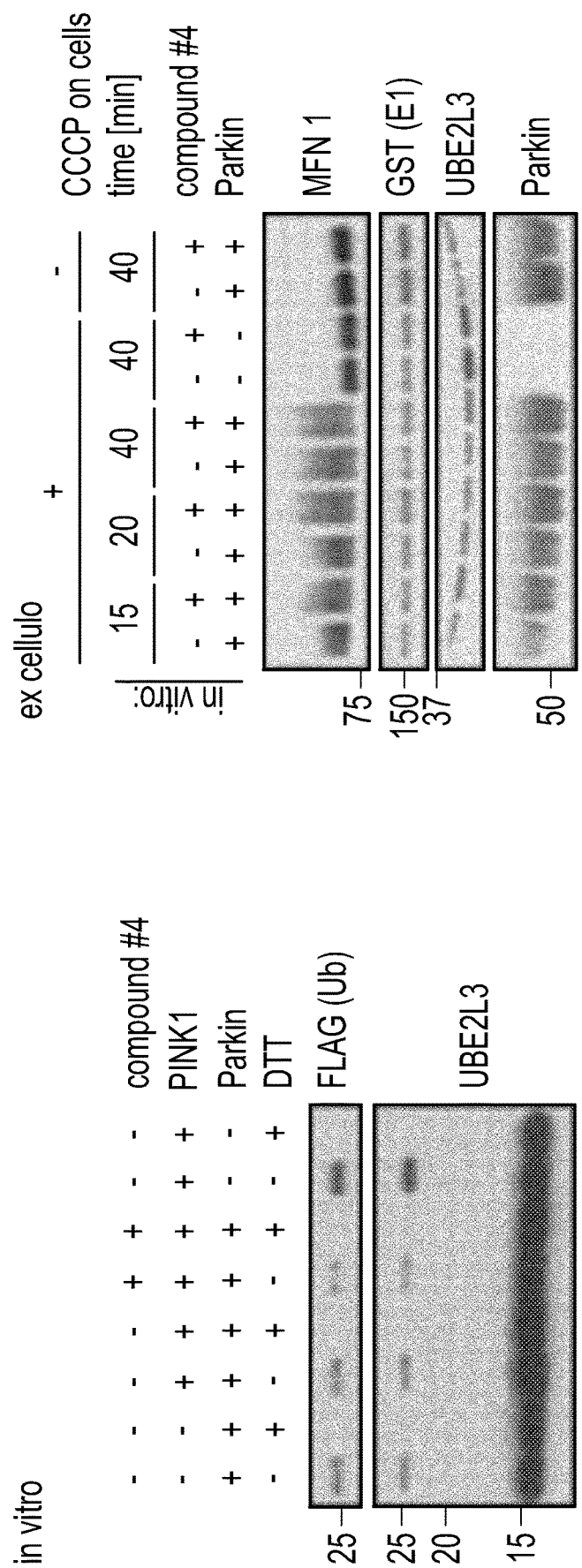

To demonstrate on-target effects of the compounds, in vitro assays with recombinant, purified Parkin protein were performed. As the first readout for Parkin activity, E2 Ub discharge assays were performed, complementary to the Ub-charging assays of Parkin C431S in cells. UbcH7 was first loaded with Ub and then mixed with Parkin that had been pre-incubated with compound 4 or DMSO as control. Only in the presence of PINK1, compound 4 led to more E2 discharge compared to control, consistent with enhanced Ub transfer onto the E3 enzyme (FIG. 15E). The in vitro E2 discharge assays were performed as follows.

Ub-charging of E2 enzyme was performed for 90 min at 30° C. in a reaction containing 0.1 µM GST-E1, 3.3 µM E2/UbcH7, 10 µM FLAG-Ub and 0.188 µM PINK1 (all R&D systems). In a separate reaction 0.75 µM Parkin (Ubiquigent) was preincubated with 20 µM compound 4 (or equal volume of DMSO). Both reactions were diluted in Ub buffer (final concentration: 20 mM HEPES pH 7.2, 10 mM MgCl$_2$, 0.1 mM EGTA, 500 µM TCEP and 10% ATP regeneration system (20 mM HEPES pH 7.6, 10 mM ATP, 300 mM phosphocreatine, 10 mM MgCl$_2$, 10% glycerol, 1.5 mg/mL creatine phosphokinase (all Sigma Aldrich))). 1 U Apyrase (Sigma) was added per 9 µL reaction and both reactions were combined and incubated for an additional 30 min. 100 µL of 1×LDS buffer was added per 10 µL reaction and samples were split for −/+DTT (20 mM final).

To provide substrates for Parkin ligase activity, mitochondrial fractions for an ex cellulo ubiquitylation assay were provided. These samples were prepared from HeLa cells that express PINK1, but lack Parkin and that had been left untreated or were treated with 10 µM CCCP for 2 h. Aliquots were resuspended in reactions containing recombinant purified E1, E2, Ub and Parkin as well as ATP and either compound 4 or DMSO as a control. Mono-ubiquitylation of MFN1 was observed in the absence of compound, but poly-ubiquitylation was robustly induced when compound 4 was added to the reaction, especially at shorter time points (FIG. 15E). Notably, there was no effect when mitochondria were isolated from cells that were left untreated (i.e., no PINK1).

The in vitro assays with mitochondrial preparations were performed as follows. HeLa cells were either left untreated or treated with 10 µM CCCP for 2 h. Cells were harvested in solution B (20 mM HEPES pH 7.6, 220 mM mannitol, 70 mM sucrose, 10 mM KAc containing EDTA-free Complete and PhosStop) and homogenized by 10 strokes through a 23 G needle followed by 10 strokes through a 27 G needle. Lysates were centrifuged for 5 min at 800 g and supernatant spun for 20 min at 8000 g to pellet mitochondria. The mitochondrial pellet was resuspended in solution B and the protein concentration determined by BCA. Aliquots of 50 µg were prepared, spun at 20,000 g for 5 min, the supernatant removed and stored at −80° C. The in vitro reaction was prepared in Solution B buffer and contained 45 µM Ub, 0.1 µM GST-E1, 1 µM E2/UbcH7, 2 mM DTT and 1 µL of ATP regeneration system per 10 µL reaction. Reactions with 0.75 µM Parkin were prepared as one mix that was split in different reactions before compound (20 µM) or DMSO was added. Reactions were incubated at 37° C. for 2 h and 10 µL were added per 50 µg mitochondria. Samples were incubated at 30° C. for the indicated time points, centrifuged, washed once with solution B before mitochondrial pellet was resuspended in 100 µL LDS buffer containing 100 mM DTT and 1% Triton X-100. The supernatant of the reaction (8 µL) was saved and mixed with 32 µL 2×LDS buffer. Samples were heated to 35° C. shaking for 30 min before gel loading.

Figure 15H:
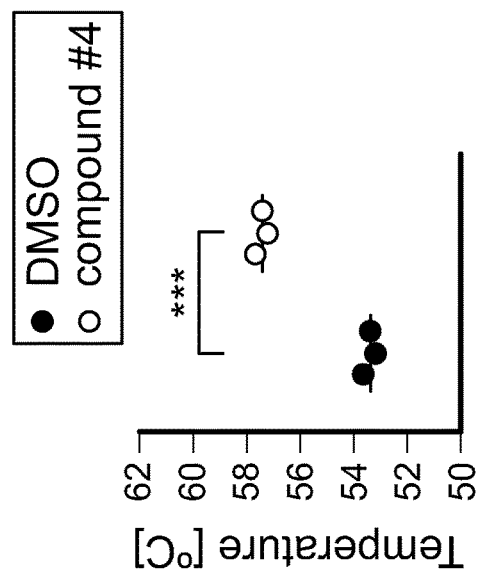
Figure 15G:
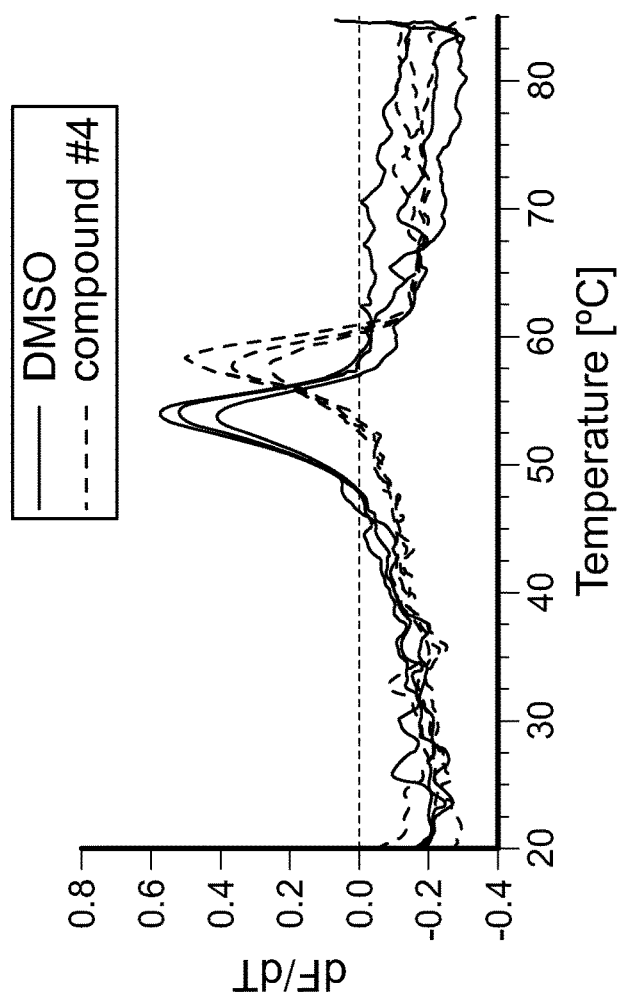

To validate direct binding of activating compounds to Parkin as predicted from the in silico approach, a thermofluor shift assay was used. Recombinant purified Parkin was mixed together with compound 4 or DMSO as a control and the melting temperature was monitored using SYPRO Orange dye. Addition of compound 4 significantly elevated the melting temperature of Parkin (FIGS. 15G-15H) suggesting the direct association of Parkin and drug. This result, together with the cell culture data and in vitro experiments corroborate that PINK1-dependent priming of Parkin is required for compound activity as predicted from the MDS.

The thermal shift assay was performed as follows. Per sample (5 µL), 50 ng of Parkin (Ubiquigent) was mixed with 0.5 µL ⅟₅₀ diluted SYPRO Orange (Invitrogen), 0.5 µL 10× buffer (200 mM HEPES pH 7.6, 100 mM MgCl$_2$, 20 mM DTT and 1 mM EGTA) and 0.5 µM compound or equivalent amounts of DMSO. Samples were run in opaque 384-well plates on a LightCycler 480 system (Roche Applied Science) in a melt curve analysis with 10 acquisitions per ° C. Data was exported and analyzed using the Protein Melting Analysis tool (Roche Applied Science).

Example 12: Parkin Binding to Ubiquitin

Figure 21:
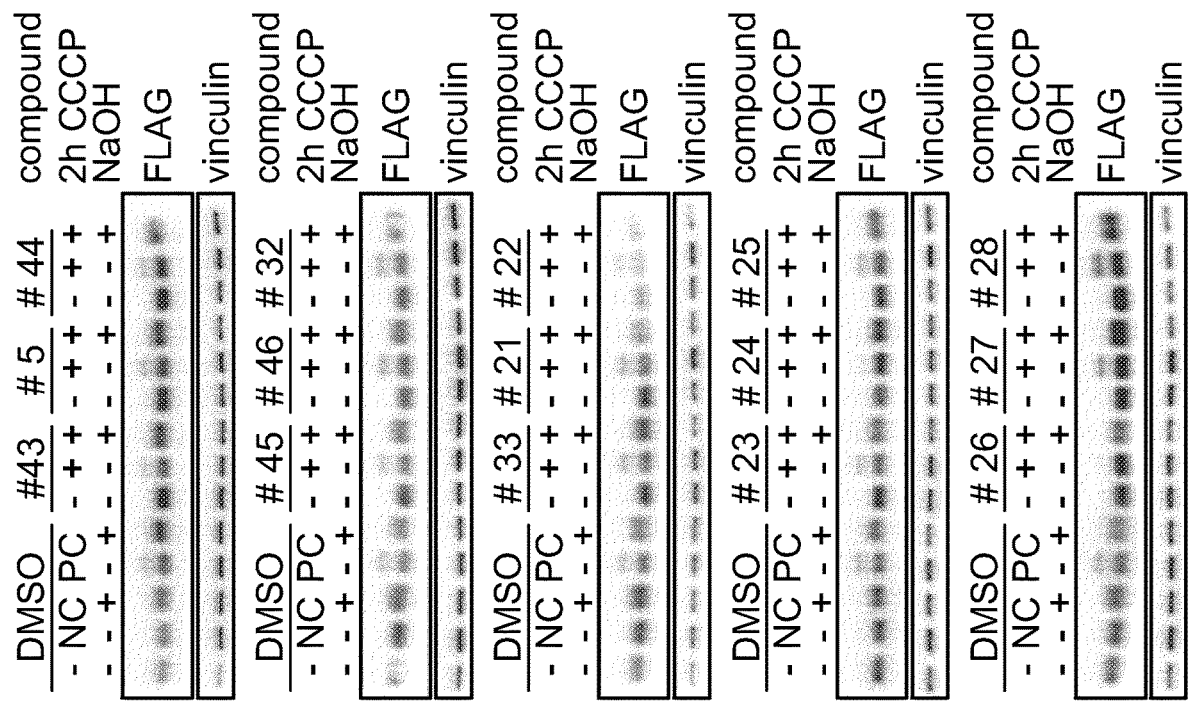
FIG. 21 shows enhanced Ub-charging of FLAG-Parkin C431S (WB) by pre-treatment with compounds 5, 21-28, 32, 33, and 43-46. Band shift indicates Parkin binding to Ubiquitin, which is cleavable with NaOH.

HeLa 3×FLAG-Parkin C431S cells were seeded in 6-well plates and allowed to attach overnight. Cells were treated with 1 pVM of compounds 5, 21-28, 32, 33, or 43-46 2 h before adding CCCP for another 2 h. 10 VM CCCP was added to positive control (PC) wells, 3.5 µM CCCP to compound (+) and negative control (NC) wells. Some samples did not receive CCCP (−). Cells were harvested in boiling hot SDS lysis buffer and protein concentration was determined by BCA. Samples were split and left either untreated or were treated with NaOH as indicated. Samples were run on an 8-16% Tris-Glycine gel, blotted onto membranes and probed with antibodies against Flag. Vinculin served as a loading control. Band shift indicates Parkin binding to Ubiquitin, which is cleavable with NaOH (FIG. 21).

INCORPORATION BY REFERENCE

The entire disclosure of each of the patent documents and scientific articles referred to herein is incorporated by reference for all purposes.

EQUIVALENTS

The disclosure can be embodied in other specific forms without departing from the spirit or essential characteristics thereof. The foregoing embodiments are therefore to be considered in all respects illustrative rather than limiting on the disclosure described herein. Scope of the disclosure is thus indicated by the appended to claims rather than by the foregoing description, and all changes that come within the meaning and range of equivalency of the claims are intended to be embraced therein.

What is claimed is:

1. A compound of Formula I:

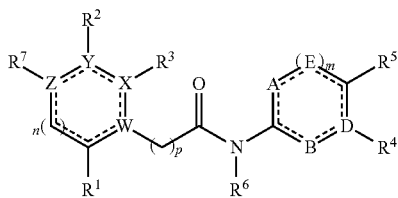

or a pharmaceutically acceptable salt thereof, wherein:
A is CH;
B is N;
D is C or N;
E is CH;
W is N;
X is C;
Y is C;
Z is N;
$R^1$ is H, $C_{1-4}$ alkyl, phenyl, or hetAr$^1$;
$R^2$ is H;
$R^3$ is H;
or $R^2$ and $R^3$, together with Y and X, form a 6-membered cycloalkyl ring;
$R^7$, if present, is H;
$R^4$, if present, is H, $C_{1-4}$ alkyl, halogen, $CF_3$, or phenyl;
$R^5$ is $C_{1-4}$ alkyl, $C_{4-10}$ cycloalkyl, phenyl optionally substituted with halogen, $(C_{1-3}$ alkyl)O($C_{4-6}$cycloalkyl), O($C_{1-4}$ alkyl)($C_{4-6}$ cycloalkyl), S($C_{1-4}$ alkyl), S($C_{4-6}$ cycloalkyl), $(C_{1-3}$ alkyl)($C_{4-9}$ hetCyc$^1$), hetAr$^1$, or O(phenyl) optionally substituted with CN;
$R^6$ is H or $C_{1-4}$ alkyl;
hetAr$^1$ is independently at each occurrence a 6-membered heteroaryl ring having 1-3 ring nitrogen atoms optionally substituted with $C_{1-4}$ alkyl;
hetCyc$^1$ is a 6-10-membered bicyclic ring having at least one ring heteroatom which is nitrogen and at least one of the rings is aromatic;
m is 1;
n is 0;
p is 0 or 1; and
the dashed lines can be single or double bonds.

2. The compound of claim 1, wherein D is C.
3. The compound of claim 1, wherein D is N.
4. The compound of claim 1, wherein $R^1$ is H.
5. The compound of claim 1, wherein $R^1$ is $C_{1-4}$ alkyl or hetAr$^1$.
6. The compound of claim 1, wherein $R^1$ is methyl, isopropyl, phenyl, or pyridine.
7. The compound of claim 1, wherein $R^4$ is H.
8. The compound of claim 1, wherein $R^4$ is Cl, $CF_3$, methyl or phenyl.
9. The compound of claim 1, wherein $R^5$ is phenyl optionally substituted with halogen.
10. The compound of claim 1, wherein $R^5$ is $(C_{1-3}$ alkyl)O($C_{4-6}$ cycloalkyl), O($C_{1-4}$ alkyl)($C_{4-6}$ cycloalkyl), or O(phenyl) optionally substituted with CN.
11. The compound of claim 10, wherein $C_{4-6}$ cycloalkyl is cyclopentyl or cyclohexyl.
12. The compound of claim 1, wherein $R^5$ is S($C_{1-4}$ alkyl) or S($C_{4-6}$ cycloalkyl).
13. The compound of claim 1, wherein $R^5$ is hetAr$^1$.
14. The compound of claim 13, wherein hetAr$^1$ is pyridine or pyrimidine optionally substituted with $C_{1-4}$ alkyl.
15. The compound of claim 1, wherein $R^6$ is H.
16. The compound of claim 1, wherein p is 1.
17. The compound of claim 1, wherein the compound of Formula I is selected from the group consisting of:

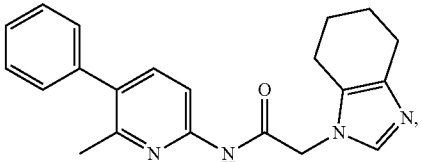

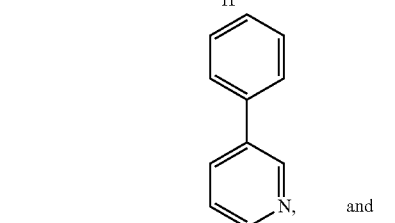

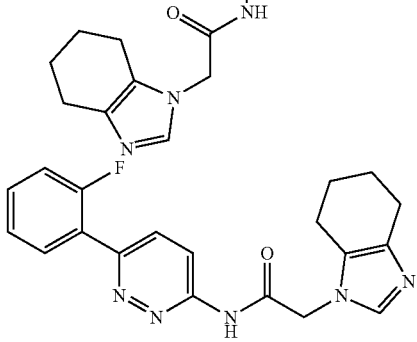

or a pharmaceutically acceptable salt thereof.

18. A pharmaceutical composition comprising a compound of claim 1 or a pharmaceutically acceptable salt thereof, and at least one pharmaceutically acceptable carrier.

19. A method of activating the enzymatic activity of an E3 ubiquitin ligase in a subject, the method comprising administering to the subject a therapeutically effective amount of a compound of Formula I:

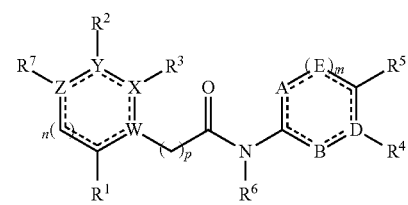

or a pharmaceutically acceptable salt thereof, wherein:
A is CH;
B is N;
D is C or N;

E is CH;
W is N;
X is C;
Y is C;
Z is N;
$R^1$ is H, $C_{1-4}$ alkyl, phenyl, or $hetAr^1$;
$R^2$ is H;
$R^3$ is H;
or $R^2$ and $R^3$, together with Y and X, form a 6-membered cycloalkyl ring;
$R^7$, if present, is H;
$R^4$, if present, is H, $C_{1-4}$ alkyl, halogen, $CF_3$, or phenyl;
$R^5$ is $C_{1-4}$ alkyl, $C_{4-10}$ cycloalkyl, phenyl optionally substituted with halogen, ($C_{1-3}$ alkyl)O($C_{4-6}$ cycloalkyl), O($C_{1-4}$ alkyl)($C_{4-6}$ cycloalkyl), S($C_{1-4}$ alkyl), S($C_{4-6}$ cycloalkyl), ($C_{1-3}$ alkyl)($C_{4-9}$ $hetCyc^1$), het $Ar^1$, or O(phenyl) optionally substituted with CN;
$R^6$ is H or $C_{1-4}$ alkyl;
$hetAr^1$ is independently at each occurrence a 6-membered heteroaryl ring having 1-3 ring nitrogen atoms optionally substituted with $C_{1-4}$ alkyl;
$hetCyc^1$ is a 6-10-membered bicyclic ring having at least one ring heteroatom which is nitrogen and at least one of the rings is aromatic;
m is 1;
n is 0;
p is 0 or 1; and
the dashed lines can be single or double bonds.

20. A method of treating a disease or disorder associated with diminished E3 ubiquitin ligase enzymatic activity in a subject, the method comprising administering to the subject a therapeutically effective amount of a compound of Formula I:

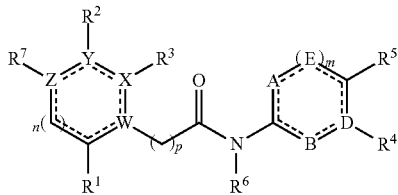

or a pharmaceutically acceptable salt thereof, wherein:
A is CH;
B is N;
D is C or N;
E is CH;
W is N;
X is C;
Y is C;
Z is N;
$R^1$ is H, $C_{1-4}$ alkyl, phenyl, or $hetAr^1$;
$R^2$ is H;
$R^3$ is H;
or $R^2$ and $R^3$, together with Y and X, form a 6-membered cycloalkyl ring;
$R^7$, if present, is H;
$R^4$, if present, is H, $C_{1-4}$ alkyl, halogen, $CF_3$, or phenyl;
$R^5$ is $C_{1-4}$ alkyl, $C_{4-10}$ cycloalkyl, phenyl optionally substituted with halogen, ($C_{1-3}$ alkyl)O($C_{4-6}$ cycloalkyl), O($C_{1-4}$ alkyl)($C_{4-6}$ cycloalkyl), S($C_{1-4}$ alkyl), S($C_{4-6}$ cycloalkyl), ($C_{1-3}$ alkyl)($C_{4-9}$ $hetCyc^1$), het $Ar^1$, or O(phenyl) optionally substituted with CN;
$R^6$ is H or $C_{1-4}$ alkyl;
$hetAr^1$ is independently at each occurrence a 6-membered heteroaryl ring having 1-3 ring nitrogen atoms optionally substituted with $C_{1-4}$ alkyl;
$hetCyc^1$ is a 6-10-membered bicyclic ring having at least one ring heteroatom which is nitrogen and at least one of the rings is aromatic;
m is 1;
n is 0;
p is 0 or 1; and
the dashed lines can be single or double bonds;
wherein the disease or disorder is selected from the group consisting of Parkinson's disease, parkinsonism, Alzheimer's disease, dementia, Amyotrophic lateral sclerosis, Frontotemporal dementia, autism, depression, progeroid disorder, leprosy, an inclusion body myositis, diabetes mellitus, diabetic kidney disease, a liver disease, a lysosomal storage disorder, a neurological disease, a muscular disease, a mitochondrial disease, and cancer.

21. The method of claim 20, wherein the E3 ubiquitin ligase is selected from the group consisting of Parkin, ARIH1 (HEART), ARIH2 (TRIAD1), RNF31 (HOIP), RBCK1 (HOIL-1L), MUL1 (MAPL, MULAN), MARCH5 (MITOL), E3A, mdm2, anaphase-promoting complex (APC), UBR5 (EDD1), SOCS, LNXp80, CBX4, CBLL1, HACE1, HECTD1, HECTD2, HECTD3, HECW1, HECW2, HERC1, HERC2, HERC3, HERC4, HUWE1, ITCH, NEDD4, NEDD4L, PPIL2, PRPF19, PIAS1, PIAS2, PIAS3, PIAS4, RANBP2, RNF4, RBX1, SMURF1, SMURF2, STUB1, TOPORS, TRIP12, UBE3A, UBE3B, UBE3C, UBE4A, UBE4B, UBOX5, UBR5, WWP1, and WWP2.

22. The method of claim 20, wherein the disease or disorder is Parkinson's disease.

* * * * *

UNITED STATES PATENT AND TRADEMARK OFFICE
CERTIFICATE OF CORRECTION

| | |
|---|---|
| PATENT NO. | : 11,401,255 B2 |
| APPLICATION NO. | : 16/321208 |
| DATED | : August 2, 2022 |
| INVENTOR(S) | : Springer et al. |

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 275 days.

Signed and Sealed this
Thirteenth Day of June, 2023

Katherine Kelly Vidal
*Director of the United States Patent and Trademark Office*